United States Patent
Wells et al.

(10) Patent No.: US 8,642,788 B2
(45) Date of Patent: Feb. 4, 2014

(54) ACTIVATORS OF EXECUTIONER PROCASPASES 3, 6 AND 7

(75) Inventors: Jim Wells, Burlingame, CA (US); Adam R. Renslo, Oakland, CA (US); Dennis Wolan, San Francisco, CA (US); Julie Zorn, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 12/812,360

(22) PCT Filed: Jan. 9, 2009

(86) PCT No.: PCT/US2009/030680
§ 371 (c)(1),
(2), (4) Date: Oct. 4, 2010

(87) PCT Pub. No.: WO2009/089508
PCT Pub. Date: Jul. 16, 2009

(65) Prior Publication Data
US 2011/0021522 A1    Jan. 27, 2011

Related U.S. Application Data

(60) Provisional application No. 61/020,608, filed on Jan. 11, 2008.

(51) Int. Cl.
*C07D 311/02* (2006.01)

(52) U.S. Cl.
USPC .......................................................... 549/287

(58) Field of Classification Search
USPC .......................................................... 549/287
See application file for complete search history.

(56) References Cited

U.S. PATENT DOCUMENTS

| | | | |
|---|---|---|---|
| 6,342,516 B1 * | 1/2002 | Umeda et al. | 514/397 |
| 2003/0203909 A1 * | 10/2003 | Ushio et al. | 514/249 |
| 2003/0229132 A1 | 12/2003 | Nguyen et al. | |
| 2009/0163545 A1 * | 6/2009 | Goldfarb | 514/312 |

FOREIGN PATENT DOCUMENTS

WO   WO 2007124617   * 11/2007 ......... A91K 31/4439

OTHER PUBLICATIONS

Garino et al Bioorganic & Medicinal Chemistry Letters (2006),16(7), 1995-1999.*
Bassignana Tetrahedron (1964), 20(12), 2859-71.*

* cited by examiner

*Primary Examiner* — Nizal Chandrakumar
(74) *Attorney, Agent, or Firm* — Kilpatrick Townsend & Stockton LLP

(57) ABSTRACT

The present invention provides compounds as activators of procaspases 3, 6 and/or 7 and related derivatives, pharmaceutical compositions thereof, methods for their use, and methods for preparing these compounds. In one aspect, the compounds are useful for treating cancers and neoplastic diseases.

15 Claims, 6 Drawing Sheets

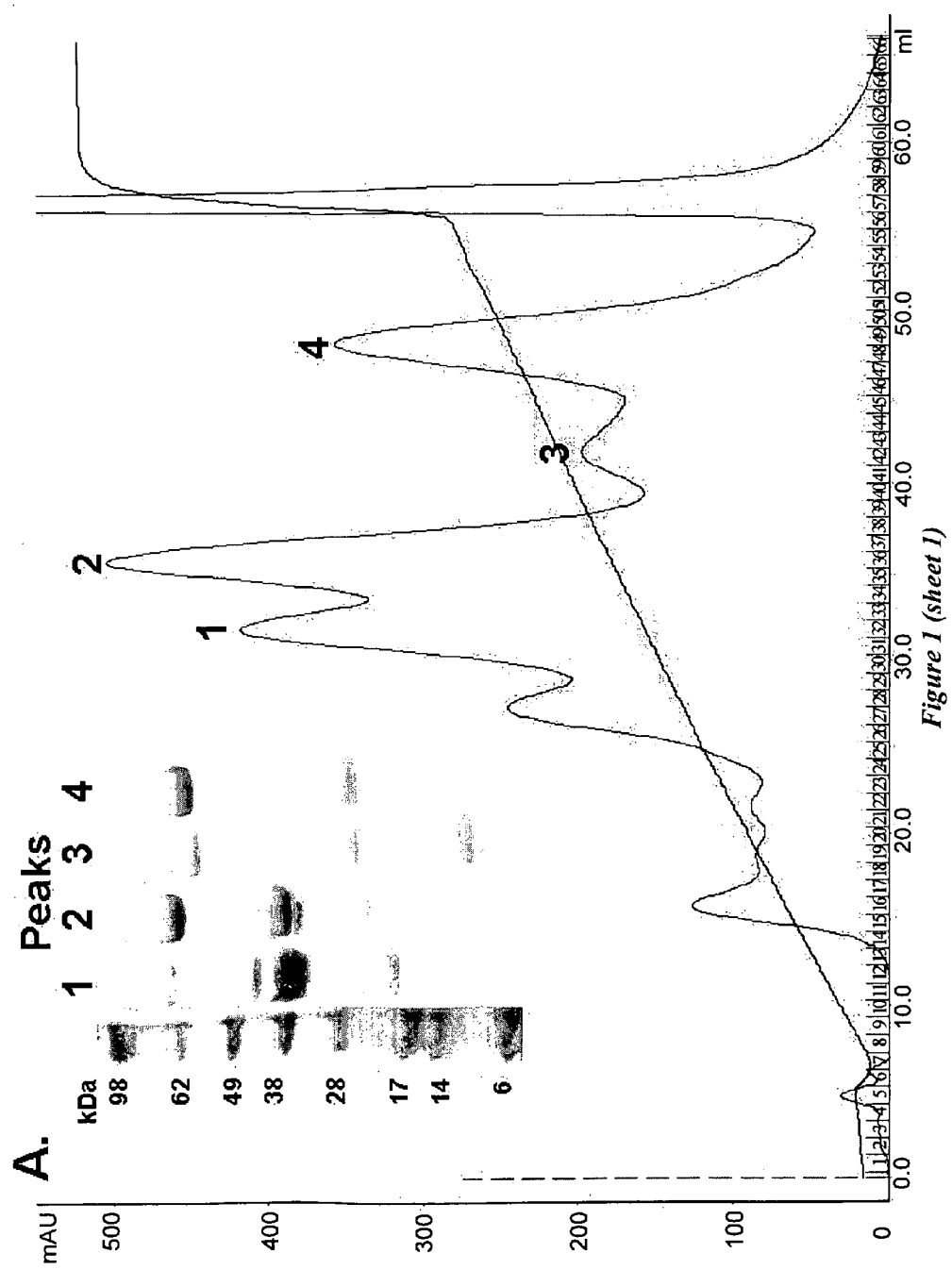
Figure 1 (sheet 1)

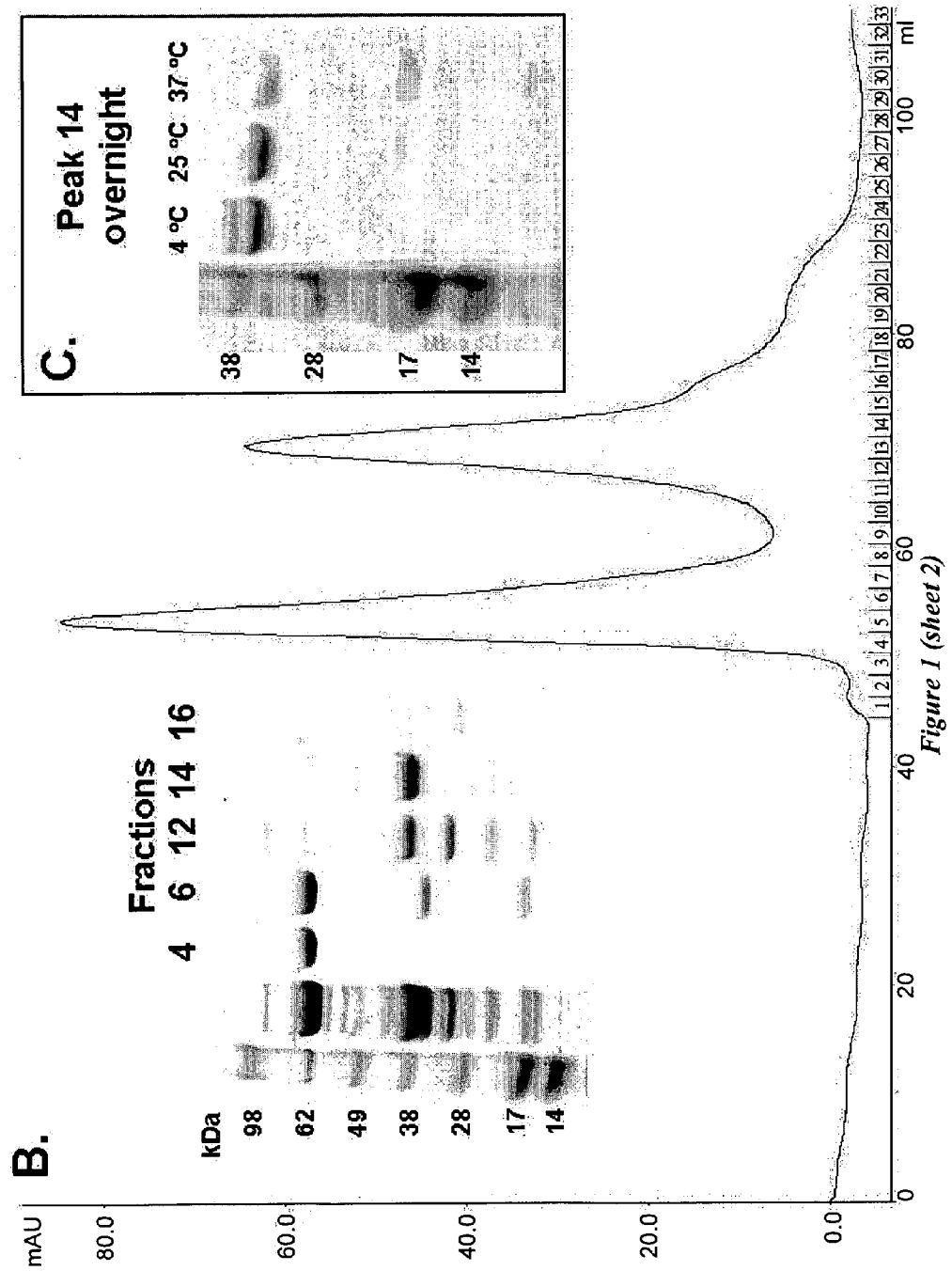
Figure 1 (sheet 2)

ACTIVATORS OF EXECUTIONER PROCASPASES 3, 6 AND 7

This application claims priority to U.S. Provisional Patent Application No. 61/020,608 filed Jan. 11, 2008, which application is incorporated herein by reference in its entirety and for all purposes.

STATEMENT AS TO RIGHTS TO INVENTIONS MADE UNDER FEDERALLY SPONSORED RESEARCH AND DEVELOPMENT

This Invention was made with Government support under National Institute of Health (NIH) Grants No. R21 NS057022 and No. R01 CA13677. The Government has certain rights in the invention.

BACKGROUND OF THE INVENTION

Programmed cell death, or apoptosis, is employed by multicellular organisms to eradicate physiologically-divergent cells that threaten development, homeostasis and overall survival. Disruption of the apoptotic cycle can lead to a number of life-threatening human disorders including cancer, immunodeficiency, autoimmune and neurodegenerative diseases. Historically, one focus of cancer research efforts has been centered on elucidation of regulatory mechanisms and identification of proteins responsible for programmed cell death in normal and transformed cells. Comparative analyses have illustrated the effects of various diseases and cancerous tumors on apoptotic dysfunction and, hence, have uncovered target proteins for therapeutic intervention.

A variety of pathways are available to initiate programmed cell death. The two main pathways are i) the extrinsic pathway, which relies on activation of cell surface death receptors by extracellular signals, and ii) the intrinsic pathway, which is dependent on release of cytochrome c from mitochondria as a result of cellular DNA damage or loss of survival signals. Both pathways activate a family of cysteine proteases, known as caspases, that specifically target and degrade vital cellular proteins for nuclear membrane and DNA fragmentation, chromatin condensation and eventual cell death. Caspases are heavily regulated proteins due to the extreme significance of their activity, as inappropriate activation can have devastating effects for the organism. Therefore, all caspases are synthesized as inactive procaspases for which activity is induced upon proteolysis of their maturation cleavage site and further regulated by specific intracellular protein inhibitors. Many cancers have been linked to deficiencies in caspase function and, as a result, represent an important class of drug targets for anti-neoplastic design. In addition, other disease states can be targeted by this class of drug.

Apoptotic caspases are divided into "initiators" and "executioners". The extrinsic and intrinsic apoptotic pathways utilize independent initiator caspases 8 and 9, respectively. Once activated, the initiator caspases 8 and 9 converge to activate executioner caspases 3, 6 and 7. The executioner procaspases 3, 6 and 7 represent a class of proteases believed solely responsible for the last step of the cellular apoptosis cascade by cleaving many proteins including actin, nuclear lamin and various regulatory proteins. Cancerous tissues have been shown to express elevated levels of the executioner procaspases and thus, represent an important target for anti-neoplastic intervention. Specifically, activation of executioner procaspases by small molecule agonists would promote cell death in lieu of upstream signaling cascades and cellular apoptosis inhibitors.

However, targeting members of the caspase family for therapeutic design has been a difficult endeavor as evidenced by the complete lack of caspase-directed therapies. Drug discovery efforts have been hampered by the stringent preference of all caspase active sites for a substrate electrophilic carbonyl and aspartyl functionality, thereby preventing diffusion of small molecule inhibitors across the cellular membrane during drug administration.

Therefore, there is a need to develop small molecule compounds and methods that are capable of specifically activating executioner procaspase 3, 6 and 7 both in vitro at physiological concentrations and promoting cellular apoptosis in vivo as well as exhibiting activity for treating various diseases including cancers and neoplastic diseases. The present invention meets this and other needs.

BRIEF SUMMARY OF THE INVENTION

The present invention provides compounds as novel activators of procaspases 3, 6 and 7 and related derivatives, pharmaceutical compositions thereof, methods for their use, and methods for preparing these compounds. These compounds are useful for treating neoplastic cancers and diseases and modulating other pharmacologies that depend on executioner caspase activation. The advantage in discovering agonists for this system is that active caspases feedback and catalytically generate more caspases for apoptosis. The potential benefits on how to regulate apoptosis by small molecule activation of procaspase structures have significant rewards, not only in the search for novel drugs to activate apoptosis in tumor cells, but also in the development of novel methods to target proteins for allosteric drug discovery.

In one aspect, the present invention provides a compound of formula I':

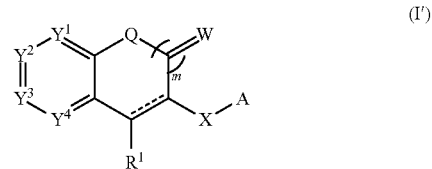

or a pharmaceutically acceptable salt thereof;
or a pharmaceutically acceptable salt thereof;
wherein
the subscript m is 0 or 1;
W is =O, =N—OR$^a$, =S, or together with the carbon atom to which it is attached forms CR$^a$R$^a$, wherein each R$^a$ is independently —H, C$_{1-6}$alkyl, aryl-C$_{1-6}$alkyl, C$_{2-6}$alkenyl, C$_{2-6}$alkynyl, —C$_{3-8}$cycloalkyl or optionally the two R$^a$ substituents together with the carbon atom to which they are attached form a 5- or 6-membered ring having from 0-2 ring heteroatoms selected from O, N or S, wherein the aliphatic portion of R$^a$ is optionally substituted with from 1-3 R$^h$ substituents;
Q is —O— or N—R$^a$;
X is a bond or selected from the group consisting of —C(=W$^1$)NH—, —C(=W$^1$)—C$_{0-4}$alkylene-, —SO$_2$NH—, —C$_{0-4}$alkylene-NHC(=W$^1$)—, —C$_{0-4}$alkylene-NH(C=W$^1$)O—, —C$_{0-4}$alkylene-NH(C=W$^1$)NH— and —C$_{0-4}$alkylene-C(=W$^1$)—, wherein each W$^1$ is independently O, N—OR$^a$, S, or together with the carbon atom to which it is attached forms CR$^a$R$^a$;

$Y^1, Y^2, Y^3, Y^4, Y^5,$ and $Y^6$ are each independently C—$R^2$ or N, wherein each $R^2$ is independently selected from the group consisting of —H, aryl-$C_{1-6}$alkyl, —$C_{1-6}$alkyl, —$OC_{1-6}$alkyl, —OH, halo, aryl-$C_{1-6}$alkyl-NH— and —$NHC_{1-6}$alkyl;

$R^1$ is independently —H, $C_{1-6}$alkyl, $C_{2-6}$alkenyl, $C_{2-6}$alkynyl or —$C_{3-8}$cycloalkyl;

A is —$C_{1-6}$alkyl-$R^3$ or a structure selected from the group consisting of (i), (ii) and (iii):

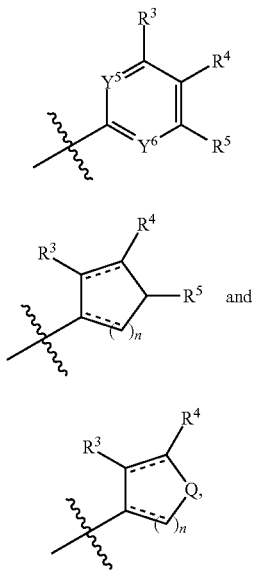

wherein $R^3$, $R^4$, and $R^5$ are each independently selected from the group consisting of —H, $C_{1-6}$alkyl, $C_{1-6}$alkoxy, $C_{1-6}$alkylamino, —NH(C=O)$R^b$, —$NHR^b$, —$OR^b$ and —$R^b$, —(C=O)$R^b$ and —(C=O)$NHR^b$, wherein $R^b$ is heteroaryl or heterocyclyl having from 1-4 ring heteroatoms selected from O, N or S, or an aryl, wherein the aryl or heteroaryl of $R^b$ is optionally substituted with from 1-3 $R^k$ members independently selected from the group consisting of $C_{1-4}$alkyl, aryl-$C_{1-4}$alkyl, halo, haloalkyl, —$OR^c$, —$SR^c$, —CN, —$NO_2$, $NR^cR^d$, oxo, $C_{1-4}$alkyl (C=O)NH—, haloalkoxy, —C(=O)$C_{1-4}$alkyl, OC(=O)$C_{1-4}$alkyl, —C(=O)$OR^c$, S(O)$C_{1-4}$alkyl, S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members; wherein $R^c$ and $R^d$ are each independently selected from the group consisting of —H, $C_{1-6}$alkyl, —$R^e$, —$NHC_{1-6}$alkyl and —NH(C=O)$R^e$, wherein $R^e$ is a heteroaryl or heterocyclyl having from 1-4 ring heteroatoms selected from O, N or S or an aryl, wherein the aryl or heteroaryl is further optionally substituted with from 1-3 $R^f$ selected from the group consisting of halo, haloalkyl, —OH, —$OR^g$, —$SR^g$, —CN, —$NO_2$, $NR^gR^g$, oxo, haloalkoxy, —C(=O)$C_{1-4}$alkyl, OC(=O)$C_{1-4}$alkyl, —C(=O)$OR^g$, S(O)$C_{1-4}$alkyl and S(O)$_2C_{1-4}$alkyl, wherein $R^g$ is $C_{1-6}$alkyl; and wherein each subscript n is independently an integer selected from 0, 1, 2, or 3; and wherein:
the moiety ----- is a single bond or a double bond;
the aliphatic portions of $R^1$, $R^2$, $R^3$, $R^4$ and $R^5$ are each optionally independently substituted with from 1-3 $R^h$ substituents selected from the group consisting of $C_{1-6}$alkyl, $C_{1-6}$haloalkyl, $C_{1-6}$haloalkoxy, $C_{3-8}$cycloalkyl or $C_{2-6}$alkenyl is optionally substituted with $C_{1-6}$haloalkyl, halo, OH, $C_{1-4}$alkoxy, —$NHC_{1-4}$ alkyl, N($C_{1-4}$ alkyl)$_2$, —CN, —$N_3$, —O(C=O)$C_{1-4}$ alkyl, $C_{3-6}$cycloalkyl, —$NH_2$, —NHC(=O)$C_{1-4}$alkyl, —C(=O)$C_{1-4}$ alkyl, $OR^c$, $SR^c$, CN, —$NO_2$, $NR^cR^d$, C(=O)$OC_{1-4}$alkyl, S(O)$C_{1-4}$alkyl and S(O)$_2C_{1-4}$alkyl; and with the proviso when X is —(C=O)—, $R^3$ is not —H, alkyl or $R^b$ and subscript n is not 0

In another aspect, the present invention provides a compound of formula I:

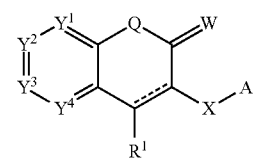

I or a pharmaceutically acceptable salt thereof;
wherein

W is =O, =N—$OR^a$, =S, or together with the carbon atom to which it is attached forms $CR^aR^a$, wherein each $R^a$ is independently —H, $C_{1-6}$alkyl, aryl-$C_{1-6}$alkyl, $C_{2-6}$alkenyl, $C_{2-6}$alkynyl, —$C_{3-8}$cycloalkyl or optionally the two $R^a$ substituents together with the carbon atom to which they are attached form a 5- or 6-membered ring having from 0-2 ring heteroatoms selected from O, N or S, wherein the aliphatic portion of $R^a$ is optionally substituted with from 1-3 $R^h$ substituents;

Q is —O— or N—$R^a$;

X is a bond or selected from the group consisting of —C(=$W^1$)NH—, —C(=$W^1$)—$C_{0-4}$alkylene-, —$SO_2$NH—, —$C_{0-4}$alkylene-NHC(=$W^1$)—, —$C_{0-4}$alkylene-NH(C=$W^1$)O—, —$C_{0-4}$alkylene-NH(C=$W^1$)NH— and —$C_{0-4}$alkylene-C(=$W^1$)—, wherein each $W^1$ is independently O, N—$OR^a$, S, or together with the carbon atom to which it is attached forms $CR^aR^a$;

$Y^1, Y^2, Y^3, Y^4, Y^5,$ and $Y^6$ are each independently C—$R^2$ or N, wherein each $R^2$ is independently selected from the group consisting of —H, aryl-$C_{1-6}$alkyl, —$C_{1-6}$alkyl, —$OC_{1-6}$alkyl, —OH, halo, aryl-$C_{1-6}$alkyl-NH— and —$NHC_{1-6}$alkyl;

$R^1$ is independently —H, $C_{1-6}$alkyl, $C_{2-6}$alkenyl, $C_{2-6}$alkynyl or —$C_{3-8}$cycloalkyl;

A is —$C_{1-6}$alkyl-$R^3$ or a structure selected from the group consisting of (i), (ii) and (iii):

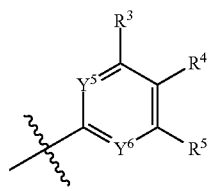

i

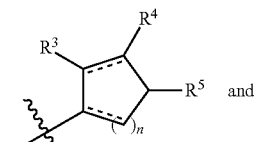

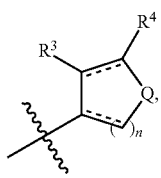

wherein $R^3$, $R^4$, and $R^5$ are each independently selected from the group consisting of —H, $C_{1-6}$alkyl, $C_{1-6}$alkoxy, $C_{1-6}$alkylamino, —NH(C=O)$R^b$, —NH$R^b$, —O$R^b$ and —$R^b$, —(C=O)$R^b$ and —(C=O)NH$R^b$, wherein $R^b$ is heteroaryl or heterocyclyl having from 1-4 ring heteroatoms selected from O, N or S, or an aryl, wherein the aryl or heteroaryl of $R^b$ is optionally substituted with from 1-3 $R^k$ members independently selected from the group consisting of $C_{1-4}$alkyl, aryl-$C_{1-4}$alkyl, halo, haloalkyl, —O$R^c$, —S$R^c$, —CN, —NO$_2$, N$R^c R^d$, oxo, $C_{1-4}$alkyl (C=O)NH—, haloalkoxy, —C(=O)$C_{1-4}$alkyl, OC(=O)$C_{1-4}$alkyl, —C(=O)O$R^c$, S(O)$C_{1-4}$alkyl, S(O)$_2$heterocycloalkyl and S(O)$_2 C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members; wherein $R^c$ and $R^d$ are each independently selected from the group consisting of —H, $C_{1-6}$alkyl, —$R^e$, —NH$C_{1-6}$alkyl and —NH(C=O)$R^e$, wherein $R^e$ is a heteroaryl or heterocyclyl having from 1-4 ring heteroatoms selected from O, N or S or an aryl, wherein the aryl or heteroaryl is further optionally substituted with from 1-3 $R^f$ selected from the group consisting of halo, haloalkyl, —OH, —O$R^g$, —S$R^g$, —CN, —NO$_2$, N$R^g R^g$, oxo, haloalkoxy, —C(=O)$C_{1-4}$alkyl, OC(=O)$C_{1-4}$alkyl, —C(=O)O$R^g$, S(O)$C_{1-4}$alkyl and S(O)$_2 C_{1-4}$alkyl, wherein $R^5$ is $C_{1-6}$alkyl; and wherein each subscript n is independently an integer selected from 0, 1, 2, or 3; and wherein:

the moiety ----- is a single bond or a double bond;

the aliphatic portions of $R^1$, $R^2$, $R^3$, $R^4$ and $R^5$ are each independently substituted with from 1-3 $R^h$ substituents selected from the group consisting of $C_{1-6}$alkyl, $C_{1-6}$haloalkyl, $C_{1-6}$haloalkoxy, $C_{3-8}$cycloalkyl or $C_{2-6}$alkenyl is optionally substituted with $C_{1-6}$haloalkyl, halo, OH, $C_{1-4}$alkoxy, —NH$C_{1-4}$ alkyl, N($C_{1-4}$ alkyl)$_2$, —CN, —N$_3$, —O(C=O)$C_{1-4}$ alkyl, $C_{3-6}$cycloalkyl, —NH$_2$, —NHC(=O)$C_{1-4}$ alkyl, —C(=O)$C_{1-4}$ alkyl, O$R^c$, S$R^c$, CN, —NO$_2$, N$R^c R^d$, C(=O)O$C_{1-4}$alkyl, S(O)$C_{1-4}$alkyl and S(O)$_2 C_{1-4}$alkyl; and with the proviso when X is —(C=O)—, $R^3$ is not —H, alkyl or $R^b$ and subscript n is not 0. In one embodiment, the compounds have formula Ia:

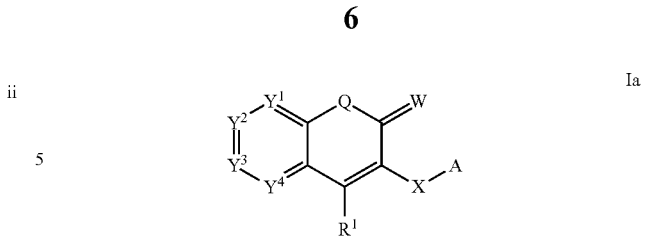

In yet another aspect, the present invention provides a pharmaceutical composition comprising a compound of formula I and a pharmaceutically acceptable carrier or excipient.

In still another aspect, the present invention provides a method of activating executioner procaspase 3, 6 and/or 7 in a subject in need thereof. The method includes contacting a compound of formula I with executioner procaspase 3, 6 and/or 7 receptor under conditions sufficient to activate executioner procaspase 3, 6 and/or 7. In one embodiment, the present invention provides a method for treating and/or preventing diseases in a mammal, including, but not limited to, cancer and neoplastic diseases. The method includes administering to the mammal a therapeutically effective amount of a compound of formula I or a pharmaceutically acceptable salt thereof.

BRIEF DESCRIPTION OF THE DRAWINGS

FIG. 1. Purification of procaspase-7. A. Elution of procaspase-7 from HiTrap Q anion exchange column with corresponding peaks labeled on SDS-PAGE gel. Peak 2 contains monomeric procaspase-7 and was pulled for gel filtration. B. Gel filtration of peak 2 from Q column with corresponding peak fractions ran on a SDS-PAGE gel. Monomeric procaspase-7 elutes in peak 14 and is approximately 95% pure. C. Monomeric procaspase-7 incubated overnight depicts loss of the prodomain residues (1-23) at 4° C., slight self-cleavage to the large and small domains of active caspase-7 at 25° C. and approximately 50% autocatalysis at 37° C.

DETAILED DESCRIPTION OF THE INVENTION

I. Introduction

Figure 2:
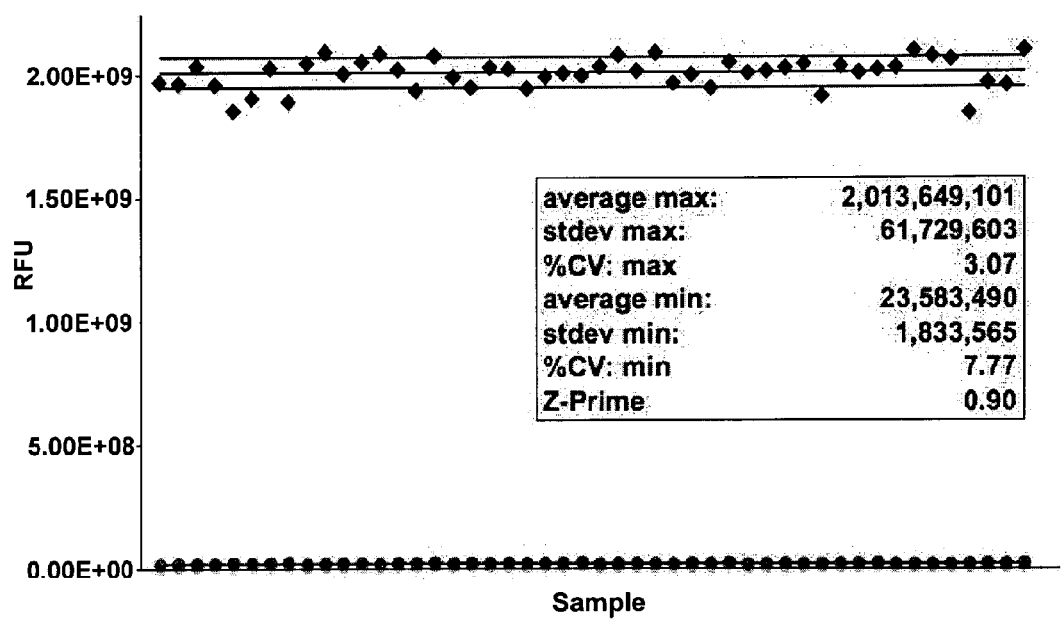
FIG. 2. Z' determination for active caspase-7. Similar results are expected for the procaspase-7 HTS assay for agonists.

The executioner procaspases 3, 6 and 7 represent a class of proteases solely responsible for the last step of the cellular apoptosis cascade by cleaving many proteins including actin, nuclear lamin and various regulatory proteins. Cancerous tissues have been shown to express elevated levels of the executioner procaspases and thus, represent an important target for anti-neoplastic intervention. Specifically, activation of executioner procaspases by small molecule agonists would promote cell death in lieu of upstream signaling cascades and cellular apoptosis inhibitors. Novel compounds of formula I that have been shown to specifically activate executioner procaspase 3, 6 and 7 both in vitro and in vivo. This novel class of compounds provides an important foundation for iterative development as anti-cancer agents, as well as for treating other diseases.

Without being limited to the present mechanism, two processing sites are cleaved in the executioner caspases for activation. One is between the pro-sequence and the large subunit, and one is between the large and small subunit. In the case of procaspase 3 and 6, once the compounds of the invention generate some mature caspase-3 or -6, they can autoclave other molecules of procaspase-3 and -6, leading to an explosive activation. At lower concentrations, procaspase-7 can only autoclave the junction between the pro sequence and the large subunit. However, it does self-activate at higher concentrations. Higher concentrations of caspase-7 can occur in cancerous cells and thus autoactivation is possible.

II. Definitions

As used herein, the term "alkyl" refers to a straight or branched, saturated, aliphatic radical having the number of carbon atoms indicated (i.e. $C_{1-8}$ or $C_1$-$C_8$ means one to eight carbons. For example, $C_1$-$C_6$ alkyl includes, but is not limited to, methyl, ethyl, propyl, isopropyl, butyl, pentyl, hexyl, isopropyl, iso-butyl, sec-butyl, tert-butyl, etc. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms. For example, $C_{1-8}$alkyl refers to a hydrocarbon radical straight or branched having 1, 2, 3, 4, 5, 6, 7 or 8 carbon atoms and includes, but are not limited to, $C_{1-2}$alkyl, $C_{1-4}$ alkyl, $C_{2-6}$ alkyl, $C_{2-4}$ alkyl, $C_{1-6}$ alkyl, $C_{2-8}$alkyl, $C_{1-7}$alkyl, $C_{2-7}$alkyl and $C_{3-8}$ alkyl.

As used herein, the term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention.

As used herein, the term "alkenyl" refers to a linear monovalent hydrocarbon radical or a branched monovalent hydrocarbon radical having the number of carbon atoms indicated in the prefix and containing at least one double bond. For example, ($C_2$-$C_6$)alkenyl is meant to include ethenyl, propenyl, and the like.

As used herein, the term "alkynyl" refers to a linear monovalent hydrocarbon radical or a branched monovalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR'R" is meant to include piperidinyl, pyrrolidinyl, morpholinyl, azetidinyl and the like.

As used herein, the term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl.

As used herein, the term "cycloalkyl-alkyl" refers to a radical —R'R", where R' is an alkylene group (having the indicated number of carbon atoms, or if unspecified having six or fewer main chain carbon atoms) and R" is a cycloalkyl group as defined herein. Examples of cycloalkylalkyl include cyclohexylmethyl, pentylethyl and the like.

As used herein, the term "aryl" refers to, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

As used herein the term "arylalkyl" refers to a radical —R'R", where R' is an alkylene group (having the indicated number of carbon atoms, or if unspecified having six or fewer main chain carbon atoms) and R" is an aryl group as defined herein. Examples of arylalkyl include benzyl, phenethyl and the like.

As used herein, the term "heteroalkyl," by itself or in combination with another term, refers to, unless otherwise stated, a stable straight or branched chain, or combinations thereof, consisting of the stated number of carbon atoms and from one to three heteroatoms selected from the group consisting of O, N, Si, for example, Si, S, —N—, —N—, —N=, —O, —O—, O=, —S—, —SO— and —S(O)$_2$—, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

As used herein, the term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system. The heterocycloalkyl can also be a heterocyclic alkyl ring fused with an aryl or a heteroaryl ring. Non-limiting examples of heterocycloalkyl groups include pyrrolidinyl, piperidinyl, imidazolidinyl, pyrazolidinyl, butyrolactam, valerolactam, imidazolidinone, hydantoin, dioxolane, phthalimide, piperidine, 1,4-dioxanyl, morpholinyl, thiomorpholinyl, thiomorpholinyl-S-oxide, piperazinyl, pyranyl, thiopyranyl, pyrone, tetrahydrofuranyl, tetrahydrothiophenyl, quinuclidinyl, and the like. A heterocycloalkyl group can be attached to the remainder of the molecule through a ring carbon or a heteroatom.

As used herein, the term "heterocycloalkylalkyl" refers to a radical —R'R", where R' is an alkylene group (having the indicated number of carbon atoms, or if unspecified having six or fewer main chain carbon atoms) and R" is a heterocycloalkyl group as defined herein. Examples of heterocycloalkylalkyl include piperidinylmethyl, tetrahydrofuranylethyl and the like.

As used herein the term "heterocyclic" or "heterocyclyl" refers to a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. Examples of heterocyclyl include, but is not limited to, tetrahydropyranyl, piperidino, N-methylpiperidin-3-yl, piperazino, N-methylpyrrolidin-3-yl, 3-pyrrolidino, 3-pyrrolinyl, 2-pyrrolidon-1-yl, morpholino, thiomorpholino, thiomorpholino-1-oxide, thiomorpholino-1,1-dioxide, pyrrolidinyl, and the like.

As used herein the term "heterocyclylalkyl" refers to a radical —R'R", where R' is an alkylene group (having the indicated number of carbon atoms, or if unspecified having six or fewer main chain carbon atoms) and R" is a heterocyclyl group as defined herein. Examples of heterocyclylalkyl include piperidinylmethyl, tetrahydrofuranylethyl, pyronylmethyl, 3-pyrrolinylmethyl and the like.

As used herein, the term "heteroaryl" refers to aryl groups (or rings) that contain from one to five heteroatoms selected from N, O, or S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimidinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

As used herein, the term "heteroarylalkyl" refers to a radical —R'R", where R' is an alkylene group (having the indicated number of carbon atoms, or if unspecified having six or fewer main chain carbon atoms) and R" is a heteroaryl group as defined herein. Examples of heteroarylalkyl include pyridylmethyl, pyrazolyethyl, benzimidazolylmethyl and the like.

As used herein, the terms "halo" or "halogen," by themselves or as part of another substituent, mean, unless otherwise stated, a fluorine, chlorine, bromine, or iodine atom.

As used herein, the term "haloalkyl," refers to monohaloalkyl and polyhaloalkyl. For example, the term "$C_{1-4}$haloalkyl" is meant to include trifluoromethyl, 2,2,2-trifluoroethyl, 4-chlorobutyl, 3-bromopropyl, and the like.

As used herein, substituents for the aryl and heteroaryl groups are varied, unless indicated, and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, unsubstituted aryl and heteroaryl, (unsubstituted aryl)-$C_{1-4}$ alkyl, and unsubstituted aryloxy-$C_{1-4}$ alkyl.

As used herein, the term "protecting group" or "protected form thereof" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also, Boyle, A. L. (Editor), CURRENT PROTOCOLS IN NUCLEIC ACID CHEMISTRY, John Wiley and Sons, New York, Volume 1, 2000).

The term "composition" as used herein is intended to encompass a product comprising the specified ingredients in the specified amounts, as well as any product which results, directly or indirectly, from combination of the specified ingredients in the specified amounts.

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "inhibiting" refers to a compound that partially or fully prohibits or a method of partially or fully prohibiting a specific action or function. "Activating" refers to a compound that partially or fully induces or promotes a functional molecule or action.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington: The Science and Practice of Pharmacy, 21st ed., Lippincott Williams & Wilkins, Easton Pa., 2005, which is incorporated herein by reference.

As used herein, pharmaceutically acceptable salts of the basic compounds of the present invention are salts formed with acids, such as of mineral acids, organic carboxylic and organic sulfonic acids, e.g., hydrochloric acid, methanesulfonic acid, maleic acid, are also possible provided a basic group, such as pyridyl, constitutes part of the structure.

As used herein, the term "leaving group" has the meaning conventionally associated with it in synthetic organic chemistry i.e., an atom or group capable of being displaced by a nucleophile and includes halogen, alkylsulfonyloxy, ester, or amino such as chloro, bromo, iodo, mesyloxy, tosyloxy, trifluorosulfonyloxy, methoxy, N,O-dimethylhydroxyl-amino, and the like.

Abbreviations which are well known to one of ordinary skill in the art may be used (e.g. "Ph" for phenyl, "Me" for methyl, "Et" for ethyl, "h" for an hour or hours and "rt" for room temperature).

As used herein, "pharmaceutically acceptable" is meant the carrier, diluent or excipient must be compatible with the other ingredients of the formulation and not deleterious to the recipient thereof. The term "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "mammal" refers to human or warm-blooded animals including livestock and companion animals.

As used herein, the term "tumor" refers to all neoplastic cell growth and proliferation, whether malignant or benign, and all pre-cancerous and cancerous cells and tissues.

As used herein, the term "cancer" or "neoplastic disease" refers to a disease involving cells that have the potential to metastasize to distal sites and exhibit phenotypic traits that differ from those of non-cancer cells. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells. Neoplastic diseases can include, but are not limited to intraepithelial neoplasias, cervical dysplasia, actinic keratosis.

"Cancer" therefore refers to human cancers and carcinomas, sarcomas, adenocarcinomas, lymphomas, leukemias, etc., including solid and lymphoid cancers, kidney, breast, lung, kidney, bladder, colon, ovarian, prostate, pancreas, stomach, brain, head and neck, skin, uterine, testicular, esophagus, and liver cancer, including hepatocarcinoma, basal cell carcinoma, squamous cell carcinoma, Kaposi's sarcoma, melanoma, lymphoma, including non-Hodgkin's lymphomas (e.g., Burkitt's, Small Cell, and Large Cell lymphomas) and Hodgkin's lymphoma, leukemia, and multiple myeloma.

As used herein, the terms "prevent," "preventing" and "prevention" refer to the prevention of the recurrence, worsening, or spread of a disease in a subject resulting from the administration of a prophylactic or therapeutic agent.

As used herein, the term "optional" or "optionally" means that the subsequently described event or circumstance may, but need not, occur, and that the description includes instances where the event or circumstance occurs and instances in which it does not.

The following abbreviations are used in the Examples and throughout the description of the invention:

bm=broad multiplet
BOC=tert-butoxycarbonyl
bd=broad doublet
bs=broad singlet
CDI=1,1 O-carbodiimidazole
DIEA=diisopropylethylamine
d=doublet
dd=doublet of doublets
dq=doublet of quartets
dt=doublet of triplets
DMF=dimethylformamide
DMAP=dimethylaminopyridine
DMSO=dimethyl sulfoxide
eq.=equivalents
g=grams
h=hours
HPLC=high pressure liquid chromatography
HATU=N-[(dimethylamino)-1H-1,2,3-triazolo-[4,5-b]pyridin-1-yl-methylene]-N-methylmethanaminium hexafluorophosphate N-oxide
LG=leaving group
m=multiplet
M=molar
M %=mole percent
max=maximum
meq=milliequivalent
mg=milligram
mL=milliliter
mm=millimeter
mmol=millimol
q=quartet
s=singlet
t or tr=triplet
TBS=tributylsilyl
TFA=trifluoroacetic acid
THF=tetrahydrofuran
TLC=thin layer chromatography
p-TLC=preparative thin layer chromatography
μL=microliter
N=normality
MeOH=methanol
DCM=dichloromethane
HCl=hydrochloric acid
ACN=acetonitrile
MS=mass spectrometry
rt=room temperature
EtOAc=ethyl acetate
EtO=ethoxy
Ac=acetate
NMP=1-methyl-2-pyrrolidinone
μL=microliter
J=coupling constant
NMR=Nuclear magnetic resonance MHz=megahertz
Hz=hertz
m/z=mass to charge ratio
min=minutes
Boc=tert-butoxycarbonyl
CBZ=benzyloxycarbonyl
DCC=1,3-dicyclohexylcarbodiimide
PyBop=benzotriazole-1-yl-oxy-trispyrrolidinophosphonium hexafluorophosphate III. Compounds In one aspect, the present invention provides a compound of formula (I'):

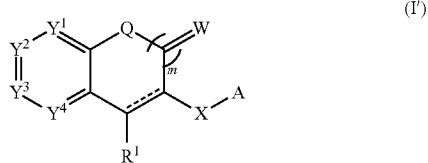

(I')

or a pharmaceutically acceptable salt thereof, wherein the moiety ----- is a single bond or a double bond. In one embodiment, the moiety ----- is a double bond and m is 0. The substituents $Y^1$, $Y^2$, $Y^3$, $Y^4$, W, Q, $R^1$, X and A are as defined above. In some embodiments, m is 0, $Y^2$, $Y^3$ and $Y^4$ are —CH=, $Y^1$ is —C(OC$_{1-4}$alkyl)=, Q is O and A is heteroaryl.

In another aspect, the present invention provides a compound of formula I:

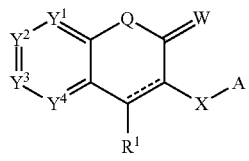

I or a pharmaceutically acceptable salt thereof, wherein the moiety ----- is a single bond or a double bond. In one embodiment, the moiety ----- is a double bond.

In formula I, A is —C$_{1-6}$alkyl-$R^3$ or a structure selected from the group consisting of (i), (ii) and (iii):

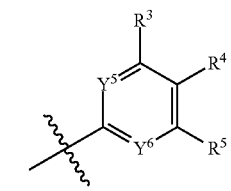

i

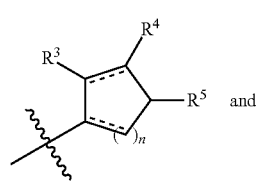

ii and

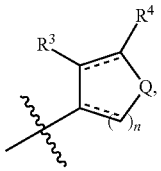

iii wherein each n is independently an integer selected from 0, 1, 2, or 3. In one embodiment, A is a structure having formula (i). In one embodiment, $Y^5$ and $Y^6$ are each independently $CR^2$ or N. In another embodiment, $Y^5$ is $CR^2$ and $Y^6$ is N. In yet another embodiment, $Y^5$ and $Y^6$ are CH or N. In certain instances, $R^2$ is —H, $C_{1-6}$alkyl, haloalkyl or alkoxy.

In a group of embodiments of compounds having formula I, $R^3$, $R^4$, and $R^5$ are each independently selected from the group consisting of —H, $C_{1-6}$alkyl, $C_{1-6}$alkoxy, $C_{1-6}$alkylamino, —NH(C=O)$R^b$, —NHR$^b$, —OR$^b$ and —R$^b$, —(C=O)$R^b$ and —(C=O)NHR$^b$, wherein $R^b$ is heteroaryl or heterocyclyl having from 1-4 ring heteroatoms selected from O, N or S, or an aryl, wherein the aryl or heteroaryl is optionally substituted with from 1-3 $R^k$ members independently selected from the group consisting of $C_{1-4}$alkyl, aryl-$C_{1-4}$alkyl, halo, haloalkyl, —OR$^c$, —SR$^c$, —CN, —NO$_2$, NR$^c$R$^d$, oxo, $C_{1-4}$alkyl(C=O)NH—, haloalkoxy, —C(=O)$C_{1-4}$alkyl, OC(=O)$C_{1-4}$alkyl, —C(=O)OR$^c$, S(O)$C_{1-4}$alkyl, S(O)$_2$heterocycloalkyl and S(O)$_2$C$_{1-4}$alkyl; or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members; wherein $R^c$ and $R^d$ are each independently selected from the group consisting of —H, $C_{1-6}$alkyl, —$R^e$, —NHC$_{1-6}$alkyl and —NH(C=O)$R^e$, wherein $R^e$ is a heteroaryl or heterocyclyl having from 1-4 ring heteroatoms selected from O, N or S or an aryl, wherein the aryl or heteroaryl is further optionally substituted with from 1-3 $R^f$ selected from the group consisting of halo, haloalkyl, —OH, —OR$^g$, —SR$^g$, —CN, —NO$_2$, NR$^g$R$^g$, oxo, haloalkoxy, —C(=O)$C_{1-4}$alkyl, OC(=O)$C_{1-4}$alkyl, —C(=O)OR$^g$, S(O)$C_{1-4}$alkyl and S(O)$_2$C$_{1-4}$alkyl, wherein $R^g$ is $C_{1-6}$alkyl; and wherein each subscript n is independently an integer selected from 0, 1, 2, or 3. The 5- or 6-membered heteroaryl or heterocycloalkyl ring formed by two adjacent $R^k$ substituents are optionally substituted with a $R^c$ group, preferably with a $C_{1-8}$alkyl. In certain instances, $R^b$ is a heteroaryl or heterocyclyl substituted with 1-3 members selected from —CF$_3$, —OCF$_3$, —OH, —OCH$_3$, —F, —Cl, —OC$_{1-6}$alkyl, —SC$_{1-6}$alkyl, —CN, —NO$_2$, NR$^c$R$^d$, oxo, —C(=O)$C_{1-4}$alkyl, OC(=O)$C_{1-4}$alkyl, —C(=O)OR$^5$, S(O)$C_{1-4}$alkyl and S(O)$_2$C$_{1-4}$alkyl.

In some embodiments, $R^3$ is —H or heteroaryl. In certain instances, $R^3$ is hetero($C_{3-8}$)aryl. In certain other instances, $R^3$ is a fused bicyclic heteroaryl. Non-limiting exemplary $R^3$ substituent includes benzimidazolyl and imidazo[1,2-a]pyridinyl.

In formula I, W is =O, =N—OR$^a$, =S, or together with the carbon atom to which it is attached forms CR$^a$R$^a$, wherein each $R^a$ is independently —H, $C_{1-6}$alkyl, aryl-$C_{1-6}$alkyl, $C_{2-6}$alkenyl, $C_{2-6}$alkynyl, —$C_{3-8}$cycloalkyl or optionally the two $R^a$ groups together with the carbon atom to which they are attached form a 5- or 6-membered ring having from 0-2 ring heteroatoms selected from O, N or S, wherein the aliphatic portion of $R^a$ is optionally substituted with from 1-3 $R^h$ substituents selected from the group consisting of $C_{1-6}$alkyl, $C_{3-8}$cycloalkyl or $C_{2-6}$alkenyl is optionally substituted with $C_{1-6}$haloalkyl, $C_{1-6}$haloalkoxy, halo, OH, $C_{1-4}$alkoxy, —NHC$_{1-4}$alkyl, N(C$_{1-4}$alkyl)$_2$, —CN, —N$_3$, —O(C=O)$C_{1-4}$alkyl, $C_{3-6}$cycloalkyl, —NH$_2$, —NHC(=O)$C_{1-4}$alkyl, —C(=O)$C_{1-4}$alkyl, OR$^c$, SR$^c$, CN, —NO$_2$, NR$^c$R$^d$, C(=O)

$OC_{1-4}$alkyl, $S(O)C_{1-4}$alkyl and $S(O)_2C_{1-4}$alkyl. In one embodiment, W is =O, =S or =N—$OC_{1-6}$alkyl. In another embodiment, W is =O.

In a group of embodiments of compounds having formula I, $R^h$ is selected from the group consisting of —$CF_3$, $CF_3O$, halo, OH, $C_{1-4}$alkoxy, —$NHC_{1-4}$ alkyl, $N(C_{1-4}$ alkyl$)_2$, —CN, —$N_3$, —O(C=O)$C_{1-4}$ alkyl, $C_{3-6}$cycloalkyl, —$NH_2$, —NHC(=O)$C_{1-4}$ alkyl, —C(=O)$C_{1-4}$ alkyl, —$OR^e$, —O($C_{1-6}$alkyl), —$SR^e$, —S($C_{1-6}$alkyl), —CN, —$NO_2$, —$NR^eR^e$, —N($C_{1-6}$alkyl)$_2$, C(=O)O$C_{1-4}$alkyl, $S(O)C_{1-4}$alkyl and $S(O)_2C_{1-4}$alkyl.

In formula I, $R^1$ is —H, $C_{1-6}$alkyl, $C_{2-6}$alkenyl, $C_{2-6}$alkynyl or —$C_{3-8}$cycloalkyl, wherein the aliphatic portion of $R^1$ is optionally substituted with from 1-3 $R^h$ substituents. In one embodiment, $R^1$ is —H or $C_{1-6}$alkyl.

In formula I, Q is —O— or N—$R^a$, wherein the aliphatic portion of $R^a$ is optionally substituted with from 1-3 $R^h$. In one embodiment, Q is —O—.

In formula I, X is selected from the group consisting of —C(=$W^1$)NH—, —C(=$W^1$)—$C_{0-4}$alkylene-, —$SO_2$NH—, —$C_{0-4}$alkylene-NHC(=$W^1$)—, —$C_{0-4}$alkylene-NH(C=$W^1$)O—, —$C_{0-4}$alkylene-NH(C=$W^1$)NH— and —$C_{0-4}$alkylene-C(=$W^1$)—, wherein each $W^1$ is independently =O, =N—$OR^a$, S, or together with the carbon atom to which it is attached forms $CR^aR^a$, wherein the aliphatic portion of $R^a$ is optionally substituted with from 1-3 $R^h$. In one group of embodiment, $W^1$ is =O. In another group of embodiments, X is —C(=O)NH—.

In formula I, $Y^1$, $Y^2$, $Y^3$, $Y^4$, $Y^5$, and $Y^6$ are each independently C—$R^2$ or N. In one embodiment, $Y^1$, $Y^2$, $Y^3$ and $Y^4$ are $CR^2$. In one instance, $Y^1$, $Y^2$, $Y^3$ and $Y^4$ are —H. In another instance, $Y^2$, $Y^3$ and $Y^4$ are —H and $Y^1$ is —OH, $C_{1-6}$haloalkoxy or $C_{1-6}$alkoxy. In yet another instance, $Y^2$, $Y^3$ and $Y^4$ are —H and $Y^1$ is —OH, —OMe or —$OCF_3$.

In a group of embodiments of compounds having formula I, $R^2$ is independently selected from the group consisting of —H, aryl-$C_{1-6}$alkyl, —$C_{1-6}$alkyl, —$OC_{1-6}$alkyl, —OH, halo, aryl-$C_{1-6}$alkyl-NH— and —$NHC_{1-6}$alkyl, the aliphatic portion of $R^2$ is optionally substituted with from 1-3 $R^h$. In one instance, $R^2$ is —H, —OMe, —OH, F, Cl, Br, —$NHC_{1-6}$ alkyl, benzyl or benzylamino. In another instance, $R^2$ is —H or $C_{1-6}$alkoxy.

In certain embodiments, the heterocyclic (heteroaryl and/or heterocyclyl) rings include, but are not limited to, azetidine, pyrrole, imidazole, pyrazole, 1,2,3-triazole, 1,3,4-triazole, oxazole, thiazole, isoxazole, isothiazole, 1,3,4-oxadiazole, 1,3,4-thiadiazole, 1,2,3-thiadiazole, tetrazole, pyridine, pyrazine, pyrimidine, pyridazine, indolizine, isoindole, indole, dihydroindole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazole, tetrazole, thiazolidine, thiophene, benzo[b]thiophene, morpholine, thiomorpholine, (also referred to as thiamorpholine), piperidine, pyrrolidine, tetrahydrofuran, and the like.

In certain other embodiments, heteroaryls include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxaz-olyl, 4-is-oxaz-olyl, 5-isoxaz-olyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,3-triazole-1-yl, 1,2,4-triazol-3-yl, 1,2,4-triazol-5-yl, tetrazole-1-yl, 1,2,3,4-tetrazol-5-yl, 5-oxazolyl, 3-isothiazolyl, 4-isothiazolyl and 5-isothiazolyl, 1,3,4-oxadiazole, 4-oxo-2-thiazolinyl, or 5-methyl-1,3,4-thiadiazol-2-yl, thiazoledione, 1,2,3,4-thiatriazole, or 1,2,4-dithiazolone and the like.

In yet certain other embodiments, heteroaryls include, but are not limited to, benzimidazolyl, benzimidazol-2yl, benzopyrazolyl, benzotriazolyl, benzotetrazolyl, benzooxazolyl, benzoisoxazolyl, benzooxadiazolyl, benzothienyl, benzoisothiazolyl, benzofuranyl, quinolinyl, isoquinolinyl, quinazolinyl, quinoxalinyl, naphthyridinyl, pyrimidinopyridinyl, pyridazinopyridinyl, pyrazinopyridinyl, pyridinopyrimidinyl, pyrimidinopyrimidinyl, pyridazinopyrimidinyl, pyrazinopyrimidinyl, pyridinopyridazinyl, pyrimidinopyridazinyl, pyridazinopyridazinyl, pyrazinopyridazinyl, pyridinopyrazinyl, pyrimidinopyrazinyl, pyridazinopyrazinyl, pyrazinopyrazinyl, pyridinoimidazolyl, purinyl, pyridazinoimidazolyl, pyrazinoimidazolyl, pyridinooxazolyl, pyrimidinooxazolyl, pyridazinooxazolyl, pyrazinooxazolyl, pyridinoisoxazolyl, pyrimidinoisoxazolyl, pyridazinoisoxazolyl, pyrazinoisoxazolyl, pyridinooxathiadiazolyl, pyrimidinooxathiadiazolyl, pyridazinooxathiadiazolyl, pyrazinooxathiadiazolyl, pyridinooxathiazolyl, pyrimidinooxathiazolyl, pyridazinooxathiazolyl, pyrazinooxathiazolyl, pyridinothiazolyl, pyrimidinothiazolyl, pyridazinothiazolyl, pyrazinothiazolyl, pyridinopyrazolyl, pyrimidinopyrazolyl, pyridazinopyrazolyl, pyrazinopyrazolyl, pyridinopyrrolyl, pyrimidinopyrrolyl, pyridazinopyrrolyl, pyrazinopyrrolyl, isobenzofuranyl, indolizinyl, isoindolyl, indolyl, indazolyl, phthalazinyl, cinnolinyl, imidazo[1,2-a]pyridinyl, imidazo[1,2-a]pyridine-2yl, imidazo[1,2-a]pyridine-3yl, isomers thereof and the like.

In a group of embodiments of compounds having formula I, when X is —(C=O)—, $R^3$ is other than —H, alkyl or $R^b$ and subscript n is other than 0.

In one group of embodiments, the compounds have formula Ia:

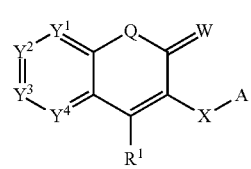

Ia wherein the substituents are as defined above.

In a second group of embodiments, compounds have formula Ib:

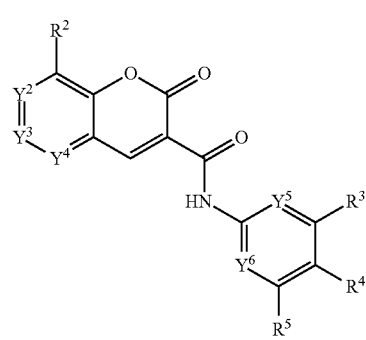

Ib wherein the substituents are as defined above.

In a third group of embodiments, the compounds have formula Ib-1:

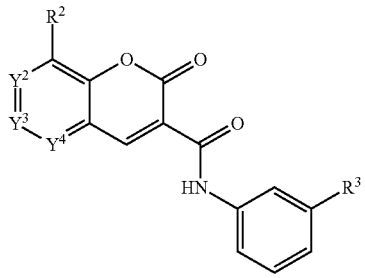

Ib-1 wherein the substituents are as defined above.

In a fourth group of embodiments, the compounds have formula Ib-2:

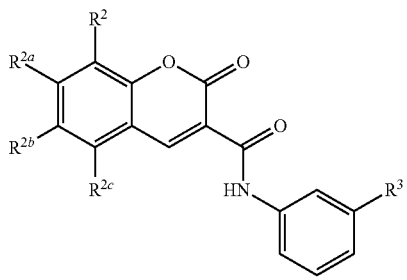

Ib-2 wherein the substituents are as defined above.

In a fifth group of embodiments, the compounds have formula Ib-3:

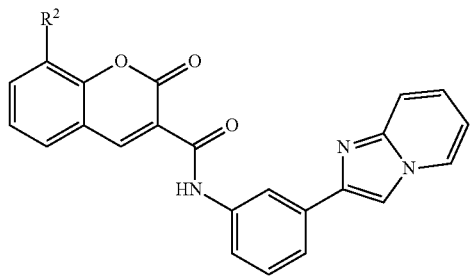

Ib-3 wherein the substituents are as defined above in formula (I). In some embodiments, $R^2$ is selected from —H, —OH, —OMe, —OEt, —F, —Cl, —Br, —OCF$_3$, 4-morpholinyl or

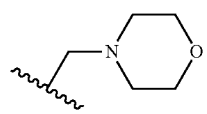

In a sixth group of embodiments, the compounds have formula Ic:

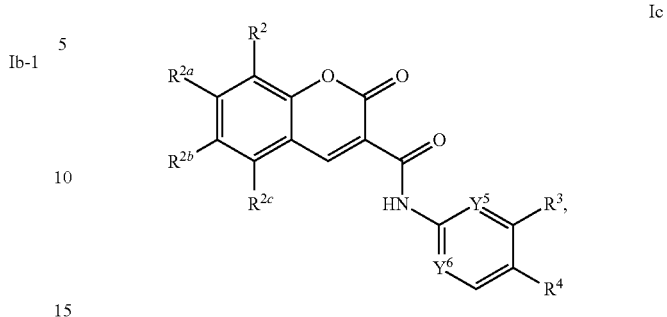

Ic wherein $R^{2a}$, $R^{2b}$ and $R^{2c}$ are as defined in formula (I). In some embodiments, $R^{2a}$, $R^{2b}$ and $R^{2c}$ are each independently —H, —C$_{1-6}$alkyl, —OC$_{1-6}$alkyl, —OH, halo and —NHC$_{1-6}$alkyl, and $Y^5$ and $Y^6$ are as defined above.

In a seventh group of embodiments, the compounds have formula Id:

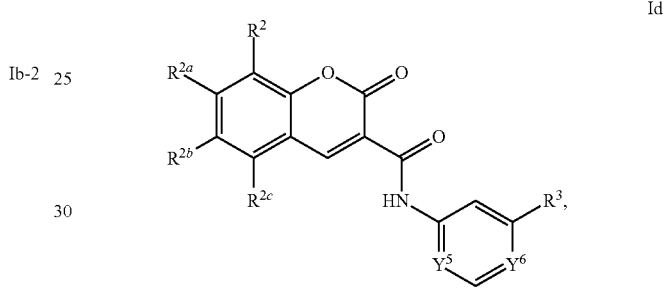

Id wherein $R^{2a}$, $R^{2b}$ and $R^{2c}$ are each independently —H, —C$_{1-6}$alkyl, —OC$_{1-6}$alkyl, —OH, halo or —NHC$_{1-6}$alkyl and $Y^5$, $Y^6$ and $R^3$ are as defined above.

In an eighth group of embodiments, the compounds have formula Id-1:

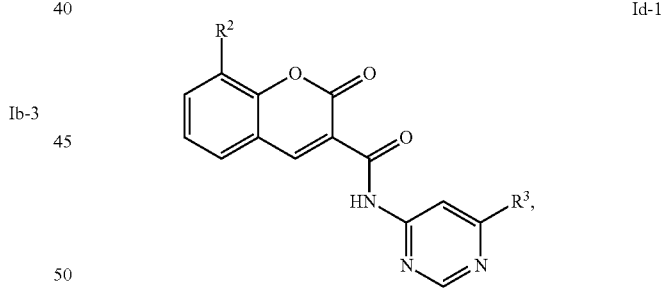

Id-1 wherein $R^2$ and $R^3$ are as defined above in formula I.

In a ninth group of embodiments, the compounds have formula Ie:

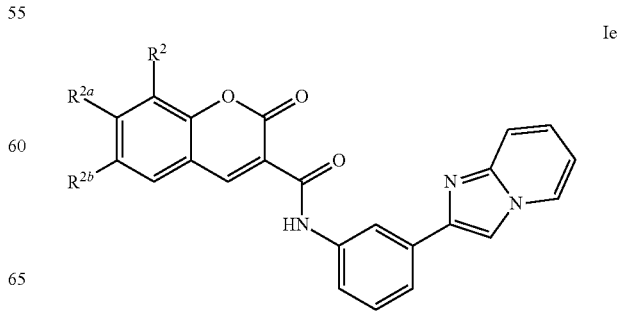

Ie wherein the substituents are as defined above. In some embodiments, R² is selected from the group consisting of hydrogen, —OH, C₁₋₈alkoxy, C₁₋₈haloalkoxy, halogen, heterocycloalkyl and heterocycloalkyl-C₁₋₄alkyl. In certain instances, R² is selected from —H, —OH, —OMe, —OEt, —F, —Cl, —Br, —OCF₃, 4-morpholinyl or

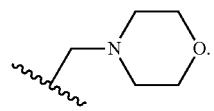

In some embodiments and within the above embodiments, R²ᵃ is hydrogen, halogen, C₁₋₈alkoxy or —OH. In certain instances, R²ᵃ is hydrogen, —OMe, —OH. In some embodiments and within the above embodiments, R²ᵇ is —H, halogen, C₁₋₈. In certain instances, R²ᵇ is —H, Br, —F, —I, —OH, —OMe, or —OCF₃.

In a tenth group of embodiments, the compounds have formula (If):

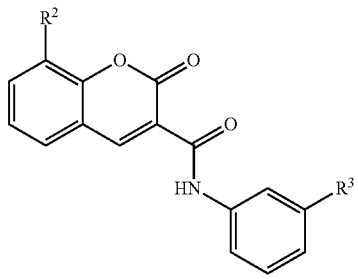

(If)

wherein the substituents R² and R³ are as defined above. In some embodiments, R² is selected from the group consisting of —OH, C₁₋₈alkoxy and C₁₋₈haloalkoxy. In certain instances, R² is —OH, —OMe or —OCF₃. In some embodiments and within the above embodiments, R³ is —H, heterocycloalkyl, heterocycloalkyl-C₁₋₄alkyl, aryl or heteroaryl, wherein the aryl or heteroaryl of the R³ group is optionally substituted with from 1-3 Rᵏ members independently selected from the group consisting of C₁₋₄alkyl, aryl-C₁₋₄alkyl, halo, haloalkyl, —ORᶜ, —SRᶜ, —CN, —NO₂, NRᶜRᵈ, oxo, C₁₋₄alkyl(C=O)NH—, haloalkoxy, —C(=O)C₁₋₄alkyl, OC(=O)C₁₋₄alkyl, —C(=O)ORᶜ, S(O)C₁₋₄alkyl, S(O)₂heterocycloalkyl and S(O)₂C₁₋₄alkyl, or optionally two adjacent Rᵏ substituents together with the atoms to which they are attached form an optionally substituted fused 5- or 6-membered heteroaryl or heterocycloalkyl ring having from 1-2 heteroatoms selected from O or N as ring members, the fused 5- or 6-membered ring is optionally substituted with a Rᵍ; wherein Rᶜ and Rᵈ are each independently selected from the group consisting of —H, C₁₋₆alkyl, —Rᵉ, —NHC₁₋₆alkyl and —NH(C=O)Rᵉ, wherein Rᵉ is a heteroaryl or heterocyclyl having from 1-4 ring heteroatoms selected from O, N or S or an aryl, wherein the aryl or heteroaryl is further optionally substituted with from 1-3 Rᶠ selected from the group consisting of halo, haloalkyl, —OH, —ORᵍ, —SRᵍ, —CN, —NO₂, NRᵍRᵍ, oxo, haloalkoxy, —C(=O)C₁₋₄alkyl, OC(=O)C₁₋₄alkyl, —C(=O)ORᵍ, S(O)C₁₋₄alkyl and S(O)₂ C₁₋₄alkyl, wherein Rᵍ is C₁₋₆alkyl; and wherein each subscript n is independently an integer selected from 0, 1, 2, or 3. In certain instances, the aryl or heteroaryl is optionally substituted with from 1-3 members independently selected from C₁₋₄alkyl, C₁₋₈alkoxy, aryloxy, C₁₋₈haloalkoxy, —CN, C₁₋₈alkyl(C=O)NH—, heterocycloalkyl-SO₂—, C₁₋₈dialkylamino, —OH, halogen, aryl-C₁₋₄alkyl or C₁₋₈alkyl-O—(C=O)—; or two adjacent members of the aryl or heteroaryl substituents together with the atoms to which they are attached form a 5- or 6-membered heterocycloalkyl or heteroaryl ring having from 1-2 heteroatoms selected from O or N as ring members, wherein the heterocyclic ring is optionally substituted with a Rᵍ. In some embodiments, R³ is phenyl optionally substituted with from 1-3 members selected from the group consisting of —H, —OMe, —OEt, —OCF₃, CH₃CONH—, —CN, —OH, —NMe₂,

—F, —F and —Br or optionally the two adjacent members of the aryl or heteroaryl substituents together with the atoms to which they are attached form fused 1,3-dioxolane, tetrahydrofuran, 1,4-dioxane, pyrrole, imidazolidine, isoxazole, oxazole, pyrazole, oxadiazole, 1,2,5-oxadiazole or 4H-pyran-4-one ring.

In an eleventh group of embodiments, the compounds have formula (Ig):

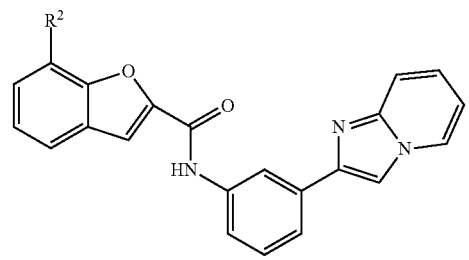

(Ig)

wherein R² is as defined above in formula (I). In some embodiments, R² is C₁₋₈alkoxy.

In a twelfth group of embodiments, the compounds have formula (Ih):

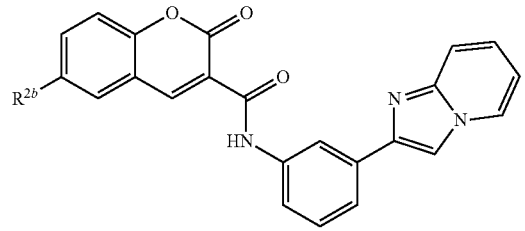

wherein $R^{2b}$ is as defined above in formula (I). In some embodiments, $R^{2b}$ is halogen.

In a thirteenth group of embodiments, the compounds have formula (Ii):

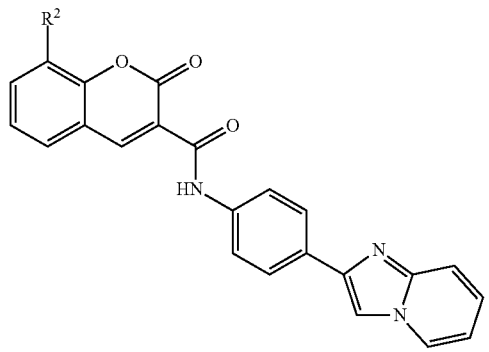

wherein $R^2$ is as defined above in formula (I). In some embodiments, $R^2$ is alkoxy, for example —OMe.

Preparation of Compounds

As shown in the examples below, there are a variety of synthetic routes by which a skilled artisan can prepare compounds and intermediates of the present invention. Schemes I-VII illustrate several methods for the preparation of certain caspase-3 activators of the invention. All the compounds can be made by the methods described in the synthetic schemes. The compounds in Table I can be prepared in accordance with the methods set forth in Schemes I-VII. In each of these schemes, X' is a leaving group, such as a halogen atom; and non-interfering substituents are provided as —R', —R", and —R'''.

The schemes below provide certain synthetic routes that can be followed to access certain caspase-3 activators of the present invention. Other routes or modification of the routes presented below would be readily apparent to a skilled artisan and within the scope of the present invention. All of the starting materials are either commercially available or can be prepared by procedures that would be well known to one of ordinary skill in organic chemistry.

Scheme I

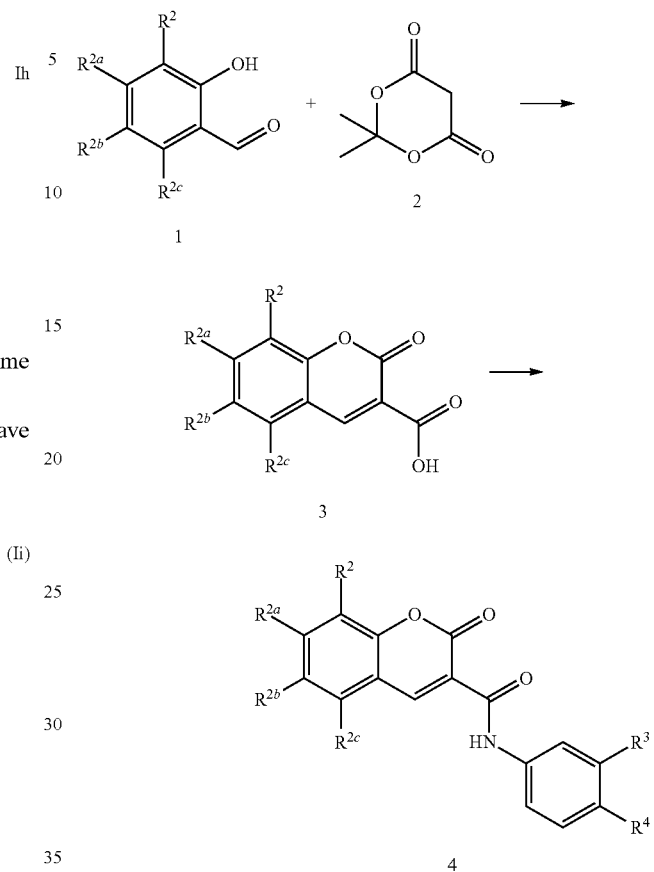

Scheme I illustrates the construction of the 3-carboxycoumarin ring system from substituted salicylaldehydes, a wide variety of which are commercially available. First, the salicylaldehyde (1) is reacted with Meldrum's acid (2) or a related malonate derivative in an organic solvent or in aqueous solution, optionally in the presence of a base such as sodium ethoxide or potassium hydroxide at temperatures between 25-150° C. to afford the 3-carboxycoumarin 3. The reaction may also be carried out under heterogeneous conditions using various inorganic clays as promoters (J. Org. Chem. 1999, 64, 1033-5 and references therein). Favorably the reaction is carried out with Meldrum's acid in water as solvent, with heating at ca. 50-100° C. as described previously (Synth. Commun. 2003, 33, 3299-3303). Next, the carboxylic acid may be converted to various amide derivatives using well-known coupling reactions, including for example conversion to the acid chloride and reaction with amines, or direct coupling of the acid with amines using carbodiimide or other reagents well known to effect acid-amine coupling. The products may be used as collected or may first be purified using conventional techniques such as preparative TLC or HPLC, chromatography, precipitation, crystallization and the like.

Scheme II
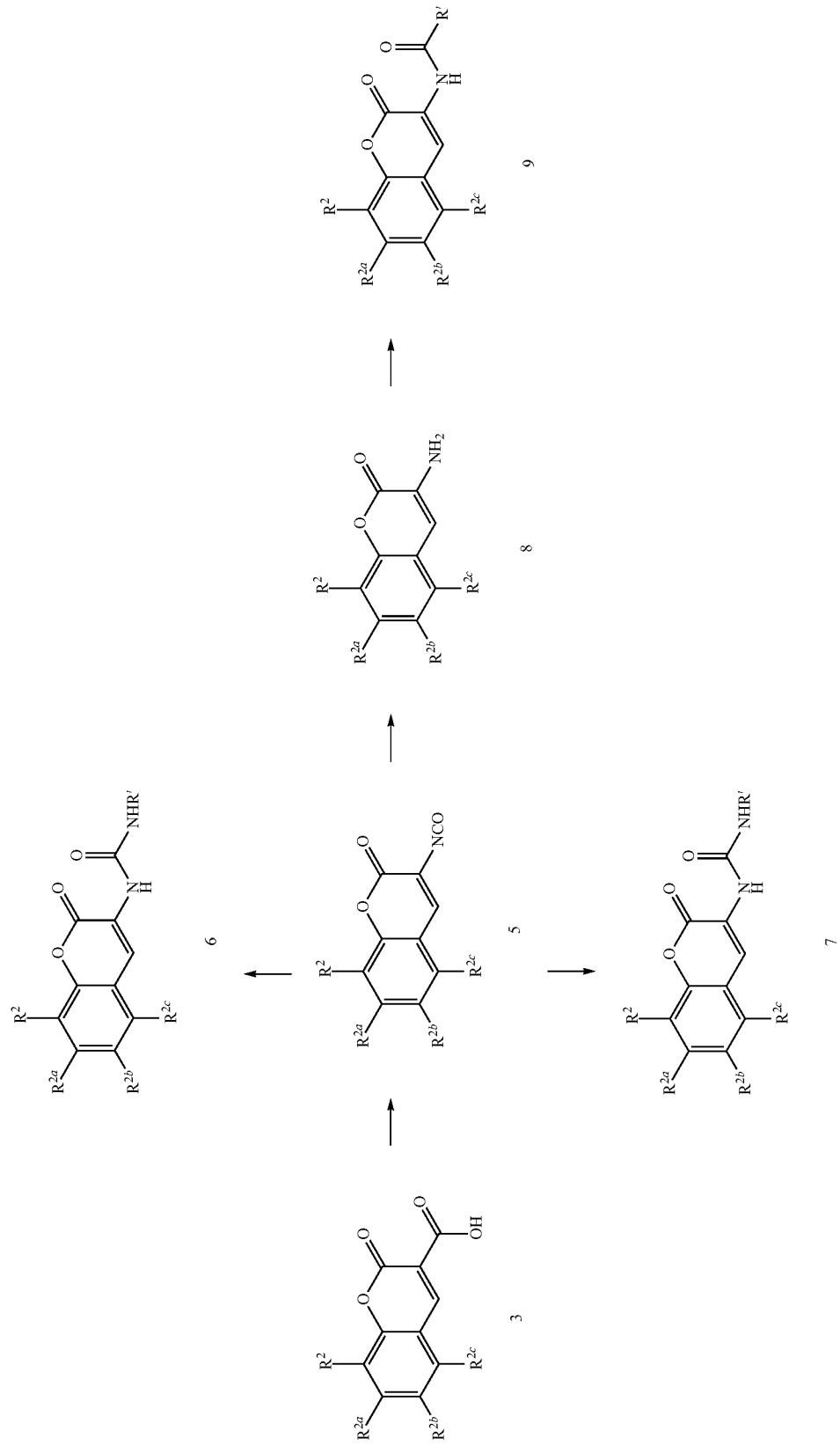

Scheme II illustrates the construction of unique X groups on a compound of formula I. First, the 3-carboxycoumarin (3) ring system is reacted with diphenylphosphoryl azide (DPPA) or sodium azide in an organic solvent in the presence of base, such as triethylamine, at temperatures between 25-100° C. This reaction forms an acyl azide derivative that decomposes to an isocyanate (5). Favorably, the reaction is carried out with DPPA, triethylamine, and benzene as the solvent with heating ca. 70-100° C. as described previously (*Tetrahedron* 2005, 61, 3637-3649). Next, the isocyanate (5) may be converted to various carbamate (6), urea (7), and amide (9) derivatives using well-known reactions. The isocyanate (5) is converted to a carbamate (6) analog by reaction in organic solvent with alcohols or phenols. A urea (7) analog is formed through reaction with substituted amines or anilines. Finally, amines or anilines (8) are formed from the isocyanate (5) by hydrolysis, and can be further derivatized through standard coupling conditions presented in scheme I to form amide (9) linkages using commercially available carboxylic acids. The products may be used as collected or may first be purified using conventional techniques such as preparative TLC or HPLC, chromatography, precipitation, crystallization and the like.

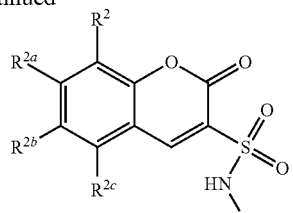

13

Scheme III illustrates the construction of sulfonyl chloride substituted coumarin rings, which can be reacted with commercially available anilines or amines to form sulfonamide linkage (where X=—SO$_2$NH—) in a compound of formula I. First, the 3-aminocoumarin (8) ring is reacted with nitrous acid (formed from sodium nitrite and a strong acid) in water at temperatures between −20-25° C., as already described (*Bioorg. Med. Chem.* 2002, 10, 31-40). This leads to the formation of a diazonium salt (10). The 3-diazonium-coumarin (10) then undergoes a Leukart thiophenol reaction in the presence of potassium alkyl xanthate to form the coumarin substituted xanthate. Under basic conditions the xanthate forms the free thiol at the 3-position of the coumarin ring. Next, the 3-thiocoumarin (11) is reacted with N-chlorosuccinimide under acidic conditions in organic solvent at temperatures ranging from 0-50° C. Under these conditions, the sulfonyl chloride functional group (12) is formed as previously described (*Synthesis* 2006, 24, 4131-4134). Once formed the sulfonyl chloride can be reacted with commercially available anilines and amines using standard coupling conditions presented in scheme I to form the sulfonamide derivative (13). The products may first be purified using conventional techniques such as preparative TLC or HPLC, chromatography, precipitation, crystallization and the like.

Scheme III

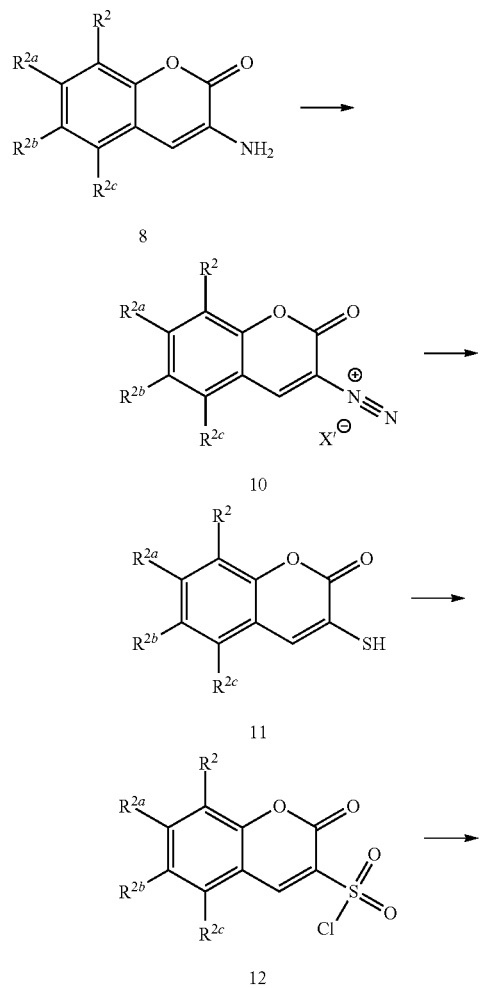

Scheme IV

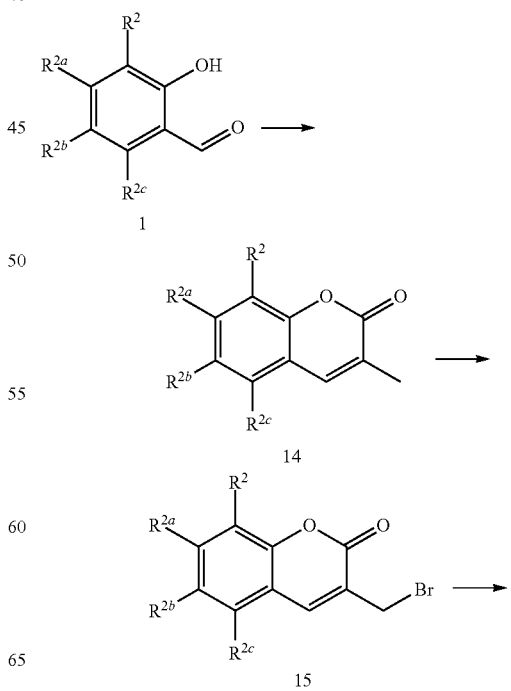

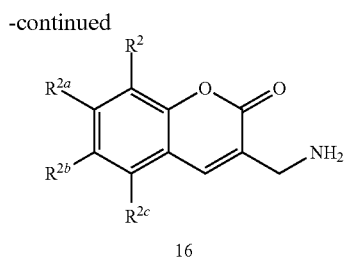

16

Scheme IV describes the formation of additional X linkage in a compound of formula I. Commercially available salicylaldehydes (1) can again be used to now form methylated coumarins at the 3-position. First, the salicylaldehyde (1) undergoes a standard Wittig reaction with $Ph_3P=CCH_3COOMe$ in organic solvent at temperatures ranging from 10-50° C. The reaction mixture is subsequently heated in organic solvent to promote ring cyclization to the 3-methylcoumarin (14). These optimal conditions for the formation of the methylated coumarin have been previously described (*Journal of Medicinal Chemistry* 1999, 42, 2662-2672). The coumarin compound is next treated with N-bromosuccinimide in anhydrous organic solvent at temperatures ranging from 50-100° C. This forms the 3-bromomethylcoumarin (15), as illustrated previously (*Journal of Medicinal Chemistry* 2004, 47, 756-760). Finally, the bromomethylcoumarin is reacted with hexanemethylenetetramine in organic solvent under reflux conditions. The solvent is subsequently removed and the residue is hydrolyzed under acidic conditions to form the primary amine (16). The optimal conditions for the hydrolysis are reflux in ethanol with concentrated hydrochloric acid, as already reported (*Journal of Medicinal Chemistry* 2004, 47, 756-760). Finally, the resulting amine can be reacted with commercially available carboxylic acids using standard coupling conditions described in scheme I. The products may be used as collected or may first be purified using conventional techniques such as preparative TLC or HPLC, chromatography, precipitation, crystallization and the like.

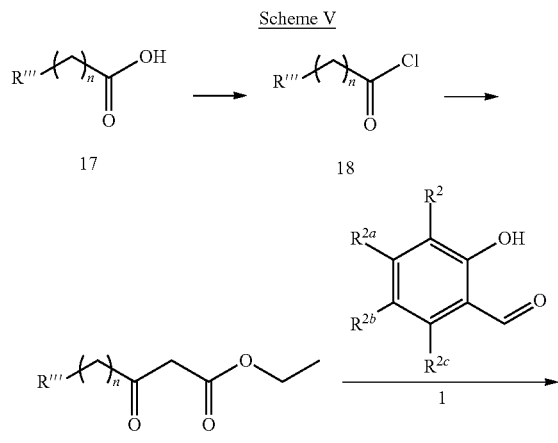

Scheme V illustrates additional modifications to linkage group X in a compound of formula I. Commercially available carboxylic acids (17) are treated with neat thionyl chloride under reflux conditions to yield acyl chlorides (18). Once formed the acyl chlorides are reacted with Meldrum's acid (2) in an organic solvent, in the presence of a base such as pyridine at temperatures ranging from 0-50° C. The crude reaction mixture is then decarboxylated by refluxing in ethanol to form the β-ketoester (19). Finally, condensation of commercially available salicylaldehydes (1) with the β-ketoester (19) in organic solvents under reflux conditions results in coumarin derivatives with ketone functionalities at the 3-position (20), as previously shown (*Journal of Medicinal Chemistry* 2005, 48, 7592-7603). The products may be used as collected or may first be purified using conventional techniques such as preparative TLC or HPLC, chromatography, precipitation, crystallization and the like.

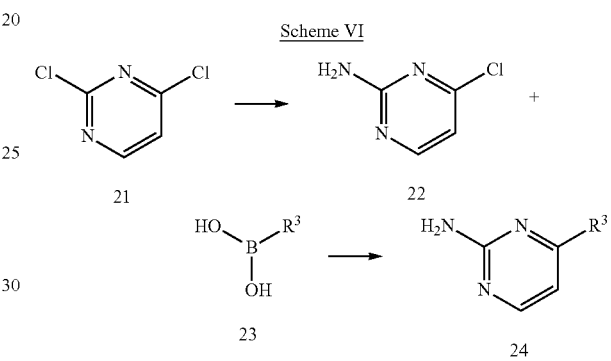

Scheme VI illustrates formation of amino heterocycles, such as 2-amino pyrimidines and derivatives to be used in reactions with precursors of compounds of formula I described above. First, ammonium hydroxide is slowly added at reduced temperatures (−20-10° C.) to 2,4-dichloropyrimidine (21) in organic solvent to form 2-amino-4-chloropyrimidine (22), as previously described (*Journal of Medicinal Chemistry* 2005, 48, 5570-5579). Next, the chloropyrimidine undergoes a Suzuki coupling reaction with commercially available boronic acids (23) in the presence of base and a palladium catalyst in aqueous and/or organic solvents at temperatures ranging from 20-120° C. Favorable reaction conditions that have been described include the use of the base $K_2CO_3$ and tetrakis(triphenylphosphine)palladium in DMF (*Tetrahedron* 2001, 57, 2787-9; *Bioorg Med Chem Lett* 2005, 15(16), 3670-4; *Bioorg Med Chem Lett* 2005, 15(16), 3675-8). The products may be used as collected or may first be purified using conventional techniques such as preparative TLC or HPLC, chromatography, precipitation, crystallization and the like. 2-aminopyrimidines (24) formed can be used in coupling reactions described in schemes I, II, and III.

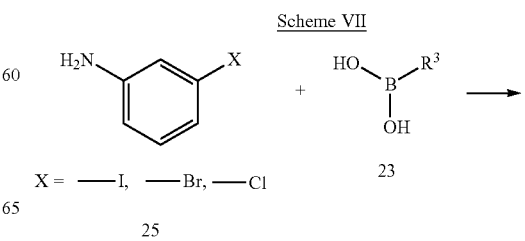

-continued

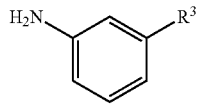

Scheme VII illustrates another method for the formation of novel aniline small molecules (26) that can also be using in the formation of compounds from schemes I, II, and III. Commercially available halogenated anilines (25) can be used in Suzuki reactions with commercially available boronic acids (23) described above. Again, conditions for the Suzuki coupling include the use of base and a palladium catalyst in aqueous and/or organic solvents. The products may be used as collected or may first be purified using conventional techniques such as preparative TLC or HPLC, chromatography, precipitation, crystallization and the like.

IV. Pharmaceutical Composition

In accordance with the present invention, a therapeutically effective amount of a compound of formulas I', I, Ia, Ib, Ib-1, Ib-2, Ib-3, Ic, Id, Id-1, Ie, If, Ig, Ih or Ii can be used for the preparation of a pharmaceutical composition useful for treating neoplastic diseases in a mammal.

The compositions of the invention can include compounds of Formulas I', I, Ia, Ib, Ib-1, Ib-2, Ib-3, Ic, Id, Id-1, Ie, If, Ig, Ih and Ii or pharmaceutically acceptable salts thereof, a hydrate thereof or a hydrolysable precursor thereof. In general, the compound is mixed with suitable carriers or excipient(s) in a therapeutically effective amount. By a "therapeutically effective dose", "therapeutically effective amount" or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of neoplastic diseases.

The compounds of Formulas I', I, Ia, Ib, Ib-1, Ib-2, Ib-3, Ic, Id, Id-1, Ie, If, Ig, Ih or Ii that are used in the methods of the present invention can be incorporated into a variety of formulations for therapeutic administration. More particularly, the compounds of Formulas I', I, Ia, Ib, Ib-1, Ib-2, Ib-3, Ic, Id, Id-1, Ie, If, Ig, Ih, Ii can be formulated into pharmaceutical compositions by combination with appropriate, pharmaceutically acceptable carriers or diluents and can be formulated into preparations in solid, semi-solid, liquid or gaseous forms, such as tablets, capsules, pills, powders, granules, dragees, suspensions, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local manner, in a depot or sustained release formulation. In addition, the compounds can be administered in a liposome.

The compounds of Formulas I', I, Ia, Ib, Ib-1, Ib-2, Ib-3, Ic, Id, Id-1, Ie, If, Ig, Ih, or Ii can be formulated with common excipients, diluents or carriers and compressed into tablets or formulated as elixirs or solutions for convenient oral administration or administered by intramuscular or intravenous routes. The compounds can be administered transdermally and can be formulated as sustained release dosage forms and the like. Compounds of Formula (I) can be administered alone, in combination with each other or they can be used in combination with other known compounds.

Suitable formulations for use in the present invention are found in *Remington: The Science and Practice of Pharmacy*, 21st ed., Lippincott Williams & Wilkins, Philadelphia, Pa., 2005, which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing compound of formula I may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

Dragee cores are provided with suitable coatings. For this purpose, concentrated sugar solutions can be used, which can optionally contain gum arabic, talc, polyvinyl pyrrolidone, carbopol gel, polyethylene glycol and/or titanium dioxide, lacquer solutions and suitable organic solvents or solvent mixtures. Dyestuffs or pigments can be added to the tablets or dragee coatings for identification or to characterize different combinations of active compound doses.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Alternatively, other deliveries for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

The compounds of this invention may also be coupled with a carrier that is a suitable polymer as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

Certain organic solvents such as dimethylsulfoxide (DMSO) also can be employed, although usually at the cost of greater toxicity. Additionally, the compounds can be delivered using a sustained-release, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics*, Ch. 1).

V. Methods of Activating Executioner Procaspases and Treating Disease States

In another aspect, the present invention provides a method of activating procaspases, e.g., executioner procaspase 3, 6 and/or 7. The method includes/comprising contacting a compound of formula I or a pharmaceutical composition thereof with a procaspase, e.g., executioner procaspase 3, 6 and/or 7. Disease states the respond to procaspase activation can be prevented or the severity of the disease can be reduced or the time course of the disease reduced by administering the compounds of the present invention.

Typically, executioner procaspase 3 and/or 6 undergo self-activation once contacted by a compound of formula I. In certain instances, executioner procaspase 7 can undergo self-activation at a higher concentration when contacted by a compound of formula I.

In yet another aspect, the present invention also provides a method for treating diseases in a mammal, e.g., neoplastic diseases and cancer. The method includes administering to the mammal a therapeutically effective amount of a compound of formula I or a pharmaceutically acceptable salt thereof. Diseases treatable by this method include disease states where the diseased cell is to be eliminated, such as autoimmune diseases, infectious disease, cancer and neoplastic disease.

In one embodiment of the invention, the compounds of the invention can be used for the treatment of diseases selected from the group consisting of leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, brain, head or neck cancer, cancer in the urinary tract, kidney or bladder cancer, malignant melanoma, liver cancer, uterine or pancreatic cancer, colon cancer, thyroid cancer, bowel cancer and pancreas cancer.

Treatment methods provided herein include, in general, administration to a patient an effective amount of one or more compounds provided herein, e.g., orally, nasally or parenterally. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound, one or more compounds provided herein, for example, compounds of formula I. In a preferred embodiment, the compound(s) of the invention are preferably administered to a patient (e.g., a human) orally. The effective amount may be an amount sufficient to activate executioner procaspase 3, 6 and/or 7 activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably activate executioner procaspase 3, 6 and/or 7. Treatment regimens may vary depending on the compound used and the particular condition to be treated; for treatment of most disorders, a frequency of administration of 4 times daily or less is preferred. In general, a dosage regimen of twice daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

The compounds of the present invention can be administered as frequently as necessary, including hourly, daily, weekly or monthly. Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. The compounds utilized in the pharmaceutical method of the invention are administered at the initial dosage of about 0.0001 mg/kg to about 3000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. It will be understood, however, that the specific dose level for any particular patient will depend upon a variety of factors including the activity of the specific compound employed, the age, body weight, general health, sex, diet, time of administration, route of administration, rate of excretion, drug combination (i.e., other drugs being administered to the patient), the severity of the particular disease undergoing therapy, and other factors, including the judgment of the prescribing medical practitioner. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

The time-release effect can be obtained by capsule materials that dissolve at different pH values, by capsules that release slowly by osmotic pressure or by any other known means of controlled release.

It can be necessary to use dosages outside these ranges in some cases as will be apparent to those skilled in the art. Further, it is noted that the clinician or treating physician will know how and when to interrupt, adjust or terminate therapy in conjunction with individual patient response.

In some embodiments, the present invention provides a compound of formulas I', I, Ia, Ib, Ib-1, Ib-2, Ib-3, Ic, Id, Id-1, Ie, If, Ig, Ih, Ii or a pharmaceutically acceptable salt thereof, as defined in any one of claims 1 to 15, for use as a medicament.

In other embodiments, the present invention provides a compound of formulas I', I, Ia, Ib, Ib-1, Ib-2, Ib-3, Ic, Id, Id-1, Ie, If, Ig, Ih, Ii, or a pharmaceutically acceptable salt thereof, according to any one of claims 1 to 15, for use in the treatment of a neoplastic disease or a cancer. The treatable diseases include leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, brain, head or neck cancer, cancer in the urinary tract, kidney or bladder cancer, malignant melanoma, liver cancer, uterine or pancreatic cancer, colon cancer, thyroid cancer, bowel cancer and pancreas cancer. Plus basis for a dependent claim to pain types.

In some embodiments, the present invention provides use of a compound of formula I', I, Ia, Ib, Ib-1, Ib-2, Ib-3, Ic, Id, Id-1, Ie, If, Ig, Ih, Ii, or a pharmaceutically acceptable salt thereof, according to any one of claims 1 to 15, in the manufacture of a medicament for the treatment of a neoplastic disease or a cancer. The treatable diseases include leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, brain, head or neck cancer, cancer in the urinary tract, kidney or bladder cancer, malignant melanoma, liver cancer, uterine or pancreatic cancer, colon cancer, thyroid cancer, bowel cancer and pancreas cancer. Plus basis for a dependent claim to pain types.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

The compounds of formula I can also be administered in combination with additional therapeutic agents, or diagnostic agents.

VI. EXAMPLES

Example 1

Synthesis of 8-Methoxy-2-oxo-2H-chromene-3-carboxylic acid (3-imidazo[1,2-a]pyridin-2-yl-phenyl)-amide (1541)

Diisopropylethylamine (DIEA, 0.044 mL, 0.25 mmol) was added to 8-methoxy-3-carboxy-coumarin (0.05 g, 0.23 mmol) and O-(7-Azabenzotriazole-1-yl)-N,N,N,N'-tetramethyluronium hexafluorophosphate (HATU, 0.096 g, 0.25 mmol) in 2 mL of dimethylformamide (DMF) with constant stirring at room temperature until a clear solution resulted. Subsequently, 3-Imidazo[1,2-a]pyridin-2-yl-phenylamine (0.048 g, 0.023 mmol) was added and allowed to react for approximately 30 minutes, when a yellow solid precipitated out of solution. The precipitate was filtered and dried under suction and then in vacuo to give 1541: $^1$H NMR (400 MHz, DMSO-$d_6$) δ 10.78 (s, 1H), 8.92 (s, 1H), 8.54 (d, J=7.0 Hz, 1H), 8.44 (s, 1H), 8.31 (s, 1H), 7.73 (m, 2H), 7.60 (d, J=9.0 Hz, 1H), 7.57 (d, J=9.0 Hz, 1H), 7.44 (m, 3H), 7.26 (dd, J=5.5, 6.8 Hz, 1H), 6.90 (dd, J=5.5, 6.8 Hz, 1H), 3.96 (s, 3H); LCMS (ESI) m/z 412 (MH$^+$).

Example 2

Synthesis of 8-Hydroxy-2-oxo-2H-chromene-3-carboxylic acid (3-imidazo[1,2-a]pyridin-2-yl-phenyl)-amide (1541A)

2,3-dihydroxybenzaldehyde (0.096 g, 0.69 mmol) and Meldrum's acid (0.100 g, 0.69 mmol) were combined in $H_2O$ (1 mL). The solution was stirred at 75° C. for 2 h. After cooling to room temperature, the precipitate was filtered and dried at suction to give 0.123 g of 8-hydroxy-3-carboxy-coumarin in an 85% yield: LCMS (ESI) m/z 207 ($MH^+$).

DIEA (0.046 mL, 0.27 mmol) was added to 8-hydroxy-3-carboxy-coumarin (0.050 g, 0.24 mmol) and HATU (0.101 g, 0.27 mmol) in 1 mL of dimethylformamide (DMF) with constant stirring at room temperature until a clear solution resulted. Subsequently, 3-imidazo[1,2-a]pyridin-2-yl-phenylamine (0.051 g, 0.24 mmol) was added and allowed to react overnight, when a yellow solid precipitated out of solution. The precipitate was filtered and dried under suction and then in vacuo to give 0.021 g of 1541A in a 22% yield: LCMS (ESI) m/z 398 ($MH^+$).

Example 3

Synthesis of 2-Oxo-8-trifluoromethoxy-2H-chromene-3-carboxylic acid (3-imidazo[1,2-a]pyridin-2-yl-phenyl)-amide (1541B)

3-(Trifluoromethoxy)salicylaldehyde (0.250 g, 1.21 mmol) and Meldrum's acid (0.200 g, 1.39 mmol) were combined in $H_2O$ (2 mL). The solution was stirred at 75° C. for 2 h. After cooling to room temperature, the precipitate was filtered and dried at suction to give 0.197 g of 8-(trifluoromethoxy)-3-carboxy-coumarin in a 60% yield: LCMS (ESI) m/z 275 ($MH^+$).

DIEA (0.035 mL, 0.20 mmol) was added to 8-(trifluoromethoxy)-3-carboxy-coumarin (0.050 g, 0.18 mmol) and HATU (0.076 g, 0.20 mmol) in 1 mL of dimethylformamide (DMF) with constant stirring at room temperature until a clear solution resulted. Subsequently, 3-imidazo[1,2-a]pyridin-2-yl-phenylamine (0.038 g, 0.18 mmol) was added and allowed to react overnight, when a yellow solid precipitated out of solution. The precipitate was filtered and dried under suction and then in vacuo to give 0.039 g of 1541B in a 46% yield: LCMS (ESI) m/z 466 ($MH^+$).

Example 4

Synthesis of 7-Methoxy-2-oxo-2H-chromene-3-carboxylic acid (3-imidazo[1,2-a]pyridin-2-yl-phenyl)-amide (1541C)

DIEA (0.027 mL, 0.16 mmol) was added to 7-methoxy-3-carboxy-coumarin (0.031 g, 0.14 mmol) and HATU (0.060 g, 0.16 mmol) in 2 mL of dimethylformamide (DMF) with constant stirring at room temperature until a clear solution resulted. Subsequently, 3-Imidazo[1,2-a]pyridin-2-yl-phenylamine (0.030 g, 0.14 mmol) was added and allowed to react for approximately 30 minutes, when a yellow solid precipitated out of solution. The precipitate was filtered and dried under suction and then in vacuo to give 0.051 g of 1541C in an 86% yield: $^1$H NMR (400 MHz, $CD_3OD/CDCl_3$) δ 10.95 (s, 1H), 8.96 (s, 1H), 8.23 (dd, J=1.8, 1.9 Hz, 1H), 8.20 (d, J=7.1 Hz, 1H), 7.99 (s, 1H), 7.79 (d, J=7.7 Hz, 1H), 7.75 (d, J=8.1 Hz, 1H), 7.68 (d, J=8.6 Hz, 1H), 7.63 (d, J=9.1 Hz, 1H), 7.48 (dd, J=7.9, 8.0 Hz, 1H), 7.25 (dd, J=5.5, 6.8 Hz, 1H), 7.01 (dd, J=2.4, 8.8 Hz, 1H), 6.95 (d, J=2.4 Hz, 1H), 6.85 (dd, J=7.0, 7.3 Hz, 1H), 3.96 (s, 3H); LCMS (ESI) m/z 412 ($MH^+$).

Example 5

Synthesis of 6-Methoxy-8-morpholin-4-ylmethyl-2-oxo-2H-chromene-3-carboxylic acid (3-imidazo[1,2-a]pyridin-2-yl-phenyl)-amide (1541D)

2-hydroxy-5-methoxy-3-(4-morpholinylmethyl)benzaldehyde (0.349 g, 1.39 mmol) and Meldrum's acid (0.200 g, 1.39 mmol) were combined in $H_2O$ (2 mL). The solution was stirred at 75° C. for 2 h. After cooling to room temperature, the precipitate was filtered and dried at suction to give 0.381 g of 8-(4-morpholinylmethyl)-3-carboxy-6-methoxy-coumarin in an 85% yield: LCMS (ESI) m/z 320 ($MH^+$).

DIEA (0.030 mL, 0.17 mmol) was added to 8-(4-morpholinylmethyl)-3-carboxy-6-methoxy-coumarin (0.050 g, 0.16 mmol) and HATU (0.065 g, 0.17 mmol) in 1 mL of dimethylformamide (DMF) with constant stirring at room temperature until a clear solution resulted. Subsequently, 3-imidazo[1,2-a]pyridin-2-yl-phenylamine (0.033 g, 0.16 mmol) was added and allowed to react overnight, when a yellow solid precipitated out of solution. The precipitate was filtered and dried under suction and then in vacuo to give 0.047 g of 1541D in a 59% yield: LCMS (ESI) m/z 511 ($MH^+$).

Example 6

Synthesis of 8-Methoxy-2-oxo-2H-chromene-3-carboxylic acid pyrimidin-4-ylamide (1541E)

DIEA (0.044 mL, 0.25 mmol) was added to 8-methoxy-3-carboxy-coumarin (0.030 g, 0.14 mmol) and HATU (0.095 g, 0.25 mmol) in 1 mL of dimethylformamide (DMF) with constant stirring at room temperature until a clear solution resulted. Subsequently, pyrimidin-4-ylamine (0.009 g, 0.09 mmol) was added and allowed to react overnight, when a solid precipitated out of solution. The precipitate was filtered and dried under suction and then in vacuo to give 0.003 g of 1541E in an 11% yield: LCMS (ESI) m/z 298 ($MH^+$).

Example 7

Synthesis of 8-Methoxy-2-oxo-2H-chromene-3-carboxylic acid [3-(1H-benzoimidazol-2-yl)-phenyl]-amide (1541F)

DIEA (0.044 mL, 0.25 mmol) was added to 8-methoxy-3-carboxy-coumarin (0.050 g, 0.23 mmol) and HATU (0.095 g, 0.25 mmol) in 2 mL of dimethylformamide (DMF) with constant stirring at room temperature until a clear solution resulted. Subsequently, 3-(1H-benzimidazol-2-yl)-benzenamine (0.048 g, 0.23 mmol) was added and allowed to react overnight, when a yellow solid precipitated out of solution. The precipitate was filtered and dried under suction and then in vacuo to give 1541F: LCMS (ESI) m/z 412 ($MH^+$).

Example 8

Synthesis of 8-Methoxy-2-oxo-2H-chromene-3-carboxylic acid (4-imidazo[1,2-a]pyridin-2-yl-phenyl)-amide (1541 G)

DIEA (0.044 mL, 0.25 mmol) was added to 8-methoxy-3-carboxy-coumarin (0.050 g, 0.23 mmol) and HATU (0.095 g, 0.25 mmol) in 1 mL of dimethylformamide (DMF) with constant stirring at room temperature until a clear solution resulted. Subsequently, 4-Imidazo[1,2-a]pyridin-2-yl-phenylamine (0.048 g, 0.23 mmol) was added and allowed to react overnight, when a yellow solid precipitated out of solution. The precipitate was filtered and dried under suction and then in vacuo to give 0.071 g of 1541G in a 76% yield: LCMS (ESI) m/z 412 (MH$^+$).

Example 9

Synthesis of 8-Methoxy-2-oxo-2H-chromene-3-carboxylic acid phenylamide (1541H)

DIEA (0.044 mL, 0.25 mmol) was added to 7-methoxy-3-carboxy-coumarin (0.050 g, 0.23 mmol) and HATU (0.095 g, 0.25 mmol) in 1 mL of dimethylformamide (DMF) with constant stirring at room temperature until a clear solution resulted. Subsequently, aniline (0.021 g, 0.23 mmol) was added and allowed to react overnight, when a yellow solid precipitated out of solution. The precipitate was filtered and dried under suction and then in vacuo to give 0.055 g of 1541H in an 82% yield: LCMS (ESI) m/z 296 (MH$^+$).

Example 10

Synthesis of 8-Methoxy-2-oxo-2H-chromene-3-carboxylic acid (3-morpholin-4-yl-phenyl)-amide (1541I)

DIEA (0.044 mL, 0.25 mmol) was added to 8-methoxy-3-carboxy-coumarin (0.050 g, 0.23 mmol) and HATU (0.095 g, 0.25 mmol) in 1 mL of dimethylformamide (DMF) with constant stirring at room temperature until a clear solution resulted. Subsequently, 3-morpholin-4-yl-phenylamine (0.040 g, 0.23 mmol) was added and allowed to react overnight, when a yellow solid precipitated out of solution. The precipitate was filtered and dried under suction and then in vacuo to give 0.066 g of 1541I in a 76% yield: LCMS (ESI) m/z 381 (MH$^+$).

Example 11

Synthesis of 6-Bromo-2-oxo-2H-chromene-3-carboxylic acid (3-imidazo[1,2-a]pyridin-2-yl-phenyl)-amide (1)

DIEA (35.6 µL, 0.2 mmol) was added to 6-bromo-3-carboxy-coumarin (50.0 mg, 0.19 mmol) and HATU (77.7 mg, 0.2 mmol) in 2 mL of DMF with constant stirring at room temperature until a clear solution resulted. Subsequently, 3-Imidazo[1,2-a]pyridin-2-yl-phenylamine (38.9 mg, 0.19 mmol) was added and allowed to react overnight when a solid precipitated out of solution. The resulting precipitate was filtered, dried under suction, and finally dried overnight in vacuo to give 61.4 mg of product in 68% yield: LCMS (ESI) m/z 461 (MH$^+$).

Example 12

Synthesis of 8-Fluoro-2-oxo-2H-chromene-3-carboxylic acid (3-imidazo[1,2-a]pyridin-2-yl-phenyl)-amide (2)

3-Fluorosalicylaldehyde (97.2 mg, 0.69 mmol) and Meldrum's acid (100 mg, 0.69 mmol) were combined in H$_2$O (1 mL). The solution was stirred at 75° C. for 2 h. After cooling to room temperature, the precipitate was filtered and dried at suction to give 99.6 mg of 8-fluoro-3-carboxy-coumarin in a 68% yield.

DIEA (46.0 µL, 0.26 mmol) was added to 8-fluoro-3-carboxy-coumarin (50.3 mg, 0.24 mmol) and HATU (100.5 mg, 0.26 mmol) in 2 mL of DMF with constant stirring at room temperature until a clear solution resulted. Subsequently, 3-Imidazo[1,2-a]pyridin-2-yl-phenylamine (50.0 mg, 0.24 mmol) was added and allowed to react overnight when a solid precipitated out of solution. The resulting precipitate was filtered, dried under suction, and finally dried overnight in vacuo for final product: LCMS (ESI) m/z 400 (MH$^+$).

Example 13

Synthesis of 7,8-Dihydroxy-2-oxo-2H-chromene-3-carboxylic acid (3-imidazo[1,2-a]pyridin-2-yl-phenyl)-amide (3)

2,3,4-trihydroxybenzaldehyde (106.7 mg, 0.69 mmol) and Meldrum's acid (100 mg, 0.69 mmol) were combined in H$_2$O (1 mL). The solution was stirred at 75° C. for 2 h. After cooling to room temperature, the precipitate was filtered and dried at suction to give 114.1 mg of 7,8-dihydroxy-3-carboxy-coumarin in a 74% yield.

DIEA (43.1 µL, 0.25 mmol) was added to 7,8-dihydroxy-3-carboxy-coumarin (50 mg, 0.23 mmol) and HATU (94.1 mg, 0.25 mmol) in 2 mL of DMF with constant stirring at room temperature until a clear solution resulted. Subsequently, 3-Imidazo[1,2-a]pyridin-2-yl-phenylamine (47.1 mg, 0.23 mmol) was added and allowed to react overnight when a solid precipitated out of solution. The resulting precipitate was filtered, dried under suction, and finally dried overnight in vacuo for final product: LCMS (ESI) m/z 414 (MH$^+$).

Example 14

Synthesis of 8-Bromo-2-oxo-2H-chromene-3-carboxylic acid (3-imidazo[1,2-a]pyridin-2-yl-phenyl)-amide (4)

3-bromohydroxybenzaldehyde (139.5 mg, 0.69 mmol) and Meldrum's acid (100 mg, 0.69 mmol) were combined in H$_2$O (1 mL). The solution was stirred at 75° C. for 2 h. After cooling to room temperature, the precipitate was filtered and dried at suction to give 135.0 mg of 8-bromo-3-carboxy-coumarin in an 73% yield.

DIEA (35.6 µL, 0.2 mmol) was added to 8-bromo-3-carboxy-coumarin (50 mg, 0.19 mmol) and HATU (77.73 mg, 0.2 mmol) in 1 mL of DMF with constant stirring at room temperature until a clear solution resulted. Subsequently, 3-Imidazo[1,2-a]pyridin-2-yl-phenylamine (38.89 mg, 0.19 mmol) was added and allowed to react overnight when a solid precipitated out of solution. The resulting precipitate was filtered, dried under suction, and finally dried overnight in vacuo to the final product: LCMS (ESI) m/z 461 (MH$^+$).

Example 15

Synthesis of 8-Ethoxy-2-oxo-2H-chromene-3-carboxylic acid (3-imidazo[1,2-a]pyridin-2-yl-phenyl)-amide (5)

3-ethoxy-salicylaldehyde (115.3 mg, 0.69 mmol) and Meldrum's acid (100 mg, 0.69 mmol) were combined in H$_2$O (1 mL). The solution was stirred at 75° C. for 2 h. After cooling to room temperature, the precipitate was filtered and dried at suction.

DIEA (40.9 µL, 0.23 mmol) was added to 8-ethoxy-3-carboxy-coumarin (50.0 mg, 0.21 mmol) and HATU (89.29 mg, 0.23 mmol) in 1 mL of DMF with constant stirring at room temperature until a clear solution resulted. Subsequently, 3-Imidazo[1,2-a]pyridin-2-yl-phenylamine (44.7 mg, 0.21 mmol) was added and allowed to react overnight when a solid precipitated out of solution. The resulting precipitate was filtered, dried under suction, and finally dried overnight in vacuo to give 37.4 mg of product in 42% yield: LCMS (ESI) m/z 426 (MH$^+$).

Example 16

Synthesis of 6-Methoxy-2-oxo-2H-chromene-3-carboxylic acid (3-imidazo[1,2-a]pyridin-2-yl-phenyl)-amide (6)

5-methoxy-salicylaldehyde (211.1 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 241.1 mg of 6-methoxy-3-carboxy-coumarin in a 79% yield.

DIEA (43.5 µL, 0.25 mmol) was added to 6-methoxy-3-carboxy-coumarin (50.0 mg, 0.23 mmol) and HATU (95.0 mg, 0.25 mmol) in 1 mL of DMF with constant stirring at room temperature until a clear solution resulted. Subsequently, 3-Imidazo[1,2-a]pyridin-2-yl-phenylamine (47.5 mg, 0.23 mmol) was added and allowed to react overnight when a solid precipitated out of solution. The resulting precipitate was filtered, dried under suction, and finally dried overnight in vacuo to give 78.5 mg of product in 83% yield: LCMS (ESI) m/z 412 (MH$^+$).

Example 17

Synthesis of 6,7-Dihydroxy-2-oxo-2H-chromene-3-carboxylic acid (3-imidazo[1,2-a]pyridin-2-yl-phenyl)-amide (7)

4,5-dihydroxy-salicylaldehyde (213.0 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 271.0 mg of 6,7-dihydroxy-3-carboxy-coumarin in an 88% yield.

DIEA (43.1 µL, 0.25 mmol) was added to 6,7-dihydroxy-3-carboxy-coumarin (50.0 mg, 0.23 mmol) and HATU (94.1 mg, 0.25 mmol) in 1 mL of DMF with constant stirring at room temperature until a clear solution resulted. Subsequently, 3-Imidazo[1,2-a]pyridin-2-yl-phenylamine (47.1 mg, 0.23 mmol) was added and allowed to react overnight when a solid precipitated out of solution. The resulting precipitate was filtered, dried under suction, and finally dried overnight in vacuo to give the final product: LCMS (ESI) m/z 413 (MH$^+$).

Example 18

Synthesis of 7,8-Dimethoxy-2-oxo-2H-chromene-3-carboxylic acid (3-imidazo[1,2-a]pyridin-2-yl-phenyl)-amide (8)

3,4-dimethoxy-salicylaldehyde (252.8 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 271.0 mg of 7,8-dimethoxy-3-carboxy-coumarin in an 78% yield.

DIEA (38.3 µL, 0.22 mmol) was added to 7,8-dimethoxy-3-carboxy-coumarin (500 mg, 0.20 mmol) and HATU (83.6 mg, 0.22 mmol) in 1 mL of DMF with constant stirring at room temperature until a clear solution resulted. Subsequently, 3-Imidazo[1,2-a]pyridin-2-yl-phenylamine (41.8 mg, 0.20 mmol) was added and allowed to react overnight when a solid precipitated out of solution. The resulting precipitate was filtered, dried under suction, and finally dried overnight in vacuo to give 68.7 mg of product in 78% yield: LCMS (ESI) m/z 442 (MH$^+$).

Example 19

Synthesis of 6-Trifluoromethoxy-2-oxo-2H-chromene-3-carboxylic acid (3-imidazo[1,2-a]pyridin-2-yl-phenyl)-amide (9)

5-trifluoromethoxy-salicylaldehyde (286.0 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 189.1 mg of 6-trifluoromethoxy-3-carboxy-coumarin in a 50% yield.

DIEA (34.9 µL, 0.20 mmol) was added to 6-trifluoromethoxy-3-carboxy-coumarin (50.0 mg, 0.18 mmol) and HATU (76.3 g, 0.20 mmol) in 1 mL of DMF with constant stirring at room temperature until a clear solution resulted. Subsequently, 3-Imidazo[1,2-a]pyridin-2-yl-phenylamine (38.2 mg, 0.18 mmol) was added and allowed to react overnight when a solid precipitated out of solution. The resulting precipitate was filtered, dried under suction, and finally dried overnight in vacuo to give 30.5 mg of product in 36% yield: LCMS (ESI) m/z 466 (MH$^+$).

Example 20

Synthesis of 6-Iodo-2-oxo-2H-chromene-3-carboxylic acid (3-imidazo[1,2-a]pyridin-2-yl-phenyl)-amide (10)

5-iodosalicylaldehyde (344.2 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 302.0 mg of 6-iodo-3-carboxy-coumarin in 69% yield.

DIEA (30.3 µL, 0.17 mmol) was added to 6-iodo-3-carboxy-coumarin (50.0 mg, 0.16 mmol) and HATU (66.2 g, 0.17 mmol) in 1 mL of DMF with constant stirring at room temperature until a clear solution resulted. Subsequently, 3-Imidazo[1,2-a]pyridin-2-yl-phenylamine (33.1 mg, 0.16 mmol) was added and allowed to react overnight when a solid precipitated out of solution. The resulting precipitate was filtered, dried under suction, and finally dried overnight in vacuo to give 27.4 mg of product in 34% yield: LCMS (ESI) m/z 508 (MH$^+$).

Example 21

Synthesis of 6-Hydroxy-2-oxo-2H-chromene-3-carboxylic acid (3-imidazo[1,2-a]pyridin-2-yl-phenyl)-amide (11)

5-hydroxysalicylaldehyde (191.7 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 249.0 mg of product in 87% yield.

DIEA (46.5 μL, 0.27 mmol) was added to 6-hydroxy-3-carboxy-coumarin (50.0 mg, 0.24 mmol) and HATU (101.4 mg, 0.27 mmol) in 1 mL of DMF with constant stirring at room temperature until a clear solution resulted. Subsequently, 3-Imidazo[1,2-a]pyridin-2-yl-phenylamine (50.8 mg, 0.24 mmol) was added and allowed to react overnight when a solid precipitated out of solution. The resulting precipitate was filtered, dried under suction, and finally dried overnight in vacuo to give 81.1 mg of product in 85% yield: LCMS (ESI) m/z 398 (MH+).

Example 22

Synthesis of 6-Methoxy-2-oxo-2H-chromene-3-carboxylic acid (3-imidazo[1,2-a]pyridin-2-yl-phenyl)-amide (12)

5-methoxysaliclaldehde (211.1 mg, 1.39 mmol) and Meldrum's acid (200 mg, 1.39 mmol) were combined in H$_2$O (2 mL). The solution was stirred at 75° C. for 2 h. After cooling to room temperature, the precipitate was filtered and dried at suction to give 241. mg of 6-methoxy-3-carboxy-coumarin in a 79% yield.

DIEA (43.5 μL, 0.25 mmol) was added to 6-methoxy-3-carboxy-coumarin (50.0 mg, 0.23 mmol) and HATU (95.0 mg, 0.25 mmol) in 1 mL of DMF with constant stirring at room temperature until a clear solution resulted. Subsequently, 3-Imidazo[1,2-a]pyridin-2-yl-phenylamine (475. mg, 0.23 mmol) was added and allowed to react overnight when a solid precipitated out of solution. The resulting precipitate was filtered, dried under suction, and finally dried overnight in vacuo to give 78.5 mg of product in 83% yield: LCMS (ESI) m/z 412 (MH+).

Example 23

Synthesis of 2-oxo-2H-chromene-3-carboxylic acid (3-imidazo[1,2-a]pyridin-2-yl-phenyl)-amide (13)

DIEA (50.4 μL, 0.29 mmol) was added to 3-carboxy-coumarin (50.0 mg, 0.26 mmol) and HATU (110.0 mg, 0.29 mmol) in 1 mL of DMF with constant stirring at room temperature until a clear solution resulted. Subsequently, 3-Imidazo[1,2-a]pyridin-2-yl-phenylamine (55.0 mg, 0.26 mmol) was added and allowed to react overnight when a solid precipitated out of solution. The resulting precipitate was filtered, dried under suction, and finally dried overnight in vacuo to give 83.6 mg of product in 85% yield: LCMS (ESI) m/z 382 (MH+).

Example 24

Synthesis of 6-Methoxy-8-morpholin-4-yl-2-oxo-2H-chromene-3-carboxylic acid (3-imidazo[1,2-a]pyridin-2-yl-phenyl)-amide (14)

3-morpholin-5-methoxysalicylaldehyde (100 mg, 0.40 mmol) and Meldrum's acid (60.5 mg, 0.42 mmol) were combined in H$_2$O (1 mL). The solution was stirred at 75° C. for 2 h. After cooling to room temperature, the precipitate was filtered and dried at suction to give 76.7 mg of 6-methoxy-8-morpholin-3-carboxy-coumarin in an 60% yield.

DIEA (30.0 μL, 0.17 mmol) was added to 6-methoxy-8-morpholin-3-carboxy-coumarin (50 mg, 0.16 mmol) and HATU (65.5 mg, 0.17 mmol) in 1 mL of DMF with constant stirring at room temperature until a clear solution resulted. Subsequently, 3-Imidazo[1,2-a]pyridin-2-yl-phenylamine (32.8 mg, 0.16 mmol) was added and allowed to react overnight when a solid precipitated out of solution. The resulting precipitate was filtered, dried under suction, and finally dried overnight in vacuo to give 46.8 mg of product in 57% yield: LCMS (ESI) m/z 511 (MH+).

Example 25

Synthesis of 8-Hydroxy-2-oxo-2H-chromene-3-carboxylic acid [3-(1H-benzoimidazol-2-yl)-phenyl]-amide (15)

2,3-dihydroxybenzaldehyde (95.8 mg, 0.69 mmol) and Meldrum's acid (100 mg, 0.69 mmol) were combined in H$_2$O (1 mL). The solution was stirred at 75° C. for 2 h. After cooling to room temperature, the precipitate was filtered and dried at suction to give 8-hydroxy-3-carboxy-coumarin.

DIEA (46.5 μL, 0.27 mmol) was added to 8-hydroxy-3-carboxy-coumarin (50.0 mg, 0.24 mmol) and HATU (101.4 mg, 0.27 mmol) in 1 mL of DMF with constant stirring at room temperature until a clear solution resulted. Subsequently, 3-(1H-benzoimidazol-2-yl)-phenyl (50.8 mg, 0.24 mmol) was added and allowed to react overnight when a solid precipitated out of solution. The resulting precipitate was filtered, dried under suction, and finally dried overnight in vacuo to give final product: LCMS (ESI) m/z 398 (MH+).

Example 26

Synthesis of 8-Hydroxy-2-oxo-2H-chromene-3-carboxylic acid (3-morpholin-4-yl-phenyl)-amide (16)

DIEA (0.028 mL, 0.160 mmol) was added to 8-hydroxy-3-carboxy-coumarin (0.030 g, 0.146 mmol) and HATU (0.061 g, 0.160 mmol) in 0.5 mL of DMF with constant stirring at room temperature until a clear solution resulted. Subsequently, 3-morpholin-4-ylaniline (0.026 g, 0.146 mmol) was added and allowed to react overnight when a solid precipitated out of solution. The resulting precipitate was filtered, dried under suction, and finally dried overnight in vacuo to give 0.023 g of product in 43% yield: LCMS (ESI) m/z 367 (MH+).

Example 27

Synthesis of 8-Hydroxy-2-oxo-2H-chromene-3-carboxylic acid (3-pyridin-3-yl-phenyl)-amide (17)

DIEA (0.028 mL, 0.160 mmol) was added to 8-hydroxy-3-carboxy-coumarin (0.030 g, 0.146 mmol) and HATU (0.061 g, 0.160 mmol) in 0.5 mL of DMF with constant stirring at room temperature until a clear solution resulted. Subsequently, 3-pyridin-3-ylaniline (0.025 g, 0.146 mmol) was added and allowed to react overnight when a solid precipitated out of solution. The resulting precipitate was filtered, dried under suction, and finally dried overnight in vacuo to give 0.017 g of product in 32% yield: LCMS (ESI) m/z 359 (MH+).

Example 28

Synthesis of 8-Methoxy-2-oxo-2H-chromene-3-carboxylic acid (3-pyridin-3-yl-phenyl)-amide (18)

DIEA (43.5 μL, 0.25 mmol) was added to 8-methoxy-3-carboxy-coumarin (50.0 mg, 0.23 mmol) and HATU (95.0 mg, 0.25 mmol) in 1 mL of DMF with constant stirring at room temperature until a clear solution resulted. Subsequently, 3-pyridin-3-yl-phenylamine (38.7 mg, 0.23 mmol) was added and allowed to react overnight when a solid precipitated out of solution. The resulting precipitate was filtered, dried under suction, and finally dried overnight in vacuo to give 71.6 mg of product in 84% yield: LCMS (ESI) m/z 373 (MH$^+$).

Example 29

Synthesis of 8-Hydroxy-2-oxo-2H-chromene-3-carboxylic acid (3-pyridin-4-yl-phenyl)-amide (19)

DIEA (0.028 mL, 0.160 mmol) was added to 8-hydroxy-3-carboxy-coumarin (0.030 g, 0.146 mmol) and HATU (0.061 g, 0.160 mmol) in 0.5 mL of DMF with constant stirring at room temperature until a clear solution resulted. Subsequently, 3-pyridin-4-ylaniline (0.025 g, 0.146 mmol) was added and allowed to react overnight when a solid precipitated out of solution. The resulting precipitate was filtered, dried under suction, and finally dried overnight in vacuo to give 0.022 g of product in 42% yield: LCMS (ESI) m/z 359 (MH$^+$).

Example 30

Synthesis of 8-Methoxy-2-oxo-2H-chromene-3-carboxylic acid (3-pyridin-4-yl-phenyl)-amide (20)

DIEA (43.5 µL, 0.25 mmol) was added to 8-methoxy-3-carboxy-coumarin (50.0 mg, 0.23 mmol) and HATU (95.0 mg, 0.25 mmol) in 1 mL of DMF with constant stirring at room temperature until a clear solution resulted. Subsequently, 3-Imidazo[1,2-a]pyridin-2-yl-phenylamine (38.7 mg, 0.23 mmol) was added and allowed to react overnight when a solid precipitated out of solution. The resulting precipitate was filtered, dried under suction, and finally dried overnight in vacuo to give 65.0 mg of product in 76% yield: LCMS (ESI) m/z 373 (MH$^+$).

Example 31

Synthesis of 3-(2-Ethoxy-pyridin-3-yl)-phenylamine (21)

2-ethoxypyridine-3-boronic acid (0.123 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (0-10% EtOAc/hexanes). The purification was monitored by TLC. The solvent was removed from fractions containing product, resulting in 0.079 g in 80% yield.

Example 32

Synthesis of 8-Hydroxy-2-oxo-2H-chromene-3-carboxylic acid [3-(2-ethoxy-pyridin-3-yl)-phenyl]-amide (41)

DIEA (0.013 mL, 0.077 mmol) was added to 8-hydroxy-3-carboxy-coumarin (0.014 g, 0.070 mmol) and HATU (0.029 g, 0.077 mmol) in 0.36 mL of DMF with constant stirring at room temperature until a clear solution resulted. Subsequently, 3-(2-Ethoxy-pyridin-3-yl)-phenylamine (0.015 g, 0.070 mmol) was added and allowed to react overnight when a solid precipitated out of solution. The resulting precipitate was filtered, dried under suction, and finally dried overnight in vacuo to give 0.017 g of product in 61% yield: LCMS (ESI) m/z 403 (MH$^+$).

Example 33

Synthesis of 8-Methoxy-2-oxo-2H-chromene-3-carboxylic acid [3-(2-ethoxy-pyridin-3-yl)-phenyl]-amide (42)

DIEA (0.013 mL, 0.077 mmol) was added to 8-methoxy-3-carboxy-coumarin (0.015 g, 0.070 mmol) and HATU (0.029 g, 0.077 mmol) in 0.36 mL of DMF with constant stirring at room temperature until a clear solution resulted. Subsequently, 3-(2-Ethoxy-pyridin-3-yl)-phenylamine (0.015 g, 0.070 mmol) was added and allowed to react overnight when a solid precipitated out of solution. The resulting precipitate was filtered, dried under suction, and finally dried overnight in vacuo to give 0.025 g of product in 86% yield: LCMS (ESI) m/z 417 (MH$^+$).

Example 34

Synthesis of 8-Trifluoromethoxy-2-oxo-2H-chromene-3-carboxylic acid [3-(2-ethoxy-pyridin-3-yl)-phenyl]-amide (43)

DIEA (0.013 mL, 0.077 mmol) was added to 8-trifluoromethoxy-3-carboxy-coumarin (0.019 g, 0.070 mmol) and HATU (0.029 g, 0.077 mmol) in 0.36 mL of DMF with constant stirring at room temperature until a clear solution resulted. Subsequently, 3-(2-Ethoxy-pyridin-3-yl)-phenylamine (0.015 g, 0.070 mmol) was added and allowed to react overnight when a solid precipitated out of solution. The resulting precipitate was filtered, dried under suction, and finally dried overnight in vacuo to give 0.016 g of product in 48% yield: LCMS (ESI) m/z 471 (MH$^+$).

Example 35

Synthesis of 4'-Methoxy-biphenyl-3-ylamine (22)

4-methoxyphenyl boronic acid (0.105 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum. And the resulting residue was resuspended in H$_2$O and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.063 g in 68% yield.

Example 36

Synthesis of 8-Hydroxy-2-oxo-2H-chromene-3-carboxylic acid (4'-Methoxy-biphenyl-3-yl)-amide (44)

DIEA (0.0144 mL, 0.083 mmol) was added to 8-hydroxy-3-carboxy-coumarin (0.016 g, 0.075 mmol) and HATU (0.032 g, 0.083 mmol) in 0.36 mL of DMF with constant stirring at room temperature until a clear solution resulted. Subsequently, 4'-Methoxy-biphenyl-3-ylamine (0.015 g, 0.075 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.015 g of product in 52% yield: LCMS (ESI) m/z 388 (MH$^+$).

Example 37

Synthesis of 8-Methoxy-2-oxo-2H-chromene-3-carboxylic acid (4'-Methoxy-biphenyl-3-yl)-amide (45)

DIEA (0.0144 mL, 0.083 mmol) was added to 8-methoxy-3-carboxy-coumarin (0.017 g, 0.075 mmol) and HATU (0.032 g, 0.083 mmol) in 0.36 mL of DMF with constant stirring at room temperature until a clear solution resulted. Subsequently, 4'-Methoxy-biphenyl-3-ylamine (0.015 g, 0.075 mmol) was added and allowed to react overnight when a solid precipitated out of solution. The resulting precipitate was filtered, dried under suction, and finally dried overnight in vacuo to give 0.021 g of product in 68% yield: LCMS (ESI) m/z 402 (MH$^+$).

Example 38

Synthesis of 8-Trifluoromethoxy-2-oxo-2H-chromene-3-carboxylic acid (4'-Methoxy-biphenyl-3-yl)-amide (46)

DIEA (0.0144 mL, 0.083 mmol) was added to 8-trifluoromethoxy-3-carboxy-coumarin (0.021 g, 0.075 mmol) and HATU (0.032 g, 0.083 mmol) in 0.36 mL of DMF with constant stirring at room temperature until a clear solution resulted. Subsequently, 4'-Methoxy-biphenyl-3-ylamine (0.015 g, 0.075 mmol) was added and allowed to react overnight when a solid precipitated out of solution. The resulting precipitate was filtered, dried under suction, and finally dried overnight in vacuo to give 0.019 g of product in 55% yield: LCMS (ESI) m/z 456 (MH$^+$).

Example 39

Synthesis of 4'-Methoxy-3'-methyl-biphenyl-3-ylamine (23)

4-methoxy-3-methylphenyl boronic acid (0.115 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.074 g in 75% yield.

Example 40

Synthesis of 8-Hydroxy-2-oxo-2H-chromene-3-carboxylic acid (4'-Methoxy-3'-methyl-biphenyl-3-yl)-amide (47)

DIEA (0.014 mL, 0.077 mmol) was added to 8-hydroxy-3-carboxy-coumarin (0.015 g, 0.070 mmol) and HATU (0.029 g, 0.077 mmol) in 0.36 mL of DMF with constant stirring at room temperature until a clear solution resulted. Subsequently, 4'-Methoxy-3'-methyl-biphenyl-3-ylamine (0.015 g, 0.070 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.017 g of product in 61% yield: LCMS (ESI) m/z 402 (MH$^+$).

Example 41

Synthesis of 8-Methoxy-2-oxo-2H-chromene-3-carboxylic acid (4'-Methoxy-3'-methyl-biphenyl-3-yl)-amide (48)

DIEA (0.014 mL, 0.077 mmol) was added to 8-methoxy-3-carboxy-coumarin (0.016 g, 0.070 mmol) and HATU (0.029 g, 0.077 mmol) in 0.36 mL of DMF with constant stirring at room temperature until a clear solution resulted. Subsequently, 4'-Methoxy-3'-methyl-biphenyl-3-ylamine (0.015 g, 0.070 mmol) was added and allowed to react overnight when a solid precipitated out of solution. The resulting precipitate was filtered, dried under suction, and finally dried overnight in vacuo to give 0.023 g of product in 78% yield: LCMS (ESI) m/z 416 (MH$^+$).

Example 42

Synthesis of 8-Trifluoromethoxy-2-oxo-2H-chromene-3-carboxylic acid (4'-Methoxy-3'-methyl-biphenyl-3-yl)-amide (49)

DIEA (0.014 mL, 0.077 mmol) was added to 8-trifluoromethoxy-3-carboxy-coumarin (0.019 g, 0.070 mmol) and HATU (0.029 g, 0.077 mmol) in 0.36 mL of DMF with constant stirring at room temperature until a clear solution resulted. Subsequently, 4'-Methoxy-3'-methyl-biphenyl-3-ylamine (0.015 g, 0.070 mmol) was added and allowed to react overnight when a solid precipitated out of solution. The resulting precipitate was filtered, dried under suction, and finally dried overnight in vacuo to give 0.022 g of product in 65% yield: LCMS (ESI) m/z 470 (MH$^+$).

Example 43

Synthesis of 2',4'-dimethoxy-biphenyl-3-ylamine (24)

2,4-dimethoxyphenyl boronic acid (0.126 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (5-20% EtOAc/hexanes). The purification was monitored by TLC. The solvent was removed under vacuum from fractions containing product, resulting in 0.078 g in 74% yield.

Example 44

Synthesis of 8-Hydroxy-2-oxo-2H-chromene-3-carboxylic acid (2',4'-dimethoxy-biphenyl-3-yl)-amide (50)

DIEA (0.013 mL, 0.072 mmol) was added to 8-hydroxy-3-carboxy-coumarin (0.014 g, 0.065 mmol) and HATU (0.027 g, 0.072 mmol) in 0.36 mL of DMF with constant stirring at room temperature until a clear solution resulted. Subsequently, 2',4'-dimethoxy-biphenyl-3-ylamine (0.015 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.019 g of product in 70% yield: LCMS (ESI) m/z 418 (MH$^+$).

Example 45

Synthesis of 8-Methoxy-2-oxo-2H-chromene-3-carboxylic acid (2',4'-dimethoxy-biphenyl-3-yl)-amide (51)

DIEA (0.013 mL, 0.072 mmol) was added to 8-methoxy-3-carboxy-coumarin (0.014 g, 0.065 mmol) and HATU (0.027 g, 0.072 mmol) in 0.36 mL of DMF with constant stirring at room temperature until a clear solution resulted. Subsequently, 2',4'-dimethoxy-biphenyl-3-ylamine (0.015 g, 0.065 mmol) was added and allowed to react overnight when a solid precipitated out of solution. The resulting precipitate was filtered, dried under suction, and finally dried overnight in vacuo to give 0.024 g of product in 86% yield: LCMS (ESI) m/z 432 (MH$^+$).

Example 46

Synthesis of 8-Trifluoromethoxy-2-oxo-2H-chromene-3-carboxylic acid (2',4'-dimethoxy-biphenyl-3-yl)-amide (52)

DIEA (0.013 mL, 0.072 mmol) was added to 8-trifluoromethoxy-3-carboxy-coumarin (0.018 g, 0.065 mmol) and HATU (0.027 g, 0.072 mmol) in 0.36 mL of DMF with constant stirring at room temperature until a clear solution resulted. Subsequently, 2',4'-dimethoxy-biphenyl-3-ylamine (0.015 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.022 g of product in 70% yield: LCMS (ESI) m/z 486 (MH$^+$).

Example 47

Synthesis of 3',4'-dimethoxy-biphenyl-3-ylamine (25)

3,4-dimethoxyphenyl boronic acid (0.126 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.067 g in 63% yield.

Example 48

Synthesis of 8-Hydroxy-2-oxo-2H-chromene-3-carboxylic acid (3',4'-Dimethoxy-biphenyl-3-yl)-amide (53)

DIEA (0.013 mL, 0.072 mmol) was added to 8-hydroxy-3-carboxy-coumarin (0.014 g, 0.065 mmol) and HATU (0.027 g, 0.072 mmol) in 0.36 mL of DMF with constant stirring at room temperature until a clear solution resulted. Subsequently, 3',4'-Dimethoxy-biphenyl-3-ylamine (0.015 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.005 g of product in 19% yield: LCMS (ESI) m/z 418 (MH$^+$).

Example 49

Synthesis of 8-Methoxy-2-oxo-2H-chromene-3-carboxylic acid (3',4'-Dimethoxy-biphenyl-3-yl)-amide (54)

DIEA (0.013 mL, 0.072 mmol) was added to 8-methoxy-3-carboxy-coumarin (0.014 g, 0.065 mmol) and HATU (0.027 g, 0.072 mmol) in 0.36 mL of DMF with constant stirring at room temperature until a clear solution resulted. Subsequently, 3',4'-Dimethoxy-biphenyl-3-ylamine (0.015 g, 0.065 mmol) was added and allowed to react overnight when a solid precipitated out of solution. The resulting precipitate was filtered, dried under suction, and finally dried overnight in vacuo to give 0.018 g of product in 64% yield: LCMS (ESI) m/z 432 (MH$^+$).

Example 50

Synthesis of 8-Trifluoromethoxy-2-oxo-2H-chromene-3-carboxylic acid (3',4'-Dimethoxy-biphenyl-3-yl)-amide (55)

DIEA (0.0144 mL, 0.072 mmol) was added to 8-trifluoromethoxy-3-carboxy-coumarin (0.018 g, 0.065 mmol) and HATU (0.027 g, 0.072 mmol) in 0.36 mL of DMF with constant stirring at room temperature until a clear solution resulted. Subsequently, 3',4'-Dimethoxy-biphenyl-3-ylamine (0.015 g, 0.065 mmol) was added and allowed to react overnight when a solid precipitated out of solution. The resulting precipitate was filtered, dried under suction, and finally dried overnight in vacuo to give 0.021 g of product in 65% yield: LCMS (ESI) m/z 486 (MH+).

Example 51

Synthesis of 2',5'-dimethoxy-biphenyl-3-ylamine (26)

2,5-dimethoxyphenyl boronic acid (0.126 g, 0.693 mmol) and 3-bromoaniline (0.05 mL, 0.462 mmol) were combined in DME (2 mL) in a flame-dried, round-bottom flask. $Na_2CO_3$ (2M, 0.485 mL, 0.970 mmol) and $Pd(PPh_3)_4$ (0.017 g, 0.014 mmol) were added to the stirred solution. The reaction was refluxed overnight under argon flow, and subsequently cooled to room temperature. The solvent was removed under vacuum and the resulting residue was resuspended in $H_2O$ and extracted with $CH_2Cl_2$. The organic phase was dried over $MgSO_4$ and concentrated under vacuum. The crude product was purified by silica column chromatography (0-20% EtOAc/hexanes). The purification was monitored by TLC. The solvent was removed under vacuum from fractions containing product, resulting in 0.091 g in 91% yield.

Example 52

Synthesis of 8-Hydroxy-2-oxo-2H-chromene-3-carboxylic acid (2',5'-dimethoxy-biphenyl-3-yl)-amide (56)

DIEA (0.013 mL, 0.072 mmol) was added to 8-hydroxy-3-carboxy-coumarin (0.013 g, 0.065 mmol) and HATU (0.027 g, 0.072 mmol) in 0.36 mL of DMF with constant stirring at room temperature until a clear solution resulted. Subsequently, 2',5'-dimethoxy-biphenyl-3-ylamine (0.015 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and lyophilized for 48 hours to give 0.007 g of product in 27% yield: LCMS (ESI) m/z 418 (MH+).

Example 53

Synthesis of 8-Methoxy-2-oxo-2H-chromene-3-carboxylic acid (2',5'-dimethoxy-biphenyl-3-yl)-amide (57)

DIEA (0.013 mL, 0.072 mmol) was added to 8-methoxy-3-carboxy-coumarin (0.014 g, 0.065 mmol) and HATU (0.027 g, 0.072 mmol) in 0.36 mL of DMF with constant stirring at room temperature until a clear solution resulted. Subsequently, 2',5'-dimethoxy-biphenyl-3-ylamine (0.015 g, 0.065 mmol) was added and allowed to react overnight when a solid precipitated out of solution. The resulting precipitate was filtered, dried under suction, and finally dried overnight in vacuo to give 0.023 g of product in 83% yield: LCMS (ESI) m/z 432 (MH+).

Example 54

Synthesis of 8-Trifluoromethoxy-2-oxo-2H-chromene-3-carboxylic acid (2',5'-dimethoxy-biphenyl-3-yl)-amide (58)

DIEA (0.013 mL, 0.072 mmol) was added to 8-trifluoromethoxy-3-carboxy-coumarin (0.018 g, 0.065 mmol) and HATU (0.027 g, 0.072 mmol) in 0.36 mL of DMF with constant stirring at room temperature until a clear solution resulted. Subsequently, 2',5'-dimethoxy-biphenyl-3-ylamine (0.015 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and lyophilized for 48 hours to give 0.02 g of product in 64% yield: LCMS (ESI) m/z 486 (MH+).

Example 55

Synthesis of 4'-phenoxy-biphenyl-3-ylamine (27)

4-phenoxyphenyl boronic acid (0.148 g, 0.693 mmol) and 3-bromoaniline (0.05 mL, 0.462 mmol) in DME (2 mL) were combined in a flame-dried, round-bottom flask. $Na_2CO_3$ (2M, 0.485 mL, 0.970 mmol) and $Pd(PPh_3)_4$ (0.017 g, 0.014 mmol) were added to the stirred solution. The reaction was refluxed overnight under argon flow, and subsequently cooled to room temperature. The solvent was removed under vacuum and the resulting residue was resuspended in $H_2O$ and extracted with $CH_2Cl_2$. The organic phase was dried over $MgSO_4$ and concentrated under vacuum. The crude product was purified by silica column chromatography (0-20% EtOAc/hexanes). The purification was monitored by TLC. The solvent was removed under vacuum from fractions containing product, resulting in 0.065 g in 54% yield.

Example 56

Synthesis of 8-Hydroxy-2-oxo-2H-chromene-3-carboxylic acid (4'-phenoxy-biphenyl-3-yl)-amide (59)

DIEA (0.011 mL, 0.063 mmol) was added to 8-hydroxy-3-carboxy-coumarin (0.012 g, 0.057 mmol) and HATU (0.024 g, 0.063 mmol) in 0.36 mL of DMF with constant stirring at room temperature until a clear solution resulted. Subsequently, 4'-phenoxy-biphenyl-3-ylamine (0.015 g, 0.057 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.009 g of product in 34% yield: LCMS (ESI) m/z 450 (MH+).

Example 57

Synthesis of 8-Methoxy-2-oxo-2H-chromene-3-carboxylic acid (4'-phenoxy-biphenyl-3-yl)-amide (60)

DIEA (0.011 mL, 0.063 mmol) was added to 8-methoxy-3-carboxy-coumarin (0.013 g, 0.057 mmol) and HATU (0.024 g, 0.063 mmol) in 0.36 mL of DMF with constant stirring at room temperature until a clear solution resulted. Subsequently, 4'-phenoxy-biphenyl-3-ylamine (0.015 g, 0.057 mmol) was added and allowed to react overnight when a solid precipitated out of solution. The resulting precipitate was filtered, dried under suction, and finally dried overnight in vacuo to give 0.022 g of product in 83% yield: LCMS (ESI) m/z 464 (MH$^+$).

Example 58

Synthesis of 8-Trifluoromethoxy-2-oxo-2H-chromene-3-carboxylic acid (4'-phenoxy-biphenyl-3-yl)-amide (61)

DIEA (0.011 mL, 0.063 mmol) was added to 8-trifluoromethoxy-3-carboxy-coumarin (0.016 g, 0.057 mmol) and HATU (0.024 g, 0.063 mmol) in 0.36 mL of DMF with constant stirring at room temperature until a clear solution resulted. Subsequently, 4'-phenoxy-biphenyl-3-ylamine (0.015 g, 0.057 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.023 g of product in 78% yield: LCMS (ESI) m/z 518 (MH$^+$).

Example 59

Synthesis of 3-Benzo[1,3]dioxol-5-yl-phenylamine (28)

3,4-methylenedioxyphenyl boronic acid (0.115 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$0 and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.057 g in 58% yield.

Example 60

Synthesis of 8-Hydroxy-2-oxo-2H-chromene-3-carboxylic acid (3-Benzo[1,3]dioxol-5-yl-phenyl)-amide (62)

DIEA (0.014 mL, 0.077 mmol) was added to 8-hydroxy-3-carboxy-coumarin (0.015 g, 0.070 mmol) and HATU (0.029 g, 0.077 mmol) in 0.36 mL of DMF with constant stirring at room temperature until a clear solution resulted. Subsequently, 3-Benzo[1,3]dioxol-5-yl-phenylamine (0.015 g, 0.070 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.008 g of product in 29% yield: LCMS (ESI) m/z 402 (MH$^+$).

Example 61

Synthesis of 8-Methoxy-2-oxo-2H-chromene-3-carboxylic acid (3-Benzo[1,3]dioxol-5-yl-phenyl)-amide (63)

DIEA (0.014 mL, 0.077 mmol) was added to 8-methoxy-3-carboxy-coumarin (0.016 g, 0.070 mmol) and HATU (0.029 g, 0.077 mmol) in 0.36 mL of DMF with constant stirring at room temperature until a clear solution resulted. Subsequently, 3-Benzo[1,3]dioxol-5-yl-phenylamine (0.015 g, 0.070 mmol) was added and allowed to react overnight when a solid precipitated out of solution. The resulting precipitate was filtered, dried under suction, and finally dried overnight in vacuo to give 0.023 g of product in 77% yield: LCMS (ESI) m/z 416 (MH$^+$).

Example 62

Synthesis of 8-Trifluoromethoxy-2-oxo-2H-chromene-3-carboxylic acid (3-Benzo[1,3]dioxol-5-yl-phenyl)-amide (64)

DIEA (0.014 mL, 0.077 mmol) was added to 8-trifluoromethoxy-3-carboxy-coumarin (0.019 g, 0.070 mmol) and HATU (0.029 g, 0.077 mmol) in 0.36 mL of DMF with constant stirring at room temperature until a clear solution resulted. Subsequently, 3-Benzo[1,3]dioxol-5-yl-phenylamine (0.015 g, 0.070 mmol) was added and allowed to react overnight when a solid precipitated out of solution. The resulting precipitate was filtered, dried under suction, and finally dried overnight in vacuo to give 0.023 g of product in 70% yield: LCMS (ESI) m/z 470 (MH$^+$).

Example 63

Synthesis of 4'-Ethoxy-3'-methyl-biphenyl-3-ylamine (29)

4-ethoxy-3-methylphenyl boronic acid (0.125 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$0 and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.071 g in 67% yield.

Example 64

Synthesis of 8-Hydroxy-2-oxo-2H-chromene-3-carboxylic acid (4'-ethoxy-3'-methyl-biphenyl-3-yl)-amide (65)

DIEA (0.013 mL, 0.072 mmol) was added to 8-hydroxy-3-carboxy-coumarin (0.013 g, 0.067 mmol) and HATU (0.028 g, 0.072 mmol) in 0.37 mL of DMF with constant stirring at room temperature until a clear solution resulted. Subsequently, 4'-ethoxy-3'-methyl-biphenyl-3-ylamine (0.015 g, 0.067 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and lyophilized for 48 hours to give 0.011 g of product in 41% yield: LCMS (ESI) m/z 416 (MH$^+$).

Example 65

Synthesis of 8-Methoxy-2-oxo-2H-chromene-3-carboxylic acid (4'-ethoxy-3'-methyl-biphenyl-3-yl)-amide (66)

DIEA (0.013 mL, 0.072 mmol) was added to 8-methoxy-3-carboxy-coumarin (0.016 g, 0.067 mmol) and HATU (0.028 g, 0.072 mmol) in 0.37 mL of DMF with constant stirring at room temperature until a clear solution resulted. Subsequently, 4'-ethoxy-3'-methyl-biphenyl-3-ylamine (0.015 g, 0.067 mmol) was added and allowed to react overnight when a solid precipitated out of solution. The resulting precipitate was filtered, dried under suction, and finally dried overnight in vacuo to give 0.018 g of product in 65% yield: LCMS (ESI) m/z 430 (MH$^+$).

Example 66

Synthesis of 8-Trifluoromethoxy-2-oxo-2H-chromene-3-carboxylic acid (4'-ethoxy-3'-methyl-biphenyl-3-yl)-amide (67)

DIEA (0.013 mL, 0.072 mmol) was added to 8-trifluoromethoxy-3-carboxy-coumarin (0.020 g, 0.067 mmol) and HATU (0.028 g, 0.072 mmol) in 0.37 mL of DMF with constant stirring at room temperature until a clear solution resulted. Subsequently, 4'-ethoxy-3'-methyl-biphenyl-3-ylamine (0.015 g, 0.067 mmol) was added and allowed to react overnight when a solid precipitated out of solution. The resulting precipitate was filtered, dried under suction, and finally dried overnight in vacuo to give 0.017 g of product in 53% yield: LCMS (ESI) m/z 484 (MH$^+$).

Example 67

Synthesis of 4'-Ethoxy-biphenyl-3-ylamine (30)

4-ethoxyphenyl boronic acid (0.115 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.067 g in 68% yield.

Example 68

Synthesis of 8-Hydroxy-2-oxo-2H-chromene-3-carboxylic acid (4'-Ethoxy-biphenyl-3-yl)-amide (68)

DIEA (0.014 mL, 0.077 mmol) was added to 8-hydroxy-3-carboxy-coumarin (0.015 g, 0.070 mmol) and HATU (0.029 g, 0.077 mmol) in 0.36 mL of DMF with constant stirring at room temperature until a clear solution resulted. Subsequently, 4'-ethoxy-biphenyl-3-ylamine (0.015 g, 0.070 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.012 g of product in 41% yield: LCMS (ESI) m/z 402 (MH$^+$).

Example 69

Synthesis of 8-Methoxy-2-oxo-2H-chromene-3-carboxylic acid (4'-ethoxy-biphenyl-3-yl)-amide (69)

DIEA (0.014 mL, 0.077 mmol) was added to 8-methoxy-3-carboxy-coumarin (0.016 g, 0.070 mmol) and HATU (0.029 g, 0.077 mmol) in 0.36 mL of DMF with constant stirring at room temperature until a clear solution resulted. Subsequently, 4'-ethoxy-biphenyl-3-ylamine (0.015 g, 0.070 mmol) was added and allowed to react overnight when a solid precipitated out of solution. The resulting precipitate was filtered, dried under suction, and finally dried overnight in vacuo to give 0.021 g of product in 73% yield: LCMS (ESI) m/z 416 (MH$^+$).

Example 70

Synthesis of 8-Trifluoromethoxy-2-oxo-2H-chromene-3-carboxylic acid (4'-ethoxy-biphenyl-3-yl)-amide (70)

DIEA (0.014 mL, 0.077 mmol) was added to 8-trifluoromethoxy-3-carboxy-coumarin (0.019 g, 0.070 mmol) and HATU (0.029 g, 0.077 mmol) in 0.36 mL of DMF with constant stirring at room temperature until a clear solution resulted. Subsequently, 4'-ethoxy-biphenyl-3-ylamine (0.015 g, 0.070 mmol) was added and allowed to react overnight when a solid precipitated out of solution. The resulting precipitate was filtered, dried under suction, and finally dried overnight in vacuo to give 0.018 g of product in 55% yield: LCMS (ESI) m/z 470 (MH$^+$).

Example 71

Synthesis of 2'-trifluoromethoxy-biphenyl-3-ylamine (31)

2-trifluoromethoxyphenylboronic acid (0.143 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H₂O and extracted with CH₂Cl₂. The organic phase was dried over MgSO₄ and concentrated under vacuum. The crude product was purified by silica column chromatography (0-5% EtOAc/hexanes). The purification was monitored by TLC. The solvent was removed under vacuum from fractions containing product, resulting in 0.086 g in 74% yield.

Example 72

Synthesis of 8-Hydroxy-2-oxo-2H-chromene-3-carboxylic acid (2'-trifluoromethoxy-biphenyl-3-yl)-amide (71)

DIEA (0.011 mL, 0.065 mmol) was added to 8-hydroxy-3-carboxy-coumarin (0.012 g, 0.059 mmol) and HATU (0.025 g, 0.065 mmol) in 0.36 mL of DMF with constant stirring at room temperature until a clear solution resulted. Subsequently, 2'-trifluoromethoxy-biphenyl-3-ylamine (0.015 g, 0.059 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H₂O with 0.05% TFA at a flow rate of 20 mL/min. UV absorbance was monitored at 254 nm and the fractions corresponding to the product peak were collected and the solvent removed under vacuum to give 0.017 g of product in 63% yield: LCMS (ESI) m/z 442 (MH⁺).

Example 73

Synthesis of 8-Methoxy-2-oxo-2H-chromene-3-carboxylic acid (2'-trifluoromethoxy-biphenyl-3-yl)-amide (72)

DIEA (0.011 mL, 0.065 mmol) was added to 8-methoxy-3-carboxy-coumarin (0.013 g, 0.059 mmol) and HATU (0.025 g, 0.065 mmol) in 0.36 mL of DMF with constant stirring at room temperature until a clear solution resulted. Subsequently, 2'-trifluoromethoxy-biphenyl-3-ylamine (0.015 g, 0.059 mmol) was added and allowed to react overnight when a solid precipitated out of solution. The resulting precipitate was filtered, dried under suction, and finally dried overnight in vacuo to give 0.021 g of product in 76% yield: LCMS (ESI) m/z 456 (MH⁺).

Example 74

Synthesis of 8-Trifluoromethoxy-2-oxo-2H-chromene-3-carboxylic acid (2'-trifluoromethoxy-biphenyl-3-yl)-amide (73)

DIEA (0.011 mL, 0.065 mmol) was added to 8-trifluoromethoxy-3-carboxy-coumarin (0.016 g, 0.059 mmol) and HATU (0.025 g, 0.065 mmol) in 0.36 mL of DMF with constant stirring at room temperature until a clear solution resulted. Subsequently, 2'-trifluoromethoxy-biphenyl-3-ylamine (0.015 g, 0.059 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H₂O with 0.05% TFA at a flow rate of 20 mL/min. UV absorbance was monitored at 254 nm and the fractions corresponding to the product peak were collected and the solvent removed under vacuum to give 0.027 g of product in 90% yield: LCMS (ESI) m/z 510 (MH⁺).

Example 75

Synthesis of 3-(2,3-Dihydro-benzofuran-5-yl)-phenylamine (32)

2,3-dihydrobenzofuran-5-boronic acid (0.114 g, 0.693 mmol) and 3-bromoaniline (0.05 mL, 0.462 mmol) were combined in DME (2 mL) in a flame-dried, round-bottom flask. Na₂CO₃ (2M, 0.485 mL, 0.970 mmol) and Pd(PPh₃)₄ (0.017 g, 0.014 mmol) were added to the stirred solution. The reaction was refluxed overnight under argon flow, and subsequently cooled to room temperature. The solvent was removed under vacuum and the resulting residue was resuspended in H₂O and extracted with CH₂Cl₂. The organic phase was dried over MgSO₄ and concentrated under vacuum. The crude product was purified by silica column chromatography (5-20% EtOAc/hexanes). The purification was monitored by TLC. The solvent was removed under vacuum from fractions containing product, resulting in 0.0762 g in 78% yield.

Example 76

Synthesis of 8-Hydroxy-2-oxo-2H-chromene-3-carboxylic acid [3-(2,3-Dihydro-benzofuran-5-yl)-phenyl]-amide (74)

DIEA (0.014 mL, 0.078 mmol) was added to 8-hydroxy-3-carboxy-coumarin (0.015 g, 0.071 mmol) and HATU (0.030 g, 0.078 mmol) in 0.36 mL of DMF with constant stirring at room temperature until a clear solution resulted. Subsequently, 3-(2,3-dihydro-benzofuran-5-yl)-phenylamine (0.015 g, 0.071 mmol) was added and allowed to react overnight when a solid precipitated out of solution. The resulting precipitate was filtered, dried under suction, and finally dried overnight in vacuo to give 0.014 g of product in 49% yield: LCMS (ESI) m/z 400 (MH⁺).

Example 77

Synthesis of 8-Methoxy-2-oxo-2H-chromene-3-carboxylic acid [3-(2,3-dihydro-benzofuran-5-yl)-phenyl]-amide (75)

DIEA (0.014 mL, 0.078 mmol) was added to 8-methoxy-3-carboxy-coumarin (0.016 g, 0.071 mmol) and HATU (0.030 g, 0.078 mmol) in 0.36 mL of DMF with constant stirring at room temperature until a clear solution resulted. Subsequently, 3-(2,3-dihydro-benzofuran-5-yl)-phenylamine (0.015 g, 0.071 mmol) was added and allowed to react overnight when a solid precipitated out of solution. The resulting precipitate was filtered, dried under suction, and finally dried overnight in vacuo to give 0.028 g of product in 94% yield: LCMS (ESI) m/z 414 (MH⁺).

Example 78

Synthesis of 8-Trifluoromethoxy-2-oxo-2H-chromene-3-carboxylic acid [3-(2,3-dihydro-benzofuran-5-yl)-phenyl]-amide (76)

DIEA (0.014 mL, 0.078 mmol) was added to 8-trifluoromethoxy-3-carboxy-coumarin (0.020 g, 0.071 mmol) and HATU (0.030 g, 0.078 mmol) in 0.36 mL of DMF with constant stirring at room temperature until a clear solution resulted. Subsequently, 3-(2,3-dihydro-benzofuran-5-yl)-phenylamine (0.015 g, 0.070 mmol) was added and allowed to react overnight when a solid precipitated out of solution. The resulting precipitate was filtered, dried under suction, and finally dried overnight in vacuo to give 0.026 g of product in 76% yield: LCMS (ESI) m/z 484 (MH$^+$).

Example 79

Synthesis of 3-(6-Methoxy-naphthalen-2-yl)-phenylamine (33)

6-methoxy-naphthalene-2-boronic acid (0.140 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.06 g in 75% yield.

Example 80

Synthesis of 8-Hydroxy-2-oxo-2H-chromene-3-carboxylic acid [3-(6-methoxy-naphthalen-2-yl)-phenyl]-amide (77)

Diisopropylethylamine (DIEA, 0.0115 mL, 0.067 mmol) was added to 8-hydroxy-3-carboxy-coumarin (0.012 g, 0.06 mmol) and O-(7-Azabenzotriazole-1-yl)-N,N,N',N'-tetramethyluronium hexafluorophosphate (HATU, 0.025 g, 0.067 mmol) in 0.5 mL of dimethylformamide (DMF) with constant stirring at room temperature until a clear solution resulted. Subsequently, 3-(6-methoxy-naphthalen-2-yl)-phenylamine (0.015 g, 0.06 mmol) was added and allowed to react overnight. DMF was removed under vacuum and the reaction was resuspended in dimethylsulfoxide (DMSO). The crude product was purified on a Parallex Flex parallel preparative reverse phase HPLC instrument (Biotage) using a solvent gradient of 10-95% acetonitrile (ACN)/H$_2$O with 0.05% trifluoroacetic acid (TFA) at a flow rate of 20 mL/min. UV absorbance was monitored at 254 nm and the fractions corresponding to the product peak were collected. Solvent was removed under vacuum and the resulting solid was left overnight in vacuo to give 0.010 g of product in 38% yield: LCMS (ESI) m/z 438 (MH$^+$).

Example 81

Synthesis of 8-Methoxy-2-oxo-2H-chromene-3-carboxylic acid [3-(6-methoxy-naphthalen-2-yl)-phenyl]-amide (78)

DIEA (0.0115 mL, 0.067 mmol) was added to 8-methoxy-3-carboxy-coumarin (0.013 g, 0.06 mmol) and HATU (0.025 g, 0.067 mmol) in 0.5 mL of DMF with constant stirring at room temperature until a clear solution resulted. Subsequently, 3-(6-methoxy-naphthalen-2-yl)-phenylamine (0.015 g, 0.06 mmol) was added and allowed to react overnight when a solid precipitated out of solution. The resulting precipitate was filtered, dried under suction, and finally dried overnight in vacuo to give 0.023 g of product in 83% yield: LCMS (ESI) m/z 452 (MH$^+$).

Example 82

Synthesis of 8-Trifluoromethoxy-2-oxo-2H-chromene-3-carboxylic acid [3-(6-methoxy-naphthalen-2-yl)-phenyl]-amide (79)

DIEA (0.0115 mL, 0.067 mmol) was added to 8-trifluoromethoxy-3-carboxy-coumarin (0.016 g, 0.06 mmol) and HATU (0.025 g, 0.067 mmol) in 0.5 mL of DMF with constant stirring at room temperature until a clear solution resulted. Subsequently, 3-(6-methoxy-naphthalen-2-yl)-phenylamine (0.015 g, 0.06 mmol) was added and allowed to react overnight when a solid precipitated out of solution. The resulting precipitate was filtered, dried under suction, and finally dried overnight in vacuo to give 0.015 g of product in 49% yield: LCMS (ESI) m/z 506 (MH$^+$).

Example 83

Synthesis of 3-Naphthalen-2-yl-phenylamine (34)

Naphthalene-2-boronic acid (0.119 g, 0.693 mmol) and 3-bromoaniline (0.05 mL, 0.462 mmol) in DME (2 mL) were combined in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$O and extracted with CH$_2$Cl$_2$. The organic phase was dried over MgSO$_4$ and concentrated under vacuum. The crude product was purified by silica column chromatography (5-20% EtOAc/hexanes). The purification was monitored by TLC. The solvent was removed under vacuum from fractions containing product, resulting in 0.063 g in 63% yield.

Example 84

Synthesis of 8-Hydroxy-2-oxo-2H-chromene-3-carboxylic acid (3-Naphthalen-2-yl-phenyl)-amide (80)

DIEA (0.013 mL, 0.075 mmol) was added to 8-hydroxy-3-carboxy-coumarin (0.014 g, 0.068 mmol) and HATU (0.029 g, 0.075 mmol) in 0.36 mL of DMF with constant stirring at room temperature until a clear solution resulted. Subsequently, 3-naphthalen-2-yl-phenylamine (0.015 g, 0.068 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and lyophilized for 48 hours to give 0.010 g of product in 36% yield: LCMS (ESI) m/z 408 (MH$^+$).

Example 85

Synthesis of 8-Methoxy-2-oxo-2H-chromene-3-carboxylic acid (3-Naphthalen-2-yl-phenyl)-amide (81)

DIEA (0.013 mL, 0.075 mmol) was added to 8-methoxy-3-carboxy-coumarin (0.015 g, 0.068 mmol) and HATU (0.029 g, 0.075 mmol) in 0.36 mL of DMF with constant stirring at room temperature until a clear solution resulted. Subsequently, 3-naphthalen-2-yl-phenylamine (0.015 g, 0.068 mmol) was added and allowed to react overnight when a solid precipitated out of solution. The resulting precipitate was filtered, dried under suction, and finally dried overnight in vacuo to give 0.025 g of product in 86% yield: LCMS (ESI) m/z 422 (MH$^+$).

Example 86

Synthesis of 8-Trifluoromethoxy-2-oxo-2H-chromene-3-carboxylic acid (3-Naphthalen-2-yl-phenyl)-amide (82)

DIEA (0.013 mL, 0.075 mmol) was added to 8-trifluoromethoxy-3-carboxy-coumarin (0.019 g, 0.068 mmol) and HATU (0.029 g, 0.075 mmol) in 0.36 mL of DMF with constant stirring at room temperature until a clear solution resulted. Subsequently, 3-naphthalen-2-yl-phenylamine (0.015 g, 0.068 mmol) was added and allowed to react overnight when a solid precipitated out of solution. The resulting precipitate was filtered, dried under suction, and finally dried overnight in vacuo to give 0.024 g of product in 63% yield: LCMS (ESI) m/z 476 (MH$^+$).

Example 87

Synthesis of 3-Quinolin-3-yl-phenylamine (35)

Quinoline-3-boronic acid (0.120 g, 0.693 mmol) and 3-bromoaniline (0.05 mL, 0.462 mmol) were combined in dimethoxyethane (DME, 2 mL) in a flame-dried, round-bottom flask. Sodium carbonate (Na$_2$CO$_3$, 2M, 0.485 mL, 0.970 mmol) and tetrakis[triphenylphosphine]palladium(0) (Pd(PPh$_3$)$_4$, 0.017 g, 0.014 mmol) were added to the stirred solution. The reaction was refluxed overnight under argon flow, and subsequently cooled to room temperature. The solvent was removed under vacuum, and the residue was resuspended in H$_2$0 and extracted with methylene chloride (CH$_2$Cl$_2$). The organic phase was dried over magnesium sulfate (MgSO$_4$) and concentrated under vacuum. The crude product was purified by silica column chromatography (0-5% methanol (MeOH)/CH$_2$Cl$_2$). The purification was monitored by thin layer chromatography (TLC). The solvent was removed under vacuum from fractions containing product, resulting in 0.054 g in 53% yield.

Example 88

Synthesis of 8-Hydroxy-2-oxo-2H-chromene-3-carboxylic acid [3-Quinolin-3-yl-phenyl]-amide (83)

DIEA (0.013 mL, 0.075 mmol) was added to 8-hydroxy-3-carboxy-coumarin (0.014 g, 0.068 mmol) and HATU (0.028 g, 0.075 mmol) in 0.36 mL of DMF with constant stirring at room temperature until a clear solution resulted. Subsequently, 3-quinolin-3-yl-phenylamine (0.015 g, 0.068 mmol) was added and allowed to react overnight when a solid precipitated out of solution. The resulting precipitate was filtered, dried under suction, and finally dried overnight in vacuo to give 0.013 g of product in 48% yield: LCMS (ESI) m/z 409 (MH$^+$).

Example 89

Synthesis of 8-Methoxy-2-oxo-2H-chromene-3-carboxylic acid [3-Quinolin-3-yl-phenyl]-amide (84)

DIEA (0.013 mL, 0.075 mmol) was added to 8-methoxy-3-carboxy-coumarin (0.015 g, 0.068 mmol) and HATU (0.028 g, 0.075 mmol) in 0.36 mL of DMF with constant stirring at room temperature until a clear solution resulted. Subsequently, 3-quinolin-3-yl-phenylamine (0.015 g, 0.068 mmol) was added and allowed to react overnight when a solid precipitated out of solution. The resulting precipitate was filtered, dried under suction, and finally dried overnight in vacuo to give 0.017 g of product in 59% yield: LCMS (ESI) m/z 423 (MH$^+$).

Example 90

Synthesis of 8-Trifluoromethoxy-2-oxo-2H-chromene-3-carboxylic acid [3-Quinolin-3-yl-phenyl]-amide (85)

DIEA (0.013 mL, 0.075 mmol) was added to 8-trifluoromethoxy-3-carboxy-coumarin (0.019 g, 0.068 mmol) and HATU (0.028 g, 0.075 mmol) in 0.36 mL of DMF with constant stirring at room temperature until a clear solution resulted. Subsequently, 3-quinolin-3-yl-phenylamine (0.015 g, 0.068 mmol) was added and allowed to react overnight when a solid precipitated out of solution. The resulting precipitate was filtered, dried under suction, and finally dried overnight in vacuo to give 0.022 g of product in 68% yield: LCMS (ESI) m/z 477 (MH$^+$).

Example 91

Synthesis of 3-(2,3-Dihydro-benzo[1,4]dioxin-6-yl)-phenylamine (36)

1,4-benzodioxane-6-boronic acid (0.125 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in H$_2$0 and extracted with CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.079 g in 75% yield.

Example 92

Synthesis of 8-Hydroxy-2-oxo-2H-chromene-3-carboxylic acid [3-(2,3-dihydro-benzo[1,4]dioxin-6-yl)-phenyl]-amide (86)

DIEA (0.013 mL, 0.072 mmol) was added to 8-hydroxy-3-carboxy-coumarin (0.013 g, 0.067 mmol) and HATU (0.028 g, 0.072 mmol) in 0.36 mL of DMF with constant stirring at room temperature until a clear solution resulted. Subsequently, 3-(2,3-dihydro-benzo[1,4]dioxin-6-yl)-phenylamine (0.015 g, 0.067 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and lyophilized for 48 hours to give 0.011 g of product in 39% yield: LCMS (ESI) m/z 416 (MH$^+$).

Example 93

Synthesis of 8-Methoxy-2-oxo-2H-chromene-3-carboxylic acid [3-(2,3-dihydro-benzo[1,4]dioxin-6-yl)-phenyl]-amide (87)

DIEA (0.013 mL, 0.072 mmol) was added to 8-methoxy-3-carboxy-coumarin (0.016 g, 0.067 mmol) and HATU (0.028 g, 0.072 mmol) in 0.36 mL of DMF with constant stirring at room temperature until a clear solution resulted. Subsequently, 3-(2,3-dihydro-benzo[1,4]dioxin-6-yl)-phenylamine (0.015 g, 0.067 mmol) was added and allowed to react overnight when a solid precipitated out of solution. The resulting precipitate was filtered, dried under suction, and finally dried overnight in vacuo to give 0.022 g of product in 79% yield: LCMS (ESI) m/z 430 (MH$^+$).

Example 94

Synthesis of 8-Trifluoromethoxy-2-oxo-2H-chromene-3-carboxylic acid [3-(2,3-dihydro-benzo[1,4]dioxin-6-yl)-phenyl]-amide (88)

DIEA (0.013 mL, 0.072 mmol) was added to 8-trifluoromethoxy-3-carboxy-coumarin (0.020 g, 0.067 mmol) and HATU (0.028 g, 0.072 mmol) in 0.36 mL of DMF with constant stirring at room temperature until a clear solution resulted. Subsequently, 3-(2,3-dihydro-benzo[1,4]dioxin-6-yl)-phenylamine (0.015 g, 0.067 mmol) was added and allowed to react overnight when a solid precipitated out of solution. The resulting precipitate was filtered, dried under suction, and finally dried overnight in vacuo to give 0.022 g of product in 67% yield: LCMS (ESI) m/z 484 (MH$^+$).

Example 95

Synthesis of 2'-cyano-biphenyl-3-ylamine (37)

2-cyanophenyl boronic acid (0.102 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$ and concentrated under vacuum. The crude product was purified by silica column chromatography (0-20% EtOAc/hexanes). The purification was monitored by TLC. The solvent was removed under vacuum from fractions containing product, resulting in 0.071 g in 79% yield.

Example 96

Synthesis of 8-Hydroxy-2-oxo-2H-chromene-3-carboxylic acid (2'-cyano-biphenyl-3-yl)-amide (89)

DIEA (0.015 mL, 0.085 mmol) was added to 8-hydroxy-3-carboxy-coumarin (0.016 g, 0.077 mmol) and HATU (0.032 g, 0.085 mmol) in 0.45 mL of DMF with constant stirring at room temperature until a clear solution resulted. Subsequently, 2'-cyano-biphenyl-3-ylamine (0.015 g, 0.077 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and lyophilized for 48 hours to give 0.008 g of product in 26% yield: LCMS (ESI) m/z 383 (MO.

Example 97

Synthesis of 8-Methoxy-2-oxo-2H-chromene-3-carboxylic acid (2'-cyano-biphenyl-3-yl)-amide (90)

DIEA (0.015 mL, 0.085 mmol) was added to 8-methoxy-3-carboxy-coumarin (0.017 g, 0.077 mmol) and HATU (0.032 g, 0.085 mmol) in 0.45 mL of DMF with constant stirring at room temperature until a clear solution resulted. Subsequently, 2'-cyano-biphenyl-3-ylamine (0.015 g, 0.077 mmol) was added and allowed to react overnight when a solid precipitated out of solution. The resulting precipitate was filtered, dried under suction, and finally dried overnight in vacuo to give 0.026 g of product in 85% yield: LCMS (ESI) m/z 397 (MH$^+$).

Example 98

Synthesis of 8-Trifluoromethoxy-2-oxo-2H-chromene-3-carboxylic acid (2'-cyano-biphenyl-3-yl)-amide (91)

DIEA (0.015 mL, 0.085 mmol) was added to 8-trifluoromethoxy-3-carboxy-coumarin (0.021 g, 0.077 mmol) and HATU (0.032 g, 0.085 mmol) in 0.45 mL of DMF with constant stirring at room temperature until a clear solution resulted. Subsequently, 2'-cyano-biphenyl-3-ylamine (0.015 g, 0.077 mmol) was added and allowed to react overnight when a solid precipitated out of solution. The resulting precipitate was filtered, dried under suction, and finally dried overnight in vacuo to give 0.022 g of product in 63% yield: LCMS (ESI) m/z 451 (MH$^+$).

Example 99

Synthesis of 3-(1H-Indol-5-yl)-phenylamine (38)

Indole-5-boronic acid (0.111 g, 0.693 mmol) and 3-bromoaniline (0.05 mL, 0.462 mmol) were combined in DME (2 mL) in a flame-dried, round-bottom flask. Na$_2$CO$_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$ and concentrated under vacuum. The crude product was purified by silica column chromatography (50-100% EtOAc/hexanes). The purification was monitored by TLC. The solvent was removed under vacuum from fractions containing product, resulting in 0.049 g in 50% yield.

Example 100

Synthesis of 8-Hydroxy-2-oxo-2H-chromene-3-carboxylic acid (3-(1H-Indol-5-yl)-phenyl)-amide (92)

DIEA (0.014 mL, 0.073 mmol) was added to 8-hydroxy-3-carboxy-coumarin (0.015 g, 0.066 mmol) and HATU (0.030 g, 0.073 mmol) in 0.36 mL of DMF with constant stirring at room temperature until a clear solution resulted. Subsequently, 3-(1H-Indol-5-yl)-phenylamine (0.015 g, 0.066 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.017 g of product in 61% yield: LCMS (ESI) m/z 397 ($MH^+$).

Example 101

Synthesis of 8-Methoxy-2-oxo-2H-chromene-3-carboxylic acid (3-(1H-Indol-5-yl)-phenyl)-amide (93)

DIEA (0.014 mL, 0.073 mmol) was added to 8-methoxy-3-carboxy-coumarin (0.016 g, 0.066 mmol) and HATU (0.030 g, 0.073 mmol) in 0.36 mL of DMF with constant stirring at room temperature until a clear solution resulted. Subsequently, 3-(1H-Indol-5-yl)-phenylamine (0.015 g, 0.066 mmol) was added and allowed to react overnight when a solid precipitated out of solution. The resulting precipitate was filtered, dried under suction, and finally dried overnight in vacuo to give 0.017 g of product in 56% yield: LCMS (ESI) m/z 411 ($MH^+$).

Example 102

Synthesis of 8-Trifluoromethoxy-2-oxo-2H-chromene-3-carboxylic acid (3-(1H-Indol-5-yl)-phenyl)-amide (94)

DIEA (0.014 mL, 0.073 mmol) was added to 8-trifluoromethoxy-3-carboxy-coumarin (0.020 g, 0.066 mmol) and HATU (0.030 g, 0.073 mmol) in 0.36 mL of DMF with constant stirring at room temperature until a clear solution resulted. Subsequently, 3-(1H-Indol-5-yl)-phenylamine (0.015 g, 0.066 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected were collected and the solvent removed under vacuum to give 0.023 g of product in 68% yield: LCMS (ESI) m/z 465 ($MH^+$).

Example 103

Synthesis of N-(3'-Amino-biphenyl-2-yl)-acetamide (39)

2-acetylaminophenyl boronic acid (0.124 g, 0.693 mmol) and 3-bromoaniline (0.05 mL, 0.462 mmol) were combined in DME (2 mL) in a flame-dried, round-bottom flask. $Na_2CO_3$ (2M, 0.485 mL, 0.970 mmol) and Pd(PPh$_3$)$_4$ (0.017 g, 0.014 mmol) were added to the stirred solution. The reaction was refluxed overnight under argon flow, and subsequently cooled to room temperature. The solvent was removed under vacuum and the resulting residue was resuspended in $H_2O$ and extracted with $CH_2Cl_2$. The organic phase was dried over $MgSO_4$ and concentrated under vacuum. The crude product was purified by silica column chromatography (0-50% EtOAc/hexanes). The purification was monitored by TLC. The solvent was removed under vacuum from fractions containing product, resulting in 0.103 g in 98% yield.

Example 104

Synthesis of 8-Hydroxy-2-oxo-2H-chromene-3-carboxylic acid (2'-acetylamino-biphenyl-3-yl)-amide (95)

DIEA (0.013 mL, 0.073 mmol) was added to 8-hydroxy-3-carboxy-coumarin (0.014 g, 0.066 mmol) and HATU (0.028 g, 0.073 mmol) in 0.36 mL of DMF with constant stirring at room temperature until a clear solution resulted. Subsequently, N-(3'-Amino-biphenyl-2-yl)-acetamide (0.015 g, 0.066 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.007 g of product in 27% yield: LCMS (ESI) m/z 415 ($MH^+$).

Example 105

Synthesis of 8-Methoxy-2-oxo-2H-chromene-3-carboxylic acid (2'-acetylamino-biphenyl-3-yl)-amide (96)

DIEA (0.013 mL, 0.073 mmol) was added to 8-methoxy-3-carboxy-coumarin (0.015 g, 0.066 mmol) and HATU (0.028 g, 0.073 mmol) in 0.36 mL of DMF with constant stirring at room temperature until a clear solution resulted. Subsequently, N-(3'-Amino-biphenyl-2-yl)-acetamide (0.015 g, 0.066 mmol) was added and allowed to react overnight when a solid precipitated out of solution. The resulting precipitate was filtered, dried under suction, and finally dried overnight in vacuo to give 0.020 g of product in 69% yield: LCMS (ESI) m/z 429 ($MH^+$).

Example 106

Synthesis of 8-Trifluoromethoxy-2-oxo-2H-chromene-3-carboxylic acid (2'-acetylamino-biphenyl-3-yl)-amide (97)

DIEA (0.013 mL, 0.073 mmol) was added to 8-trifluoromethoxy-3-carboxy-coumarin (0.018 g, 0.066 mmol) and HATU (0.028 g, 0.073 mmol) in 0.36 mL of DMF with constant stirring at room temperature until a clear solution resulted. Subsequently, N-(3'-Amino-biphenyl-2-yl)-acetamide (0.015 g, 0.066 mmol) was added and allowed to react overnight and allowed to react overnight when a solid precipitated out of solution. The resulting precipitate was filtered, dried under suction, and finally dried overnight in vacuo to give 0.008 g of product in 26% yield: LCMS (ESI) m/z 483 (MH+).

Example 107

Synthesis of 2'-(Morpholine-4-sulfonyl)-biphenyl-3-ylamine (40)

2-(morpholinosulfonyl)phenylboronic acid (0.188 g, 0.693 mmol) and 3-bromoaniline (0.05 mL, 0.462 mmol) were combined in DME (2 mL) in a flame-dried, round-bottom flask. $Na_2CO_3$ (2M, 0.485 mL, 0.970 mmol) and $Pd(PPh_3)_4$ (0.017 g, 0.014 mmol) were added to the stirred solution. The reaction was refluxed overnight under argon flow, and subsequently cooled to room temperature. The solvent was removed under vacuum and the resulting residue resuspended in $H_2O$ and extracted with $CH_2Cl_2$. The organic phase was dried over $MgSO_4$ and concentrated under vacuum. The crude product was purified by silica column chromatography (5-20% EtOAc/hexanes). The purification was monitored by TLC. The solvent was removed under vacuum from fractions containing product, resulting in 0.113 g in 77% yield.

Example 108

Synthesis of 8-Hydroxy-2-oxo-2H-chromene-3-carboxylic acid (2'-(Morpholine-4-sulfonyl)-biphenyl-3-yl)-amide (98)

DIEA (0.009 mL, 0.052 mmol) was added to 8-hydroxy-3-carboxy-coumarin (0.010 g, 0.047 mmol) and HATU (0.020 g, 0.052 mmol) in 0.36 mL of DMF with constant stirring at room temperature until a clear solution resulted. Subsequently, 2'-(Morpholine-4-sulfonyl)-biphenyl-3-ylamine (0.015 g, 0.047 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% $ACN/H_2O$ with 0.05% TFA at a flow rate of 20 mL/min. UV absorbance was monitored at 254 nm and the fractions corresponding to the product peak were collected and the solvent removed under vacuum to give 0.013 g of product in 53% yield: LCMS (ESI) m/z 507 (MH+).

Example 109

Synthesis of 8-Methoxy-2-oxo-2H-chromene-3-carboxylic acid (2'-(Morpholine-4-sulfonyl)-biphenyl-3-yl)-amide (99)

DIEA (0.009 mL, 0.052 mmol) was added to 8-methoxy-3-carboxy-coumarin (0.010 g, 0.047 mmol) and HATU (0.020 g, 0.052 mmol) in 0.36 mL of DMF with constant stirring at room temperature until a clear solution resulted. Subsequently, 2'-(Morpholine-4-sulfonyl)-biphenyl-3-ylamine (0.015 g, 0.047 mmol) was added and allowed to react overnight when a solid precipitated out of solution. The resulting precipitate was filtered, dried under suction, and finally dried overnight in vacuo to give 0.018 g of product in 73% yield: LCMS (ESI) m/z 521 (MH+).

Example 110

Synthesis of 8-Trifluoromethoxy-2-oxo-2H-chromene-3-carboxylic acid (2'-(Morpholine-4-sulfonyl)-biphenyl-3-yl)-amide (100)

DIEA (0.009 mL, 0.052 mmol) was added to 8-trifluoromethoxy-3-carboxy-coumarin (0.013 g, 0.047 mmol) and HATU (0.020 g, 0.052 mmol) in 0.36 mL of DMF with constant stirring at room temperature until a clear solution resulted. Subsequently, 2'-(Morpholine-4-sulfonyl)-biphenyl-3-ylamine (0.015 g, 0.047 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% $ACN/H_2O$ with 0.05% TFA at a flow rate of 20 mL/min. UV absorbance was monitored at 254 nm and the fractions corresponding to the product peak were collected were collected and the solvent removed under vacuum to give 0.014 g of product in 50% yield: LCMS (ESI) m/z 591 (MH+).

Example 111

Synthesis of 3-(2,4-dimethoxy-pyrimidin-5-yl)-phenylamine (101)

2,4-dimethoxypyrimidine-5-boronic acid (0.160 g, 0.872 mmol) and 3-bromoaniline (0.063 mL, 0.581 mmol) were combined in DME (3 mL) in a flame-dried, round-bottom flask. $Na_2CO_3$ (2M, 0.610 mL, 1.22 mmol) and $Pd(PPh_3)_4$ (0.02 g, 0.017 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.074 g in 55% yield.

Example 112

Synthesis of 8-Hydroxy-2-oxo-2H-chromene-3-carboxylic acid [3-(2,4-dimethoxy-pyrimidin-5-yl)-phenyl]-amide (127)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(2,4-dimethoxy-pyrimidin-5-yl)-phenylamine (0.015 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% $ACN/H_2O$ with 0.05% TFA at a flow rate of 20 mL/min. UV absorbance was monitored at 254 nm and the fractions corresponding to the product peak were collected and the solvent removed under vacuum to give 0.010 g of product in 39% yield: LCMS (ESI) m/z 420 (MH+).

Example 113

Synthesis of 8-Methoxy-2-oxo-2H-chromene-3-carboxylic acid [3-(2,4-dimethoxy-pyrimidin-5-yl)-phenyl]-amide (128)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(2,4-dimethoxy-pyrimidin-5-yl)-phenylamine (0.015 g, 0.065 mmol) was added and allowed to react overnight when a solid precipitated out of solution. The resulting precipitate was filtered, dried under suction, and finally dried overnight in vacuo to give 0.019 g of product in 69% yield: LCMS (ESI) m/z 434 (MH$^+$).

Example 114

Synthesis of 3-(6-methoxy-pyridin-3-yl)-phenylamine (102)

2-methoxypyridine-5-boronic acid (0.133 g, 0.872 mmol) and 3-bromoaniline (0.063 mL, 0.581 mmol) were combined in DME (3 mL) in a flame-dried, round-bottom flask. Na$_2$CO$_3$ (2M, 0.610 mL, 1.22 mmol) and Pd(PPh$_3$)$_4$ (0.02 g, 0.017 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.091 g in 76% yield.

Example 115

Synthesis of 8-Hydroxy-2-oxo-2H-chromene-3-carboxylic acid [3-(6-methoxy-pyridin-3-yl)-phenyl]-amide (129)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(6-methoxy-pyridin-3-yl)-phenylamine (0.013 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.012 g of product in 49% yield: LCMS (ESI) m/z 389 (MH$^+$).

Example 116

Synthesis of 8-Methoxy-2-oxo-2H-chromene-3-carboxylic acid [3-(6-methoxy-pyridin-3-yl)-phenyl]-amide (130)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(6-methoxy-pyridin-3-yl)-phenylamine (0.013 g, 0.065 mmol) was added and allowed to react overnight when a solid precipitated out of solution. The resulting precipitate was filtered, dried under suction, and finally dried overnight in vacuo to give 0.022 g of product in 84% yield: LCMS (ESI) m/z 403 (MH$^+$).

Example 117

Synthesis of 3-(5-methoxy-pyridin-3-yl)-phenylamine (103)

3-methoxypyridine-5-boronic acid pinacol ester (0.205 g, 0.872 mmol) and 3-bromoaniline (0.063 mL, 0.581 mmol) were combined in DME (3 mL) in a flame-dried, round-bottom flask. Na$_2$CO$_3$ (2M, 0.610 mL, 1.22 mmol) and Pd(PPh$_3$)$_4$ (0.02 g, 0.017 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (0-5% MeOH/CH$_2$Cl$_2$). The purification was monitored by TLC. The solvent was removed under vacuum from fractions containing product, resulting in 0.067 g in 58% yield.

Example 118

Synthesis of 8-Hydroxy-2-oxo-2H-chromene-3-carboxylic acid [3-(5-methoxy-pyridin-3-yl)-phenyl]-amide (131)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(5-methoxy-pyridin-3-yl)-phenylamine (0.013 g, 0.065 mmol) was added and allowed to react overnight when a solid precipitated out of solution. The resulting precipitate was filtered, dried under suction, and finally dried overnight in vacuo to give 0.014 g of product in 56% yield: LCMS (ESI) m/z 389 (MH$^+$).

Example 119

Synthesis of 8-Methoxy-2-oxo-2H-chromene-3-carboxylic acid [3-(5-methoxy-pyridin-3-yl)-phenyl]-amide (132)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(5-methoxy-pyridin-3-yl)-phenylamine (0.013 g, 0.065 mmol) was added and allowed to react overnight when a solid precipitated out of solution. The resulting precipitate was filtered, dried under suction, and finally dried overnight in vacuo to give 0.020 g of product in 79% yield: LCMS (ESI) m/z 403 (MH$^+$).

Example 120

Synthesis of
3-(2-methoxy-pyrimidin-5-yl)-phenylamine (104)

2-methoxypyrimidine-5-boronic acid (0.134 g, 0.872 mmol) and 3-bromoaniline (0.063 mL, 0.581 mmol) were combined in DME (3 mL) in a flame-dried, round-bottom flask. $Na_2CO_3$ (2M, 0.610 mL, 1.22 mmol) and $Pd(PPh_3)_4$ (0.02 g, 0.017 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.097 g in 83% yield.

Example 120

Synthesis of 8-Hydroxy-2-oxo-2H-chromene-3-carboxylic acid [3-(2-methoxy-pyrimidin-5-yl)-phenyl]-amide (133)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(2-methoxy-pyrimidin-5-yl)-phenylamine (0.013 g, 0.065 mmol) was added and allowed to react overnight when a solid precipitated out of solution. The resulting precipitate was filtered, dried under suction, and finally dried overnight in vacuo to give 0.005 g of product in 20% yield: LCMS (ESI) m/z 390 (MH$^+$).

Example 121

Synthesis of 8-Methoxy-2-oxo-2H-chromene-3-carboxylic acid [3-(2-methoxy-pyrimidin-5-yl)-phenyl]-amide (134)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(2-methoxy-pyrimidin-5-yl)-phenylamine (0.013 g, 0.065 mmol) was added and allowed to react overnight when a solid precipitated out of solution. The resulting precipitate was filtered, dried under suction, and finally dried overnight in vacuo to give 0.012 g of product in 48% yield: LCMS (ESI) m/z 404 (MH$^+$).

Example 122

Synthesis of 3-pyrimidin-5-yl-phenylamine (105)

5-pyrimidinyl-boronic acid (0.108 g, 0.872 mmol) and 3-bromoaniline (0.063 mL, 0.581 mmol) were combined in DME (3 mL) in a flame-dried, round-bottom flask. $Na_2CO_3$ (2M, 0.610 mL, 1.22 mmol) and $Pd(PPh_3)_4$ (0.02 g, 0.017 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.031 g in 31% yield.

Example 123

Synthesis of 8-Hydroxy-2-oxo-2H-chromene-3-carboxylic acid (3-pyrimidin-5-yl-phenyl)-amide (135)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-pyrimidin-5-yl-phenylamine (0.011 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.002 g of product in 9% yield: LCMS (ESI) m/z 360 (MH$^+$).

Example 124

Synthesis of 8-Methoxy-2-oxo-2H-chromene-3-carboxylic acid (3-pyrimidin-5-yl-phenyl)-amide (136)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-pyrimidin-5-yl-phenylamine (0.011 g, 0.065 mmol) was added and allowed to react overnight when a solid precipitated out of solution. The resulting precipitate was filtered, dried under suction, and finally dried overnight in vacuo to give 0.015 g of product in 62% yield: LCMS (ESI) m/z 374 (MH$^+$).

Example 125

Synthesis of
3-(6-dimethylamino-pyridin-3-yl)-phenylamine (106)

2-(dimethylamino)-pyridine-5-boronic acid hydrate (0.145 g, 0.872 mmol) and 3-bromoaniline (0.063 mL, 0.581 mmol) were combined in DME (3 mL) in a flame-dried, round-bottom flask. $Na_2CO_3$ (2M, 0.610 mL, 1.22 mmol) and $Pd(PPh_3)_4$ (0.02 g, 0.017 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.067 g in 54% yield.

Example 126

Synthesis of 8-Hydroxy-2-oxo-2H-chromene-3-carboxylic acid [3-(6-dimethylamino-pyridin-3-yl)-phenyl]-amide (137)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(6-dimethylamino-pyridin-3-yl)-phenylamine (0.014 g, 0.065 mmol) was added and allowed to react overnight when a solid precipitated out of solution. The resulting precipitate was filtered, dried under suction, and finally dried overnight in vacuo to give 0.011 g of product in 42% yield: LCMS (ESI) m/z 402 (MH+).

Example 127

Synthesis of 8-Methoxy-2-oxo-2H-chromene-3-carboxylic acid [3-(6-dimethylamino-pyridin-3-yl)-phenyl]-amide (138)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(6-dimethylamino-pyridin-3-yl)-phenylamine (0.014 g, 0.065 mmol) was added and allowed to react overnight when a solid precipitated out of solution. The resulting precipitate was filtered, dried under suction, and finally dried overnight in vacuo to give 0.018 g of product in 66% yield: LCMS (ESI) m/z 416 (MH+).

Example 128

Synthesis of 3-(6-hydroxy-pyridin-3-yl)-phenylamine (107)

3-hydroxypyridine-5-boronic acid pinacol ester (0.193 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (0-10% MeOH/$CH_2Cl_2$). The purification was monitored by TLC. The solvent was removed under vacuum from fractions containing product, resulting in 0.013 g in 12% yield.

Example 129

8-Hydroxy-2-oxo-2H-chromene-3-carboxylic acid [3-(6-hydroxy-pyridin-3-yl)-phenyl]-amide (139)

DIEA (0.008 mL, 0.048 mmol) was added to 8-hydroxy-3-carboxy-coumarin (0.009 g, 0.043 mmol) and HATU (0.018 g, 0.048 mmol) in 0.5 mL of DMF with constant stirring at room temperature until a clear solution resulted. Subsequently, 3-(6-hydroxy-pyridin-3-yl)-phenylamine (0.008 g, 0.043 mmol) was added and allowed to react overnight when a solid precipitated out of solution. The resulting precipitate was filtered, dried under suction, and finally dried overnight in vacuo to give 0.003 g of product in 15% yield: LCMS (ESI) m/z 375 (MH+).

Example 130

Synthesis of 8-Methoxy-2-oxo-2H-chromene-3-carboxylic acid [3-(6-hydroxy-pyridin-3-yl)-phenyl]-amide (140)

DIEA (0.008 mL, 0.048 mmol) was added to 8-methoxy-3-carboxy-coumarin (0.009 g, 0.043 mmol) and HATU (0.018 g, 0.048 mmol) in 0.5 mL of DMF with constant stirring at room temperature until a clear solution resulted. Subsequently, 3-(6-hydroxy-pyridin-3-yl)-phenylamine (0.008 g, 0.043 mmol) was added and allowed to react overnight when a solid precipitated out of solution. The resulting precipitate was filtered, dried under suction, and finally dried overnight in vacuo to give 0.003 g of product in 21% yield: LCMS (ESI) m/z 389 (MH+).

Example 131

Synthesis of 3-(2-methoxy-pyridin-3-yl)-phenylamine (108)

2-methoxypyridine-3-boronic acid hydrate (0.133 g, 0.872 mmol) and 3-bromoaniline (0.063 mL, 0.581 mmol) were combined in DME (3 mL) in a flame-dried, round-bottom flask. $Na_2CO_3$ (2M, 0.610 mL, 1.22 mmol) and $Pd(PPh_3)_4$ (0.02 g, 0.017 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.092 g in 80% yield.

Example 132

Synthesis of 8-Hydroxy-2-oxo-2H-chromene-3-carboxylic acid [3-(2-methoxy-pyridin-3-yl)-phenyl]-amide (141)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(2-methoxy-pyridin-3-yl)-phenylamine (0.013 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.013 g of product in 54% yield: LCMS (ESI) m/z 389 (MH+).

Example 133

Synthesis of 8-Methoxy-2-oxo-2H-chromene-3-carboxylic acid [3-(2-methoxy-pyridin-3-yl)-phenyl]-amide (142)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(2-methoxy-pyridin-3-yl)-phenylamine (0.013 g, 0.065 mmol) was added and allowed to react overnight when a solid precipitated out of solution. The resulting precipitate was filtered, dried under suction, and finally dried overnight in vacuo to give 0.024 g of product in 92% yield: LCMS (ESI) m/z 403 (MH$^+$).

Example 134

Synthesis of 4'-cyano-3'-fluoro-biphenyl-3-ylamine (109)

4-cyano-3-fluorophenyl boronic acid (0.144 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (5-60% EtOAc/hexanes). The purification was monitored by TLC. The solvent was removed under vacuum from fractions containing product, resulting in 0.120 g in 98% yield.

Example 135

Synthesis of 8-Hydroxy-2-oxo-2H-chromene-3-carboxylic acid (4'-cyano-3'-fluoro-biphenyl-3-yl)-amide (143)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 4'-cyano-3'-fluoro-biphenyl-3-ylamine (0.014 g, 0.065 mmol) was added and allowed to react overnight when a solid precipitated out of solution. The resulting precipitate was filtered, dried under suction, and finally dried overnight in vacuo to give 0.004 g of product in 15% yield: LCMS (ESI) m/z 401 (MH$^+$).

Example 136

Synthesis of 8-Methoxy-2-oxo-2H-chromene-3-carboxylic acid (4'-cyano-3'-fluoro-biphenyl-3-yl)-amide (144)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 4'-cyano-3'-fluoro-biphenyl-3-ylamine (0.014 g, 0.065 mmol) was added and allowed to react overnight when a solid precipitated out of solution. The resulting precipitate was filtered, dried under suction, and finally dried overnight in vacuo to give 0.021 g of product in 81% yield: LCMS (ESI) m/z 415 (MH$^+$).

Example 137

Synthesis of 3'-cyano-4'-fluoro-biphenyl-3-ylamine (110)

3-cyano-4-fluorophenyl boronic acid (0.144 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (5-60% EtOAc/hexanes). The purification was monitored by TLC. The solvent was removed under vacuum from fractions containing product, resulting in 0.099 g in 81% yield.

Example 138

Synthesis of 8-Hydroxy-2-oxo-2H-chromene-3-carboxylic acid (3'-cyano-4'-fluoro-biphenyl-3-yl)-amide (145)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3'-cyano-4'-fluoro-biphenyl-3-ylamine (0.014 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.011 g of product in 46% yield: LCMS (ESI) m/z 401 (MH$^+$).

Example 139

Synthesis of 8-Methoxy-2-oxo-2H-chromene-3-carboxylic acid (3'-cyano-4'-fluoro-biphenyl-3-yl)-amide (146)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3'-cyano-4'-fluoro-biphenyl-3-ylamine (0.014 g, 0.065 mmol) was added and allowed to react overnight when a solid precipitated out of solution. The resulting precipitate was filtered, dried under suction, and finally dried overnight in vacuo to give 0.021 g of product in 82% yield: LCMS (ESI) m/z 415 (MH$^+$).

Example 140

Synthesis of 3'-cyano-biphenyl-3-ylamine (111)

3-cyanophenyl boronic acid (0.131 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.085 g in 75% yield.

Example 141

Synthesis of 8-Hydroxy-2-oxo-2H-chromene-3-carboxylic acid (3'-cyano-biphenyl-3-yl)-amide (147)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3'-cyano-biphenyl-3-ylamine (0.013 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.012 g of product in 49% yield: LCMS (ESI) m/z 383 (MH$^+$).

Example 142

Synthesis of 8-Methoxy-2-oxo-2'-chromene-3-carboxylic acid (3'-cyano-biphenyl-3-yl)-amide (148)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3'-cyano-biphenyl-3-ylamine (0.013 g, 0.065 mmol) was added and allowed to react overnight when a solid precipitated out of solution. The resulting precipitate was filtered, dried under suction, and finally dried overnight in vacuo to give 0.021 g of product in 84% yield: LCMS (ESI) m/z 397 (MH$^+$).

Example 143

Synthesis of 3-(1H-pyrazol-4-yl)-phenylamine (112)

1H-pyrazole-4-boronic acid (0.0976 g, 0.639 mmol) and 3-bromoaniline (0.063 mL, 0.581 mmol) were combined in dioxane (2 mL) in a flame-dried, round-bottom flask. K$_3$PO$_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (0-10% MeOH/CH$_2$Cl$_2$). The purification was monitored by TLC. The solvent was removed under vacuum from fractions containing product, resulting in 0.024 g in 26% yield.

Example 144

Synthesis of 8-Hydroxy-2-oxo-2H-chromene-3-carboxylic acid [3-(1H-pyrazol-4-yl)-phenyl]-amide (149)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(1H-pyrazol-4-yl)-phenylamine (0.011 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.002 g of product in 11% yield: LCMS (ESI) m/z 348 (MH$^+$).

Example 145

Synthesis of 8-Methoxy-2-oxo-2H-chromene-3-carboxylic acid [3-(1H-pyrazol-4-yl)-phenyl]-amide (150)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(1H-pyrazol-4-yl)-phenylamine (0.011 g, 0.065 mmol) was added and allowed to react overnight when a solid precipitated out of solution. The resulting precipitate was filtered, dried under suction, and finally dried overnight in vacuo to give 0.006 g of product in 24% yield: LCMS (ESI) m/z 362 (MH$^+$).

Example 146

Synthesis of 3-(2-methyl-2H-pyrazol-3-yl)-phenylamine (113)

1-methyl-1H-pyrazole-5-boronic acid pinacol ester (0.181 g, 0.872 mmol) and 3-bromoaniline (0.063 mL, 0.581 mmol) were combined in dioxane (2 mL) in a flame-dried, round-bottom flask. K$_3$PO$_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.048 g in 47% yield.

Example 147

Synthesis of 8-Hydroxy-2-oxo-2H-chromene-3-carboxylic acid [3-(2-methyl-2H-pyrazol-3-yl)-phenyl]-amide (151)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(2-methyl-2H-pyrazol-3-yl)-phenylamine (0.011 g, 0.065 mmol) was added and allowed to react overnight when a solid precipitated out of solution. The resulting precipitate was filtered, dried under suction, and finally dried overnight in vacuo to give 0.010 g of product in 44% yield: LCMS (ESI) m/z 362 (MH$^+$).

Example 148

Synthesis of 8-Methoxy-2-oxo-2H-chromene-3-carboxylic acid [3-(2-methyl-2H-pyrazol-3-yl)-phenyl]-amide (152)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(2-methyl-2H-pyrazol-3-yl)-phenylamine (0.011 g, 0.065 mmol) was added and allowed to react overnight when a solid precipitated out of solution. The resulting precipitate was filtered, dried under suction, and finally dried overnight in vacuo to give 0.018 g of product in 77% yield: LCMS (ESI) m/z 376 (MH$^+$).

Example 149

Synthesis of 3-(3,5-dimethyl-isoxazol-4-yl)-phenylamine (114)

3,5-dimethylisoxazole-4-boronic acid (0.123 g, 0.872 mmol) and 3-bromoaniline (0.063 mL, 0.581 mmol) were combined in DME (2 mL) in a flame-dried, round-bottom flask. Na$_2$CO$_3$ (2M, 0.610 mL, 1.22 mmol) and Pd(PPh$_3$)$_4$ (0.02 g, 0.017 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (10-60% EtOAc/hexanes). The purification was monitored by TLC. The solvent was removed under vacuum from fractions containing product, resulting in 0.077 g in 71% yield.

Example 150

Synthesis of 8-Hydroxy-2-oxo-2H-chromene-3-carboxylic acid [3-(3,5-dimethyl-isoxazol-4-yl)-phenyl]-amide (153)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(3,5-dimethyl-isoxazol-4-yl)-phenylamine (0.012 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.015 g of product in 61% yield: LCMS (ESI) m/z 377 (MH$^+$).

Example 151

Synthesis of 8-Methoxy-2-oxo-2H-chromene-3-carboxylic acid [3-(3,5-dimethyl-isoxazol-4-yl)-phenyl]-amide (154)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(3,5-dimethyl-isoxazol-4-yl)-phenylamine (0.012 g, 0.065 mmol) was added and allowed to react overnight when a solid precipitated out of solution. The resulting precipitate was filtered, dried under suction, and finally dried overnight in vacuo to give 0.020 g of product in 80% yield: LCMS (ESI) m/z 391 (MH$^+$).

Example 152

Synthesis of 3-(2H-pyrazol-3-yl)-phenylamine (115)

1H-pyrazole-5-boronic acid (0.072 g, 0.639 mmol) and 3-bromoaniline (0.063 mL, 0.581 mmol) were combined in dioxane (2 mL) in a flame-dried, round-bottom flask. K$_3$PO$_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (70-100% EtOAc/hexanes). The purification was monitored by TLC. The solvent was removed under vacuum from fractions containing product, resulting in 0.018 g in 20% yield.

Example 153

Synthesis of 8-Hydroxy-2-oxo-2H-chromene-3-carboxylic acid [3-(2H-pyrazol-3-yl)-phenyl]-amide (155)

DIEA (0.011 mL, 0.062 mmol) was added to 8-hydroxy-3-carboxy-coumarin (0.012 g, 0.057 mmol) and HATU (0.024 g, 0.062 mmol) in 0.5 mL of DMF with constant stirring at room temperature until a clear solution resulted. Subsequently, 3-(2H-pyrazol-3-yl)-phenylamine (0.009 g, 0.057 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.0014 g of product in 7% yield: LCMS (ESI) m/z 348 (MH$^+$).

Example 154

Synthesis of 8-Methoxy-2-oxo-2H-chromene-3-carboxylic acid [3-(2H-pyrazol-3-yl)-phenyl]-amide (156)

DIEA (0.011 mL, 0.062 mmol) was added to 8-methoxy-3-carboxy-coumarin (0.012 g, 0.057 mmol) and HATU (0.024 g, 0.062 mmol) in 0.5 mL of DMF with constant stirring at room temperature until a clear solution resulted. Subsequently, 3-(2H-pyrazol-3-yl)-phenylamine (0.009 g, 0.057 mmol) was added and allowed to react overnight when a solid precipitated out of solution. The resulting precipitate was filtered, dried under suction, and finally dried overnight in vacuo to give 0.0014 g of product in 7% yield: LCMS (ESI) m/z 362 (MH$^+$).

Example 155

Synthesis of 3-(2-oxo-2,3-dihydro-1H-benzoimidazol-5-yl)-phenylamine (116)

2-oxo-2,3-dihydro-1H-benzoimidazole-5-boronic acid pinacol ester (0.227 g, 0.872 mmol) and 3-bromoaniline (0.063 mL, 0.581 mmol) were combined in dioxane (2 mL) in a flame-dried, round-bottom flask. K$_3$PO$_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (0-20% MeOH/CH$_2$Cl$_2$). The purification was monitored by TLC. The solvent was removed under vacuum from fractions containing product, resulting in 0.021 g in 15% yield.

Example 156

Synthesis of 8-Hydroxy-2-oxo-2H-chromene-3-carboxylic acid [3-(2-oxo-2,3-dihydro-1H-benzoimidazol-5-yl)-phenyl]-amide (157)

DIEA (0.0085 mL, 0.049 mmol) was added to 8-hydroxy-3-carboxy-coumarin (0.009 g, 0.044 mmol) and HATU (0.019 g, 0.049 mmol) in 0.3 mL of DMF with constant stirring at room temperature until a clear solution resulted. Subsequently, 33-(2-oxo-2,3-dihydro-1H-benzoimidazol-5-yl)-phenylamine (0.009 g, 0.044 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.0014 g of product in 8% yield: LCMS (ESI) m/z 414 (MH$^+$).

Example 157

Synthesis of 8-Methoxy-2-oxo-2H-chromene-3-carboxylic acid [3-(2-oxo-2,3-dihydro-1H-benzoimidazol-5-yl)-phenyl]-amide (158)

DIEA (0.0085 mL, 0.049 mmol) was added to 8-methoxy-3-carboxy-coumarin (0.009 g, 0.044 mmol) and HATU (0.019 g, 0.049 mmol) in 0.3 mL of DMF with constant stirring at room temperature until a clear solution resulted. Subsequently, 3-(2-oxo-2,3-dihydro-1H-benzoimidazol-5-yl)-phenylamine (0.009 g, 0.044 mmol) was added and allowed to react overnight when a solid precipitated out of solution. The resulting precipitate was filtered, dried under suction, and finally dried overnight in vacuo to give 0.007 g of product in 39% yield: LCMS (ESI) m/z 428 (MH$^+$).

Example 158

Synthesis of 3-benzo[1,2,5]oxadiazol-5-yl-phenylamine (117)

2,4-dimethoxypyrimidine-5-boronic acid (0.143 g, 0.872 mmol) and 3-bromoaniline (0.063 mL, 0.581 mmol) were combined in DME (3 mL) in a flame-dried, round-bottom flask. Na$_2$CO$_3$ (2M, 0.610 mL, 1.22 mmol) and Pd(PPh$_3$)$_4$ (0.02 g, 0.017 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by silica column chromatography (10-100% EtOAc/hexanes). The purification was monitored by TLC. The solvent was removed under vacuum from fractions containing product, resulting in 0.078 g in 63% yield.

Example 159

Synthesis of 8-Hydroxy-2-oxo-2H-chromene-3-carboxylic acid (3-benzo[1,2,5]oxadiazol-5-yl-phenyl)-amide (159)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-benzo[1,2,5]oxadiazol-5-yl-phenylamine (0.014 g, 0.065 mmol) was added and allowed to react overnight when a solid precipitated out of solution. The resulting precipitate was filtered, dried under suction, and finally dried overnight in vacuo to give 0.005 g of product in 18% yield: LCMS (ESI) m/z 400 (MH$^+$).

Example 160

Synthesis of 8-Methoxy-2-oxo-2H-chromene-3-carboxylic acid (3-benzo[1,2,5]oxadiazol-5-yl-phenyl)-amide (160)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-benzo[1,2,5]oxadiazol-5-yl-phenylamine (0.014 g, 0.065 mmol) was added and allowed to react overnight when a solid precipitated out of solution. The resulting precipitate was filtered, dried under suction, and finally dried overnight in vacuo to give 0.023 g of product in 88% yield: LCMS (ESI) m/z 414 (MH$^+$).

Example 161

Synthesis of 3-(4-oxo-4H-chromen-6-yl)-phenylamine (118)

Chromone-6-boronic acid pinacol ester (0.237 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (0-100% EtOAc/hexanes). The purification was monitored by TLC. The solvent was removed under vacuum from fractions containing product, resulting in 0.059 g in 43% yield.

Example 162

Synthesis of 8-Hydroxy-2-oxo-2H-chromene-3-carboxylic acid [3-(4-oxo-4H-chromen-6-yl)-phenyl]-amide (161)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(4-oxo-4H-chromen-6-yl)-phenylamine (0.015 g, 0.065 mmol) was added and allowed to react overnight when a solid precipitated out of solution. The resulting precipitate was filtered, dried under suction, and finally dried overnight in vacuo to give 0.007 g of product in 27% yield: LCMS (ESI) m/z 426 (MH+).

Example 163

Synthesis of 8-Methoxy-2-oxo-2H-chromene-3-carboxylic acid [3-(4-oxo-4H-chromen-6-yl)-phenyl]-amide (162)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(4-oxo-4H-chromen-6-yl)-phenylamine (0.015 g, 0.065 mmol) was added and allowed to react overnight when a solid precipitated out of solution. The resulting precipitate was filtered, dried under suction, and finally dried overnight in vacuo to give 0.028 g of product in 100% yield: LCMS (ESI) m/z 440 (MH+).

Example 164

Synthesis of 3-(1-methyl-1H-indol-5-yl)-phenylamine (119)

1-methylindole-5-boronic acid pinacol ester (0.224 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (5-60% EtOAc/hexanes). The purification was monitored by TLC. The solvent was removed under vacuum from fractions containing product, resulting in 0.059 g in 46% yield.

Example 165

Synthesis of 8-Hydroxy-2-oxo-2H-chromene-3-carboxylic acid [3-(1-methyl-1H-indol-5-yl)-phenyl]-amide (163)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(1-methyl-1H-indol-5-yl)-phenylamine (0.014 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.012 g of product in 48% yield: LCMS (ESI) m/z 411 (MH+).

Example 166

Synthesis of 8-Methoxy-2-oxo-2H-chromene-3-carboxylic acid [3-(1-methyl-1H-indol-5-yl)-phenyl]-amide (164)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(1-methyl-1H-indol-5-yl)-phenylamine (0.014 g, 0.065 mmol) was added and allowed to react overnight when a solid precipitated out of solution. The resulting precipitate was filtered, dried under suction, and finally dried overnight in vacuo to give 0.013 g of product in 46% yield: LCMS (ESI) m/z 425 (MH+).

Example 167

Synthesis of 3-(1H-indol-6-yl)-phenylamine (120)

Indole-6-boronic acid (0.140 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (5-60% EtOAc/hexanes). The purification was monitored by TLC. The solvent was removed under vacuum from fractions containing product, resulting in 0.096 g in 79% yield.

Example 168

Synthesis of 8-Hydroxy-2-oxo-2H-chromene-3-carboxylic acid [3-(1H-indol-6-yl)-phenyl]-amide (165)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(1H-indol-6-yl)-phenylamine (0.014 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.015 g of product in 58% yield: LCMS (ESI) m/z 397 (MH$^+$).

Example 169

Synthesis of 8-Methoxy-2-oxo-2H-chromene-3-carboxylic acid [3-(1H-indol-6-yl)-phenyl]-amide (166)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(1H-indol-6-yl)-phenylamine (0.014 g, 0.065 mmol) was added and allowed to react overnight when a solid precipitated out of solution. The resulting precipitate was filtered, dried under suction, and finally dried overnight in vacuo to give 0.014 g of product in 53% yield: LCMS (ESI) m/z 411 (MH$^+$).

Example 170

Synthesis of 3-(1H-indol-4-yl)-phenylamine (121)

Indole-4-boronic acid (0.140 g, 0.872 mmol) and 3-bromoaniline (0.063 mL, 0.581 mmol) were combined in dioxane (2 mL) in a flame-dried, round-bottom flask. K$_3$PO$_4$ (1.27M, 0.778 mL, 0.99 mmol), PCy$_3$ (0.004 g, 0.014 mmol), and Pd$_2$(dba)$_3$ (0.005 g, 0.006 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (5-60% EtOAc/hexanes). The purification was monitored by TLC. The solvent was removed under vacuum from fractions containing product, resulting in 0.094 g in 78% yield.

Example 171

Synthesis of 8-Hydroxy-2-oxo-2H-chromene-3-carboxylic acid [3-(1H-indol-4-yl)-phenyl]-amide (167)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(1H-indol-4-yl)-phenylamine (0.014 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.013 g of product in 52% yield: LCMS (ESI) m/z 397 (MH$^+$).

Example 172

Synthesis of 8-Methoxy-2-oxo-2H-chromene-3-carboxylic acid [3-(1H-indol-4-yl)-phenyl]-amide (168)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(1H-indol-4-yl)-phenylamine (0.014 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.018 g of product in 70% yield: LCMS (ESI) m/z 411 (MH$^+$).

Example 173

Synthesis of 3-(1-benzyl-1H-pyrazol-4-yl)-phenylamine (122)

1-benzyl-1H-pyrazole-4-boronic acid (0.176 g, 0.872 mmol) and 3-bromoaniline (0.063 mL, 0.581 mmol) were combined in DME (3 mL) in a flame-dried, round-bottom flask. Na$_2$CO$_3$ (2M, 0.610 mL, 1.22 mmol) and Pd(PPh$_3$)$_4$ (0.02 g, 0.017 mmol) were added to the stirred solution. The reaction was refluxed overnight under argon flow, and subsequently cooled to room temperature. The solvent was removed under vacuum and the resulting residue was resuspended in CH$_2$Cl$_2$. The organic phase was dried over MgSO$_4$, filtered, and concentrated under vacuum. The crude product was purified by flash silica column chromatography (10-100% EtOAc/hexanes). The purification was monitored by TLC. The solvent was removed under vacuum from fractions containing product, resulting in 0.137 g in 94% yield.

Example 174

Synthesis of 8-Hydroxy-2-oxo-2H-chromene-3-carboxylic acid [3-(1-benzyl-1H-pyrazol-4-yl)-phenyl]-amide (169)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(1-benzyl-1H-pyrazol-4-yl)-phenylamine (0.016 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/H$_2$O with 0.05% TFA at a flow rate of 20 mL/min. UV absorbance was monitored at 254 nm and the fractions corresponding to the product peak were collected and the solvent removed under vacuum to give 0.015 g of product in 55% yield: LCMS (ESI) m/z 438 (MH$^+$).

Example 175

Synthesis of 8-Methoxy-2-oxo-2H-chromene-3-carboxylic acid [3-(1-benzyl-1H-pyrazol-4-yl)-phenyl]-amide (170)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(1-benzyl-1H-pyrazol-4-yl)-phenylamine (0.016 g, 0.065 mmol) was added and allowed to react overnight when a solid precipitated out of solution. The resulting precipitate was filtered, dried under suction, and finally dried overnight in vacuo to give 0.018 g of product in 62% yield: LCMS (ESI) m/z 452 (MH$^+$).

Example 176

Synthesis of 3-(1-methyl-1H-pyrazol-4-yl)-phenylamine (123)

1-methyl-1H-pyrazole-4-boronic acid pinacol ester (0.098 g, 0.639 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (0-10% MeOH/$CH_2Cl_2$). The purification was monitored by TLC. The solvent was removed under vacuum from fractions containing product, resulting in 0.095 g in 94% yield.

Example 177

Synthesis of 8-Hydroxy-2-oxo-2H-chromene-3-carboxylic acid [3-(1-methyl-1H-pyrazol-4-yl)-phenyl]-amide (171)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3-(1-methyl-1H-pyrazol-4-yl)-phenylamine (0.011 g, 0.065 mmol) was added and allowed to react overnight when a solid precipitated out of solution. The resulting precipitate was filtered, dried under suction, and finally dried overnight in vacuo to give 0.009 g of product in 39% yield: LCMS (ESI) m/z 362 (MH$^+$).

Example 178

Synthesis of 8-Methoxy-2-oxo-2H-chromene-3-carboxylic acid [3-(1-methyl-1H-pyrazol-4-yl)-phenyl]-amide (172)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 3-(1-methyl-1H-pyrazol-4-yl)-phenylamine (0.011 g, 0.065 mmol) was added and allowed to react overnight when a solid precipitated out of solution. The resulting precipitate was filtered, dried under suction, and finally dried overnight in vacuo to give 0.017 g of product in 71% yield: LCMS (ESI) m/z 376 (MH$^+$).

Example 179

Synthesis of 2-(3-Amino-phenyl)-pyrrole-1-carboxylic acid tert-butyl ester (124)

1-N-Boc-pyrrole-2-boronic acid (0.184 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (5-60% EtOAc/hexanes). The purification was monitored by TLC. The solvent was removed under vacuum from fractions containing product, resulting in 0.037 g in 25% yield.

Example 180

Synthesis of 2-{3-[(8-Hydroxy-2-oxo-2H-chromene-3-carbonyl)-amino]-phenyl}-pyrrole-1-carboxylic acid tert-butyl ester (173)

DIEA (0.009 mL, 0.053 mmol) was added to 8-hydroxy-3-carboxy-coumarin (0.010 g, 0.048 mmol) and HATU (0.02 g, 0.053 mmol) in 0.5 mL of DMF with constant stirring at room temperature until a clear solution resulted. Subsequently, 2-(3-Amino-phenyl)-pyrrole-1-carboxylic acid tert-butyl ester (0.013 g, 0.048 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.014 g of product in 62% yield: LCMS (ESI) m/z 447 (MH$^+$).

Example 181

Synthesis of 2-{3-[(8-Methoxy-2-oxo-2H-chromene-3-carbonyl)-amino]-phenyl}-pyrrole-1-carboxylic acid tert-butyl ester (174)

DIEA (0.009 mL, 0.053 mmol) was added to 8-methoxy-3-carboxy-coumarin (0.010 g, 0.048 mmol) and HATU (0.02 g, 0.053 mmol) in 0.5 mL of DMF with constant stirring at room temperature until a clear solution resulted. Subsequently, 2-(3-Amino-phenyl)-pyrrole-1-carboxylic acid tert-butyl ester (0.013 g, 0.048 mmol) was added and allowed to react overnight when a solid precipitated out of solution. The resulting precipitate was filtered, dried under suction, and finally dried overnight in vacuo to give 0.007 g of product in 29% yield: LCMS (ESI) m/z 461 (MH$^+$).

Example 182

Synthesis of 2-(3-Amino-phenyl)-indole-1-carboxylic acid tert-butyl ester (125)

1-(N-Boc)-indole-2-boronic acid (0.228 g, 0.872 mmol) and 3-bromoaniline (0.063 mL, 0.581 mmol) were combined in dioxane (2 mL) in a flame-dried, round-bottom flask. $K_3PO_4$ (1.27M, 0.778 mL, 0.99 mmol), $PCy_3$ (0.004 g, 0.014 mmol), and $Pd_2(dba)_3$ (0.005 g, 0.006 mmol) were added to the stirred solution. The reaction was refluxed overnight under argon flow, and subsequently cooled to room temperature. The solvent was removed under vacuum and the resulting residue was resuspended in $CH_2Cl_2$. The organic phase was dried over $MgSO_4$, filtered, and concentrated under vacuum. The crude product was purified by flash silica column chromatography (100% $CH_2Cl_2$). The purification was monitored by TLC. The solvent was removed under vacuum from fractions containing product, resulting in 0.078 g in 44% yield.

Example 183

Synthesis of 2-{3-[(8-Hydroxy-2-oxo-2H-chromene-3-carbonyl)-amino]-phenyl}-indole-1-carboxylic acid tert-butyl ester (175)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 2-(3-Amino-phenyl)-indole-1-carboxylic acid tert-butyl ester (0.02 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.02 g of product in 64% yield: LCMS (ESI) m/z 497 ($MH^+$).

Example 184

Synthesis of 2-{3-[(8-Methoxy-2-oxo-2H-chromene-3-carbonyl)-amino]-phenyl}-indole-1-carboxylic acid tert-butyl ester (176)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 2-(3-Amino-phenyl)-indole-1-carboxylic acid tert-butyl ester (0.02 g, 0.065 mmol) was added and allowed to react overnight when a solid precipitated out of solution. The resulting precipitate was filtered, dried under suction, and finally dried overnight in vacuo to give 0.024 g of product in 76% yield: LCMS (ESI) m/z 511 ($MH^+$).

Example 185

Synthesis of 3',5'-difluoro-biphenyl-3-ylamine (126)

3,5-difluorophenyl-boronic acid (0.138 g, 0.872 mmol) and 3-bromoaniline (0.063 mL, 0.581 mmol) were combined in DME (3 mL) in a flame-dried, round-bottom flask. $Na_2CO_3$ (2M, 0.610 mL, 1.22 mmol) and $Pd(PPh_3)_4$ (0.02 g, 0.017 mmol) were added to the stirred solution. The reaction was refluxed overnight under argon flow, and subsequently cooled to room temperature. The solvent was removed under vacuum and the resulting residue was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the solvent was removed under vacuum from fractions containing product.

Example 188

Synthesis of 8-Hydroxy-2-oxo-2H-chromene-3-carboxylic acid (3',5'-difluoro-biphenyl-3-yl)-amide (177)

DIEA (0.012 mL, 0.071 mmol) was added to 8-hydroxy-3-carboxy-coumarin (0.013 g, 0.065 mmol) and HATU (0.027 g, 0.071 mmol) in 0.5 mL of DMF with constant stirring at room temperature until a clear solution resulted. Subsequently, 3',5'-difluoro-biphenyl-3-ylamine (0.013 g, 0.065 mmol) was added and allowed to react overnight. DMF was removed under vacuum and the reaction was resuspended in DMSO. The crude product was purified on a Parallex Flex parallel preparative reverse phase HPLC instrument (Biotage) using a solvent gradient of 10-95% ACN/$H_2O$ with 0.05% TFA at a flow rate of 20 mL/min. UV absorbance was monitored at 254 nm and the fractions corresponding to the product peak were collected and the solvent removed under vacuum to give 0.009 g of product in 35% yield: LCMS (ESI) m/z 394 ($MH^+$).

Example 189

Synthesis of 8-Methoxy-2-oxo-2H-chromene-3-carboxylic acid (3',5'-difluoro-biphenyl-3-yl)-amide (178)

DIEA (0.012 mL, 0.071 mmol) was added to 8-methoxy-3-carboxy-coumarin (0.014 g, 0.065 mmol) and HATU (0.027 g, 0.071 mmol) in 0.5 mL of DMF with constant stirring at room temperature until a clear solution resulted. Subsequently, 2-(3-Amino-phenyl)-indole-1-carboxylic acid tert-butyl ester (0.013 g, 0.065 mmol) was added and allowed to react overnight when a solid precipitated out of solution. The resulting precipitate was filtered, dried under suction, and finally dried overnight in vacuo to give 0.012 g of product in 47% yield: LCMS (ESI) m/z 408 ($MH^+$).

Example 190

Synthesis of 7-Methoxy-benzofuran-2-carboxylic acid (3-imidazo[1,2-a]pyridin-2-yl-phenyl)-amide (179)

DIEA (49.9 µL, 0.29 mmol) was added to 7-Methoxy-benzofuran-2-carboxylic acid (50 mg, 0.26 mmol) and HATU (108.8 mg, 0.29 mmol) in 1 mL of DMF with constant stirring at room temperature until a clear solution resulted. Subsequently, 3-Imidazo[1,2-a]pyridin-2-yl-phenylamine (54.4 mg, 0.26 mmol) was added and allowed to react overnight when a solid precipitated out of solution. The resulting precipitate was filtered, dried under suction, and finally dried overnight in vacuo to give the final product: LCMS (ESI) m/z 384 ($MH^+$).

Example 191

Synthesis of 6-Chloro-2H-chromene-3-carboxylic acid (3-imidazo[1,2-a]pyridin-2-yl-phenyl)-amide (180)

DIEA (45.5 µL, 0.26 mmol) was added to 6-chloro-2H-chromene-3-carboxylic acid (50.0 mg, 0.24 mmol) and HATU (99.3 mg, 0.26 mmol) in 2 mL of DMF with constant stirring at room temperature until a clear solution resulted. Subsequently, 3-Imidazo[1,2-a]pyridin-2-yl-phenylamine (49.7 mg, 0.24 mmol) was added and allowed to react overnight when a solid precipitated out of solution. The resulting precipitate was filtered, dried under suction, and finally dried overnight in vacuo to give 66.6 mg of product in 69% yield: LCMS (ESI) m/z 401 (MH+).

Example 192

Synthesis of 2-Oxo-1,2-dihydro-quinoline-3-carboxylic acid (3-imidazo[1,2-a]pyridin-2-yl-phenyl)-amide (181)

2-Aminobenzaldehyde (84.1 mg, 0.69 mmol) and Meldrum's acid (100 mg, 0.69 mmol) were combined in $H_2O$ (1 mL). The solution was stirred at 75° C. for 2 h. After cooling to room temperature, the precipitate was filtered and dried at suction to give 86.2 mg of 1,2-dihydro-quinoline-3-carboxylic acid with a yield of 66%.

DIEA (50.7 μL, 0.29 mmol) was added to 2-Oxo-1,2-dihydro-quinoline-3-carboxylic acid (50.0 mg, 0.26 mmol) and HATU (110.6 mg, 0.29 mmol) in 1 mL of DMF with constant stirring at room temperature until a clear solution resulted. Subsequently, 3-Imidazo[1,2-a]pyridin-2-yl-phenylamine (55.3 mg, 0.26 mmol) was added and allowed to react overnight when a solid precipitated out of solution. The resulting precipitate was filtered, dried under suction, and finally dried overnight in vacuo to give the final product: LCMS (ESI) m/z 381 (MH+).

Example 193

Synthesis of 8-Methoxy-2H-chromene-3-carboxylic acid (3-imidazo[1,2-a]pyridin-2-yl-phenyl)-amide (182)

DIEA (46.5 μL, 0.27 mmol) was added to 8-Methoxy-2H-chromene-3-carboxylic acid (50.0 mg, 0.24 mmol) and HATU (101.4 mg, 0.27 mmol) in 2 mL of DMF with constant stirring at room temperature until a clear solution resulted. Subsequently, 3-Imidazo[1,2-a]pyridin-2-yl-phenylamine (50.7 mg, 0.24 mmol) was added and allowed to react overnight when a solid precipitated out of solution. The resulting precipitate was filtered, dried under suction, and finally dried overnight in vacuo to give 81.0 mg of product in 85% yield: LCMS (ESI) m/z 398 (MH+).

Example 194

Synthesis of 8-Methoxy-2-oxo-2H-chromene-3-carboxylic acid [4-(1H-benzoimidazol-2-yl)-phenyl]-amide (183)

DIEA (43.5 μL, 0.25 mmol) was added to 8-methoxy-3-carboxy-coumarin (50.0 mg, 0.23 mmol) and HATU (95.0 mg, 0.25 mmol) in 1 mL of DMF with constant stirring at room temperature until a clear solution resulted. Subsequently, 4-(1H-benzoimidazol-2-yl)-phenylamine (47.5 mg, 0.23 mmol) was added and allowed to react overnight when a solid precipitated out of solution. The resulting precipitate was filtered, dried under suction, and finally dried overnight in vacuo to give 71.0 mg of product in 75% yield: LCMS (ESI) m/z 412 (MH+).

Example 195

Utility and Testing

The executioner procaspase-3, -6 and -7 activation assay protocol involves incubating the target protein at the physiologically-relevant concentration of 100 nM with activating compounds (ranging from 100 nM to 100 uM) in a total volume of 50 μL consisting of a reaction buffer of 50 mM HEPES, pH 7.4, 50 mM KCl, 1 mM DTT and 0.01% Triton-X100 (to reduce false positive hits due to compound aggregation). The procaspase/small molecule incubations are then agitated at 37° C. and assayed at various time points by addition of the fluorogenic peptide substrate 7-Amino-4-trifluoromethylcoumarin-DEVD (Ac-DEVD-AFC) (procaspases-3, -7) or Ac-VEID-AFC (procaspase-6) to a final concentration of 25 μM and analyzed by a kinetic 30 minute assay (excitation 365 nm and emission 495 nm). The final concentration of DMSO in each well is 3% and has no effect on enzyme stability or activity. The maximum activity of "activated" procaspase is established by proteolytically-cleaving the procaspase with granzyme-b and thus "turn on" the procaspase (granzyme-b is added at a concentration 1:1000 of procaspase-3 and thus does not contribute to observable activity). All components of the assay including protein, substrate and inhibitor are stored as frozen aliquots and thawed immediately prior to the assay.

Tables 1 and 2 show examples of certain compounds of the present invention and the effect on activation of procaspase 3.

TABLE 1

Procaspase Activation

| ID | $R^2$ | $R^{2a}$ | $R^{2b}$ | 3 | 6 | 7 |
|---|---|---|---|---|---|---|
| 1541 | —OMe | —H | —H | +++ | +++ | — |
| 1541A | —OH | —H | —H | +++ | — | — |
| 1 | —H | —H | —Br | + | + | ND |
| 1541B | —OCF₃ | —H | —H | — | — | ND |
| 1541C | —H | —OMe | —H | — | — | ND |
| 2 | —F | —H | —H | +++ | +++ | ND |
| 3 | —OH | —OH | —H | + | — | ND |
| 4 | —Br | —H | —H | — | — | ND |
| 5 | —OEt | —H | —H | — | — | ND |
| 6 | —H | —H | —OMe | — | — | ND |
| 7 | —H | —OH | —OH | — | — | ND |
| 8 | —OMe | —OMe | —H | — | ND | ND |
| 9 | —H | —H | —OCF₃ | — | — | ND |
| 10 | —H | —H | —I | — | — | ND |
| 11 | —H | —H | —OH | — | — | ND |
| 12 | —H | —H | —OMe | — | — | ND |
| 13 | —H | —H | —H | — | ND | ND |
| 14 | morpholine-N | —H | —OMe | — | — | — |
| 1541D | morpholine-CH₂ | —H | —OMe | — | — | ND |

TABLE 2
Procaspase Activation
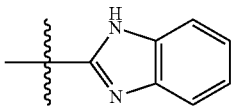 [SMILES: *c1nc2ccccc2[nH]1]
| ID | R² | R³ | 3 | 6 | 7 |
|---|---|---|---|---|---|
| 1541H | —OMe | —H | — | — | ND |
| 15 | —OH | 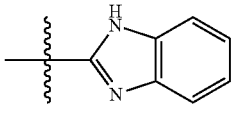 [SMILES: *c1nc2ccccc2[nH]1] | — | — | — |
| 1541F | —OMe | 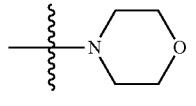 | — | — | ND |
| 16 | —OH | 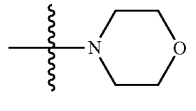 | — | — | — |
| 1541I | —OMe | 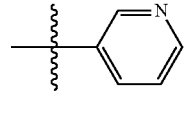 | — | — | ND |
| 17 | —OH | 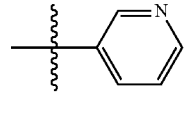 | — | — | — |
| 18 | —OMe | 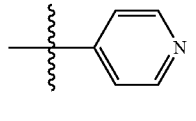 | — | — | — |
| 19 | —OH | 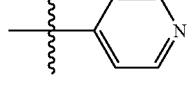 | +++ | +++ | + |
| 20 | —OMe | 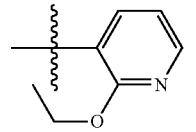 | — | — | ND |
| 41 | —OH | 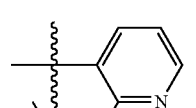 | ++ | + | — |
| 42 | —OMe | 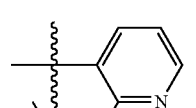 | — | — | — |

TABLE 2-continued
| | | | | | |
|---|---|---|---|---|---|
| 43 | —OCF₃ | 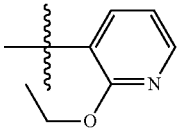 [SMILES: *c1cccnc1OCC] | — | — | — |
| 44 | —OH | 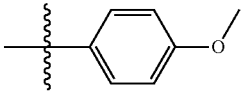 [SMILES: *c1ccc(OC)cc1] | — | — | +++ |
| 45 | —OMe | 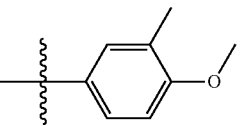 | — | — | — |
| 46 | —OCF₃ | 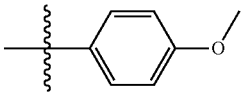 [SMILES: *c1ccc(OC)cc1] | — | — | — |
| 47 | —OH | 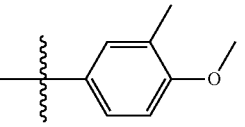 [SMILES: *c1ccc(OC)c(C)c1] | — | — | — |
| 48 | —OMe | 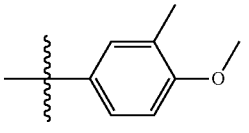 | — | — | — |
| 49 | —OCF₃ | 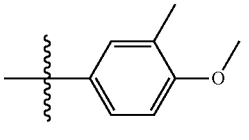 | — | — | — |
| 50 | —OH | 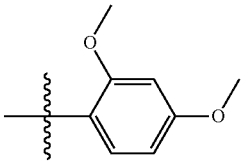 | — | — | — |
| 51 | —OMe | 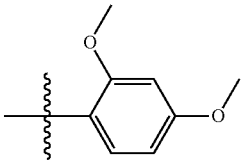 | — | — | — |
| 52 | —OCF₃ | 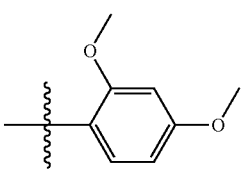 [SMILES: *c1ccc(OC)cc1OC] | — | — | — |
| 53 | —OH | 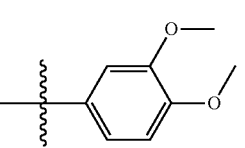 [SMILES: *c1ccc(OC)c(OC)c1] | — | — | +++ |

TABLE 2-continued
| 54 | —OMe | 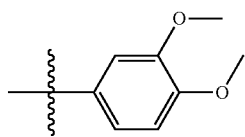 | — | — | — |
| 55 | —OCF₃ | 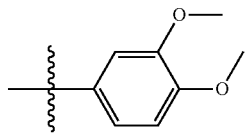 [SMILES: *c1ccc(OC)c(OC)c1] | — | — | — |
| 56 | —OH | 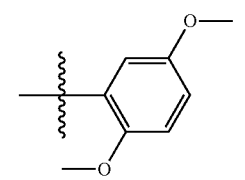 [SMILES: *c1cc(OC)ccc1OC] | — | — | — |
| 57 | —OMe | 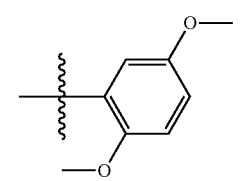 | — | — | — |
| 58 | —OCF₃ | 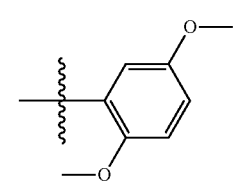 | — | — | — |
| 59 | —OH | 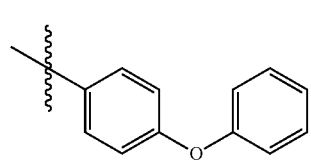 [SMILES: *c1ccc(Oc2ccccc2)cc1] | — | — | — |
| 60 | —OMe | 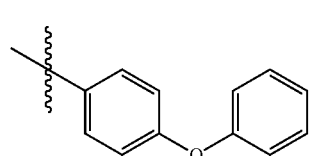 | — | — | — |
| 61 | —OCF₃ | 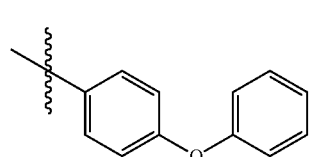 | — | — | — |
| 62 | —OH | 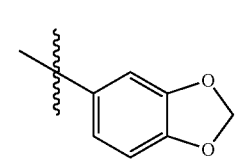 [SMILES: *c1ccc2c(c1)OCO2] | — | — | ++ |
| 63 | —OMe | 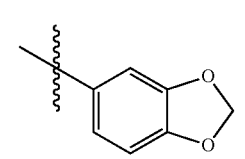 [SMILES: *c1ccc2c(c1)OCO2] | — | — | — |

TABLE 2-continued

| | | | | | |
|---|---|---|---|---|---|
| 64 | —OCF$_3$ | benzo[1,3]dioxole substituent | — | — | — |
| 65 | —OH | 3-methyl-4-ethoxyphenyl | — | — | — |
| 66 | —OMe | 3-methyl-4-ethoxyphenyl | — | — | — |
| 67 | —OCF$_3$ | 3-methyl-4-ethoxyphenyl | — | — | — |
| 68 | —OH | 4-ethoxyphenyl | — | — | — |
| 69 | —OMe | 4-ethoxyphenyl | — | — | — |
| 70 | —OCF$_3$ | 4-ethoxyphenyl | — | — | — |
| 71 | —OH | 2-(trifluoromethoxy)phenyl | — | — | — |
| 72 | —OMe | 2-(trifluoromethoxy)phenyl | — | — | — |
| 73 | —OCF$_3$ | 2-(trifluoromethoxy)phenyl | — | — | — |
| 74 | —OH | 2,3-dihydrobenzofuran-5-yl | — | — | ++ |
| 75 | —OMe | 2,3-dihydrobenzofuran-5-yl | — | — | — |

TABLE 2-continued

| | | | | | |
|---|---|---|---|---|---|
| 76 | —OCF₃ | [2,3-dihydrobenzofuran-5-yl] | — | — | — |
| 77 | —OH | [7-methoxynaphthalen-2-yl] | — | — | +++ |
| 78 | —OMe | [7-methoxynaphthalen-2-yl] | — | — | — |
| 79 | —OCF₃ | [7-methoxynaphthalen-2-yl] | — | — | — |
| 80 | —OH | [naphthalen-2-yl] | — | — | — |
| 81 | —OMe | [naphthalen-2-yl] | — | — | — |
| 82 | —OCF₃ | [naphthalen-2-yl] | — | — | — |
| 83 | —OH | [quinolin-3-yl] | — | — | — |
| 84 | —OMe | [quinolin-3-yl] | — | — | — |
| 85 | —OCF₃ | [quinolin-3-yl] | — | — | — |
| 86 | —OH | [2,3-dihydrobenzo[b][1,4]dioxin-6-yl] | — | — | — |

TABLE 2-continued
| | | | | | |
|---|---|---|---|---|---|
| 87 | —OMe | 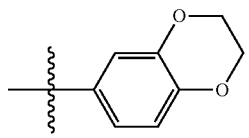 [SMILES: *c1ccc2c(c1)OCCO2] | — | — | — |
| 88 | —OCF₃ | 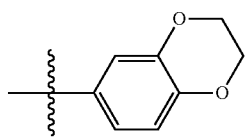 [SMILES: *c1ccc2c(c1)OCCO2] | — | — | — |
| 89 | —OH | 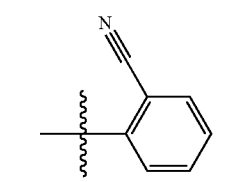 [SMILES: *c1ccccc1C#N] | — | — | — |
| 90 | —OMe | 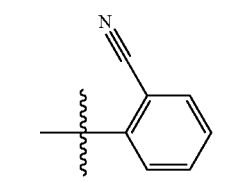 | — | — | — |
| 91 | —OCF₃ | 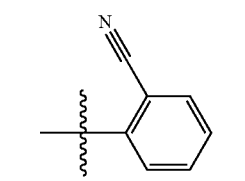 [SMILES: *c1ccccc1C#N] | — | — | — |
| 92 | —OH | 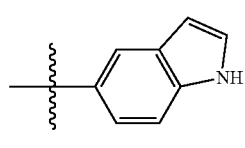 | — | — | — |
| 93 | —OMe | 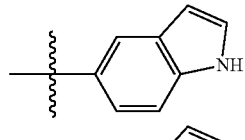 | — | — | — |
| 94 | —OCF₃ | 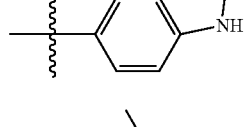 | — | — | — |
| 95 | —OH | 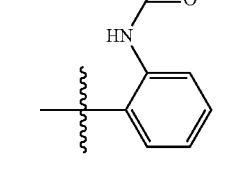 | — | — | — |
| 96 | —OMe | 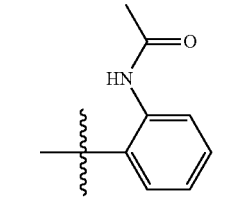 [SMILES: *c1ccccc1NC(C)=O] | — | — | — |

TABLE 2-continued

| | | | | | |
|---|---|---|---|---|---|
| 97 | —OCF₃ | *acetamido-phenyl group* | — | — | — |
| 98 | —OH | *morpholinosulfonyl-phenyl group* | ++ | — | ++ |
| 99 | —OMe | *morpholinosulfonyl-phenyl group* | — | — | — |
| 100 | —OCF₃ | *morpholinosulfonyl-phenyl group* | — | — | — |
| 127 | —OH | *2,4-dimethoxypyrimidin-5-yl group* | — | — | — |
| 128 | —OMe | *2,4-dimethoxypyrimidin-5-yl group* | — | — | — |
| 129 | —OH | *6-methoxypyridin-3-yl group* | — | — | — |
| 130 | —OMe | *6-methoxypyridin-3-yl group* | — | — | — |
| 131 | —OH | *5-methoxypyridin-3-yl group* | — | — | — |
| 132 | —OMe | *5-methoxypyridin-3-yl group* | — | — | — |

TABLE 2-continued

| | | | | | |
|---|---|---|---|---|---|
| 133 | —OH | 5-(2-methoxypyrimidinyl) | — | — | — |
| 134 | —OMe | 5-(2-methoxypyrimidinyl) | — | — | — |
| 135 | —OH | 5-pyrimidinyl | — | — | — |
| 136 | —OMe | 5-pyrimidinyl | + | + | — |
| 137 | —OH | 5-(2-dimethylaminopyridinyl) | — | — | — |
| 138 | —OMe | 5-(2-dimethylaminopyridinyl) | — | — | — |
| 139 | —OH | 5-(2-hydroxypyridinyl) | — | — | — |
| 140 | —OMe | 5-(2-hydroxypyridinyl) | — | — | — |
| 141 | —OH | 3-(2-methoxypyridinyl) | — | — | ++ |
| 142 | —OMe | 3-(2-methoxypyridinyl) | — | — | — |
| 143 | —OH | 4-(2-fluoro-4-cyanophenyl) | — | — | — |
| 144 | —OMe | 4-(2-fluoro-4-cyanophenyl) | — | — | — |

TABLE 2-continued

| | | | | | |
|---|---|---|---|---|---|
| 145 | —OH | 2-fluoro-5-substituted benzonitrile | — | — | — |
| 146 | —OMe | 2-fluoro-5-substituted benzonitrile | — | — | — |
| 147 | —OH | 3-substituted benzonitrile | — | — | — |
| 148 | —OMe | 3-substituted benzonitrile | — | — | — |
| 149 | —OH | 1H-pyrazol-4-yl | — | — | — |
| 150 | —OMe | 1H-pyrazol-4-yl | — | — | — |
| 151 | —OH | 1-methyl-1H-pyrazol-5-yl | ++ | — | ++ |
| 152 | —OMe | 1-methyl-1H-pyrazol-5-yl | — | — | — |
| 153 | —OH | 3,5-dimethylisoxazol-4-yl | ++ | — | ++ |
| 154 | —OMe | 3,5-dimethylisoxazol-4-yl | — | — | — |

TABLE 2-continued

| # | R | Structure | | | |
|---|---|---|---|---|---|
| 155 | —OH | pyrazole | — | — | — |
| 156 | —OMe | pyrazole | — | — | — |
| 157 | —OH | benzimidazol-2-one | — | — | — |
| 158 | —OMe | benzimidazol-2-one | — | — | — |
| 159 | —OH | benzofurazan | — | — | — |
| 160 | —OMe | benzofurazan | — | — | — |
| 161 | —OH | chromen-4-one | +++ | — | — |
| 162 | —OMe | chromen-4-one | — | +++ | — |
| 163 | —OH | 1-methylindazole | — | — | — |
| 164 | —OMe | 1-methylindazole | — | — | — |
| 165 | —OH | 1H-indole | — | — | — |

TABLE 2-continued
| | | | | | |
|---|---|---|---|---|---|
| 166 | —OMe | 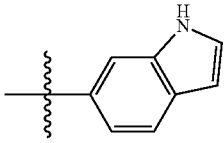 [SMILES: *c1ccc2cc[nH]c2c1] | — | — | — |
| 167 | —OH | 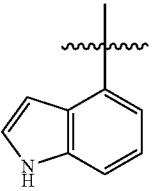 [SMILES: *c1cccc2[nH]ccc12] | — | — | — |
| 168 | —OMe | 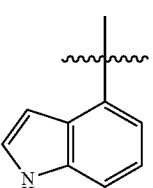 | — | — | — |
| 169 | —OH | 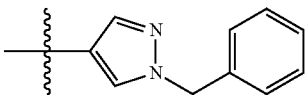 [SMILES: *c1cnn(Cc2ccccc2)c1] | — | — | — |
| 170 | —OMe | 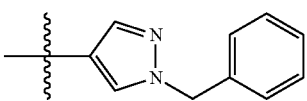 [SMILES: *c1cnn(Cc2ccccc2)c1] | — | — | — |
| 171 | —OH | 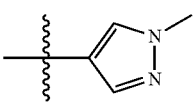 [SMILES: *c1cnn(C)c1] | — | — | — |
| 172 | —OMe | 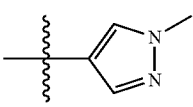 [SMILES: *c1cnn(C)c1] | — | — | — |
| 173 | —OH | 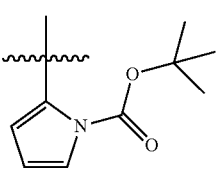 [SMILES: *c1cccn1C(=O)OC(C)(C)C] | — | — | — |
| 174 | —OMe | 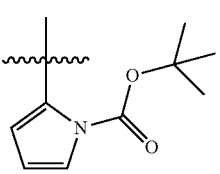 [SMILES: *c1cccn1C(=O)OC(C)(C)C] | — | — | — |
| 175 | —OH | 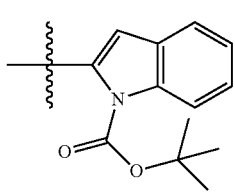 [SMILES: *c1cc2ccccc2n1C(=O)OC(C)(C)C] | — | — | — |

TABLE 2-continued
| 176 | —OMe | 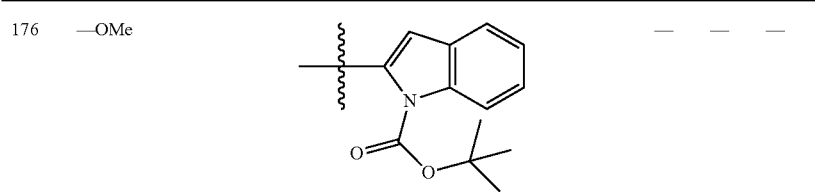 | — | — | — |
| 177 | —OH | 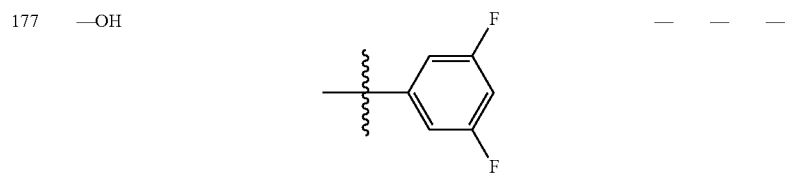 | — | — | — |
| 178 | —OMe | 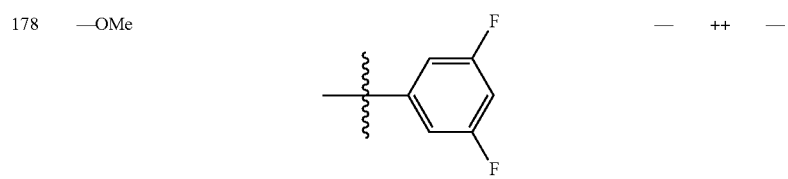 | — | ++ | — |
| ID | Compound | 3 | 6 | 7 |
|---|---|---|---|---|
| 179 | 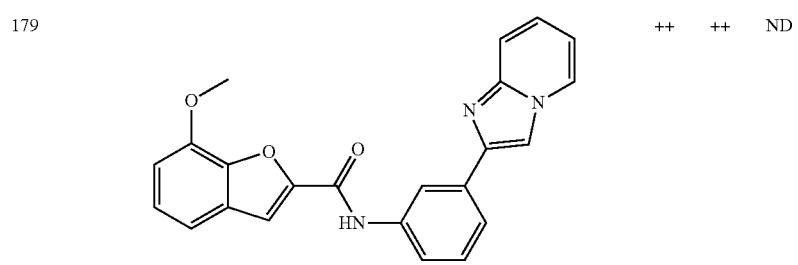 | ++ | ++ | ND |
| 180 | 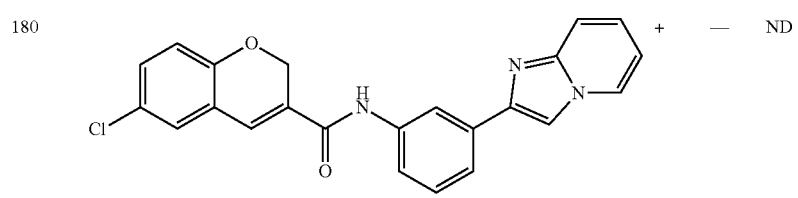 | + | — | ND |
| 181 | 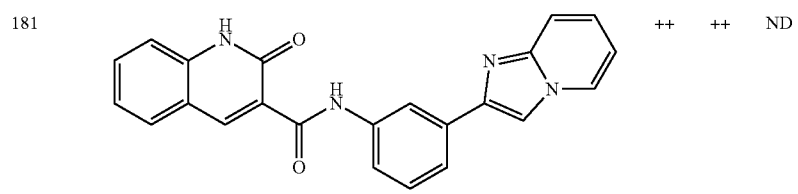 | ++ | ++ | ND |
| 182 | 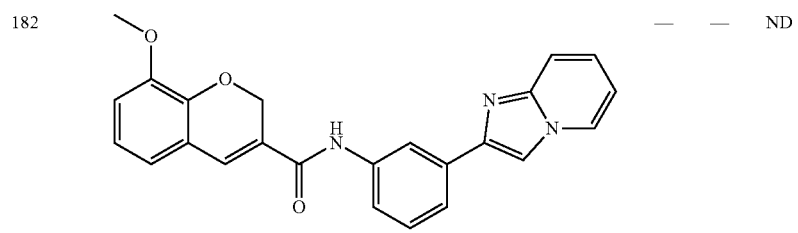 | — | — | ND |

TABLE 2-continued

| 183 | [8-methoxy-2-oxo-2H-chromene-3-carboxylic acid (4-(1H-benzimidazol-2-yl)phenyl)amide structure] | +++ | ND | ND |

Tables 1 and 2. Procaspase activation as a result of incubation with compound for 5 h at 37° C. (+++ EC$_{50}$~0.5-10 μM; ++ EC$_{50}$~10-50 μM; + EC$_{50}$~50-200 μM; -no activation observed; ND not determined).

Procaspase-7 expression and purification: Full-length procaspase-7 is overexpressed from *E. coli* cells for 30 minutes to prevent autocatalysis. Soluble fractions are purified to homogeneity by Ni-NTA affinity, anion-exchange and gel-filtration chromatography with an overall protein yield of approximately 0.2 mg/L of culture and >95% purity as determined by SDS-PAGE (FIGS. 1A and 1B). Procaspase-7 is purified as a monomer and has no observable activity. Overnight incubation at 37° C. results in approximately 50% autocatalysis to active caspase-7.

Full-length procaspase-7 is expressed with a C-terminal His$_6$-affinity tag from *E. coli* BL21(DE3)RP cells (Stratagene) in a pET-21b vector (Novagen). Cells are grown in 1.5 L of 2×YT media supplemented with 50 μg/mL ampicillin and 25 μg/mL chloramphenicol at 37° C. to an OD$_{600nm}$ of 0.8-1.0. Overexpression of procaspase-7 is induced with 0.2 mM IPTG at 30° C. and cells are immediately harvested and frozen at −70° C. after 30 minutes to limit autocatalysis. Cells are thawed, resuspended in 100 mM Tris, pH 8.0, 100 mM NaCl and subjected to lysis by microfluidization (Microfluidics, Inc., Newton, Mass.). Subsequent centrifugation at 25,000 g for 40 minutes removes cellular debris and soluble fractions are purified to homogeneity by Ni-NTA affinity (HisTrap HP columns, GE Amersham) followed with anion-exchange (HiTrap Q HP, GE Amersham) and gel-filtration chromatography (Superdex 200 16/60, GE Amersham). Pure procaspase-7 is immediately frozen at −70° C. The yield of procaspase-7 is approximately 0.2 mg/L of culture.

Active caspase-7 HTS screen: The preliminary screen of 12,000 compounds of formula I for inhibitors of the active caspase-7 conformer was performed by the Small Molecule Discovery Center (SMDC). The Z' was determined to be 0.9 in a 384-well plate with a reaction volume of 50 μL in a buffer consisting of 100 mM HEPES, pH 7.0, 5 mM CaCl$_2$, 0.5 mM (3-ME and 0.1% CHAPS (FIG. 2). The concentrations of caspase-7 and the fluorogenic peptide substrate rhodamine 110, bis-(N-CBZ-DEVD) (Z-DEVD-R110) were 50 nM and 10 μM, respectively and were optimized based on the criteria of linear activity and maximum signal after 30 minutes. To obtain the average minimum activity, 10 μM of the covalent active site inhibitor DEVD-CHO was added and incubated for 10 minutes at room temperature prior to reaction initiation by substrate addition. After addition of the Z-DEVD-R110 substrate, the reaction was quenched with 40 mM HCl after 30 minutes and the endpoint fluorescence was measured on an Analyst HT Assay Detection System (LJL Biosystem, Sunnyvale, Calif.). The final concentration of DMSO in each well was 3% and had no effect on enzyme stability or activity. All components of the assay excluding protein are commercially available with protein, substrate and inhibitor stocks stored as frozen aliquots and thawed immediately prior to the assay. Z-DEVD-R110 is sensitive to light and caspase-7 inhibitor DEVD-CHO degrades after several hours; therefore, care must be taken when handling these solutions.

Screening protocol development and optimization: Assays will be performed in a 50 μL volume, in 384-well plates, consisting of a reaction buffer of 100 mM HEPES, pH 7.0, 5 mM CaCl$_2$, 0.5 mM β-ME and 0.1% CHAPS (to reduce false positive hits due to compound aggregation) initiated by addition of substrate Z-DEVD-R110 to approximately 100 nM procaspase-7. The reaction is quenched with 40 mM HCl and endpoint assays is performed at various time points at room temperature and read on an Analyst HT AD plate reader which can accommodate both 96-well and 384-well formats. For any potential activators of procaspase-7, IC$_{50}$ measurements is determined using GraphPad Prism software (GraphPad, Inc., San Diego, Calif.).

In order to obtain Z' and optimize assay conditions, procaspase-7 is proteolytically cleaved and the protein is "turned on" by addition of a small amount of active caspase-7. The maximal activity of procaspase-7 then is extrapolated from the active caspase-7 contribution. Once completed, optimization of protein and substrate concentration, as well as time and temperature of HTS compound incubation will be assessed. Similar disparateness is obtained between inactive and activated species for procaspase-7 as observed for Z' determination of active caspase-7 as the substrate Z-DEVD-R110 signal is extremely robust (FIG. 2).

Figure 3:
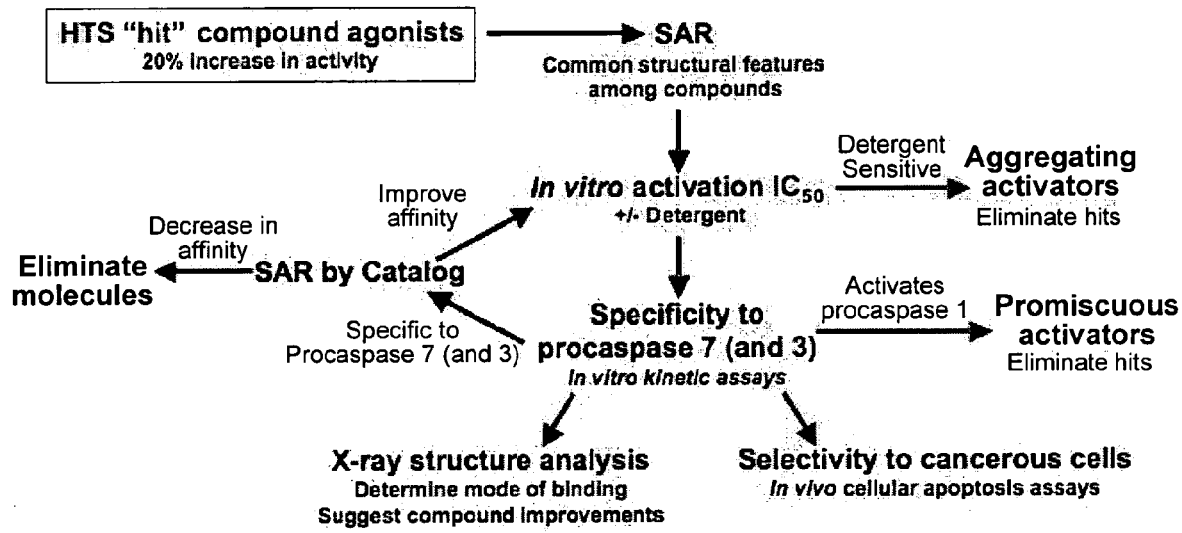
FIG. 3. Triage pipeline for HTS agonist hits against procaspase-7. Hits that pass evaluations and eliminated from further studies are labeled blue and red, respectively.

Triage and analysis of potential activators: Any compounds from the high throughput screens with an increased activity of 20% over the inherent activity of procaspase-7 are considered a "hit" and is analyzed for specificity and mode of binding. Structure activity relationships, as well as common structural features are established among agonistic compounds following HTS screening (FIG. 3). In vitro activity assays will determine IC$_{50}$'s in both the presence and absence of detergent to remove hits with potential for aggregation (McGovern, et al., A common mechanism underlying promiscuous inhibitors from virtual and high-throughput screening. *J. Med. Chem.* 45, 1712-1722 (2002); and Seidler, et al., Identification and prediction of promiscuous aggregating inhibitors among known drugs. *J. Med. Chem.* 46, 4477-4486 (2003)). The specificity of compounds to procaspase-7 is analyzed for activity promotion of procaspase-1 with any promiscuous activators eliminated as artifacts from further studies. Commercially available molecular derivatives of specific procaspase-7 activator hits are purchased and screened for increased affinity as a quick initial optimization procedure (SAR by catalog).

Caspases-3 and -7 perform similar roles in apoptosis suggesting a pan inhibitor would be useful. These enzymes are highly conserved in both sequence and structure. Therefore, agonist identification, optimization and selectivity will be performed on procaspase-3 in parallel with procaspase-7 (FIG. 3). All agonistic procaspase-7 HTS hits will be analyzed for any preferential selectivity towards procaspase-3 as compounds that target the conserved allosteric homodimeric pocket are predicted to have similar activating effects on both proteins; however, compounds that interact with other less conserved surface regions may have preferential affinity and activation towards a particular caspase. Compounds with preferred specificity towards either procaspases-3 or -7 will be subjected to analog library synthesis to resolve and optimize affinity.

Structures of procaspase-7 in complex with promising molecules are determined by X-ray crystallography. Co-crystallization and/or ligand soaking experiments on any procaspase crystals will provide procaspase-agonist complexes in order to identify location and mode of binding, as well as provide suggestions for compound optimization. For co-crystallization, protein (10-12 mg/ml) and 0.5-5 mM solutions of each compound are mixed and stored overnight at 4° C. prior to primary crystallization screens using standard microvapor diffusion methods under conditions that will include those previously determined for native and complex structures (Chai, J., et al. Crystal structure of a procaspase-7 zymogen: Mechanisms of activation and substrate binding. *Cell* 107, 399-407 (2001); Hardy, et al., Searching for new allosteric sites in enzymes. *Curr. Opin. Struct. Biol.* 14, 706-715 (2004); Riedl, S. J., et al. Structural basis for the activation of human procaspase-7. *Proc. Natl. Acad. Sci.* 98, 14790-14795 (2001). Riedl, S. J., et al. Structural basis for the inhibition of caspase-3 by XIAP. *Cell* 104, 791-800 (2001)). If co-crystallization does not yield crystal structures with interpretable compound density, native crystals can be soaked in the presence of a high concentration of agonists (5-10 mM) for 5-8 hours at room temperature. After the primary crystallization condition has been ascertained, effects of pH, temperature, salt concentration, precipitants and organic solvents will be tested to optimize crystal size, morphology and, in particular, crystal diffraction. In order to observe the structural transitions induced by agonist binding and eliminate the potential of self-proteolysis during crystallization, procaspase-7 will be inactivated by alanine substitution of the active site cysteine.

Procaspases-3 and -7 expression and purification: Procaspase-7 expression was improved by inclusion of the plasmid into various expression vectors encompassing different affinity tags and protein terminal locations including pGEX-6P1 (N-terminal GST fusion, GE Amersham) and pET19b (N-terminal $His_6$ affinity tag, Novagen), as well as various competent *E. coli* expression cell lines. Similarly, induction with IPTG was optimized for concentration, temperature and duration of overexpression. Despite yield optimization of our protein, analysis of procaspase-7 revealed a lack of ability for self-activation as previously described (Van de Craen, et al., The proteolytic procaspase activation network: an in vitro analysis. *Cell Death Differ.* 6, 1117-1124 (1999)). Therefore, focus was turned to procaspase-3 as caspases-3 and -7 perform similar roles in apoptosis, are highly conserved in both sequence and structure, and, moreover, procaspase-3 can self-activate (see, Van de Craen, et al.).

Figure 4:
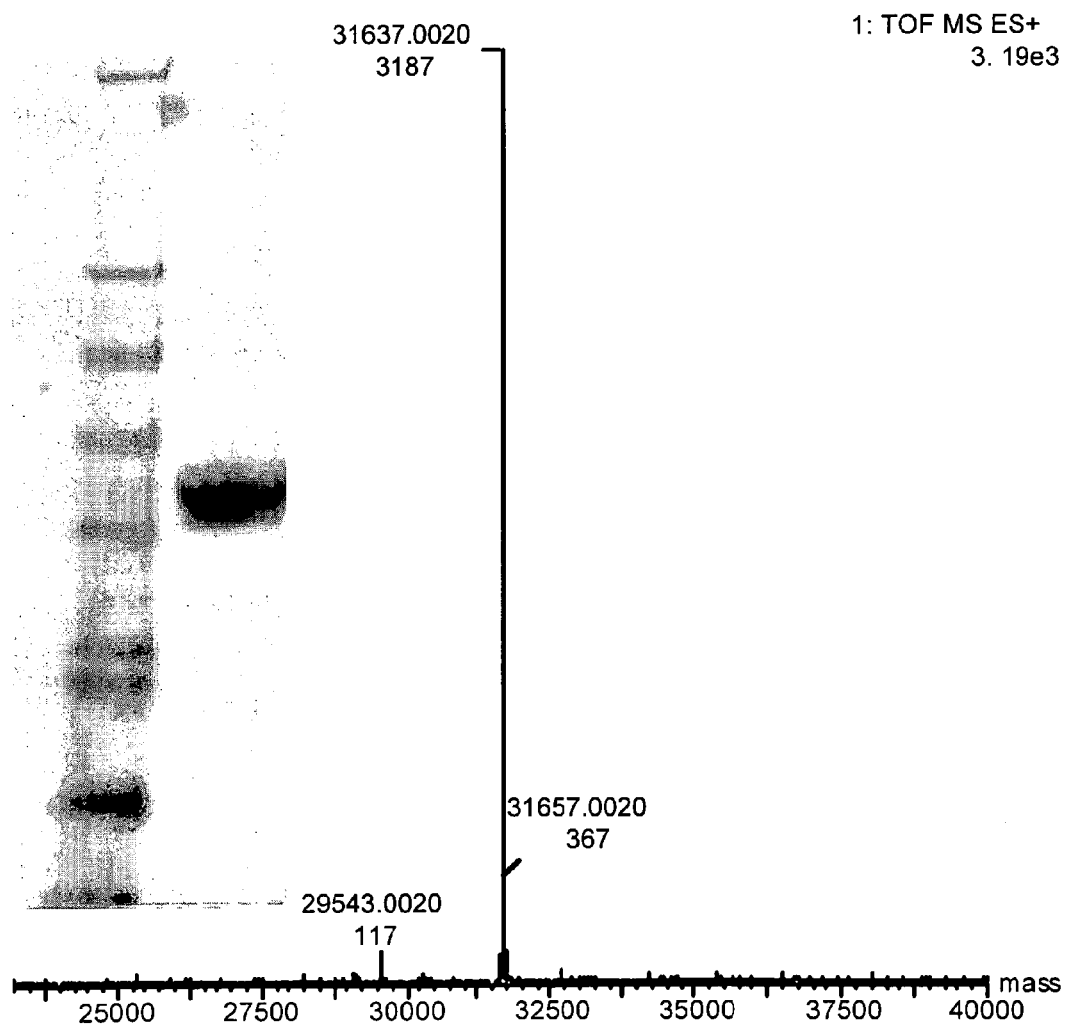
FIG. 4. Example of procaspase-3 purity used for the HTS assays. Shown are a 4-12% SDS page gel and an electrospray ionization mass spectrum.

Procaspase-3 was overexpressed with a C-terminal $His_6$-affinity tag from *E. coli* BL21(DE3)RP cells (Stratagene) in a pET-23b vector (Novagen). Cells were grown in 2×YT media supplemented with 200 μg/mL ampicillin and 50 μg/mL chloramphenicol at 37° C. to an $OD_{600nm}$ of 0.8-1.0. Overexpression of procaspase-3 was induced with 0.2 mM IPTG at 30° C. and were immediately harvested and frozen at −70° C. after 40 minutes to limit autocatalysis. Cells were thawed, resuspended in 100 mM Tris, pH 8.0, 100 mM NaCl and subjected to lysis by microfluidization (Microfluidics, Inc., Newton, Mass.). Subsequent centrifugation at 25,000 g for 40 minutes removed cellular debris and soluble fractions were purified to homogeneity by Ni-NTA affinity (HisTrap HP columns, GE Amersham) followed with anion-exchange (HiTrap Q HP, GE Amersham) and gel-filtration chromatography (Superdex 200 16/60, GE Amersham). Pure procaspase-3 was immediately frozen at −70° C. The final purified procaspase-3 was approximately 95-98% pure according to both SDS-page gels and electrospray ionization mass spectrometry (FIG. 4). Our yield was approximately 0.3 mg/L of culture per purification and multiple rounds of expression and purification were required to amass the amount of protein needed for the HTS assay.

Screening protocol development and optimization: In order to obtain Z' and optimize assay conditions, procaspase-3 with granzyme-b was proteolytically-cleaved and thus the procaspase was "turned on" to determine maximal activity (granzyme-b was added at a concentration 1:1000 of procaspase-3 and thus did not contribute to observable activity). Once completed, optimization of protein and substrate concentration, as well as time and temperature of HTS compound incubation was assessed. We were pleased as we obtained similar disparateness of activity between inactive and activated species of procaspase-3 in comparison to the average Z' of 0.90 obtained during the inhibitor HTS screen against active caspase-7.

The high throughput procaspase-3 activation assay protocol was developed and based on the 384-well plate active caspase-7 HTS inhibitor screen. Procaspase-3 was incubated at a physiologically-relevant concentration of 100 nM (Pop, C., et al. Removal of the pro-domain does not affect the conformation of the procaspase-3 dimer. *Biochemistry* 40, 14224-14235 (2001)) with 30 μM HTS compounds in a total volume of 50 μL consisting of a reaction buffer of 25 mM HEPES, pH 7.4, 50 mM KCl, 1 mM DTT and 0.1% CHAPS (to reduce false positive hits due to compound aggregation). The procaspase-3/small molecule incubations were then agitated for 3 hours at 37° C. A fluorogenic peptide substrate rhodamine 110, bis-(N-CBZ-DEVD) (Z-DEVD-R110) was subsequently added to a final concentration of 10 μM by a MultiMex bulk liquid dispenser (Beckman) and incubated for an additional 30 minutes at room temperature. The reaction was quenched with 40 mM HCl and the endpoint fluorescence was measured on an Analyst HT Assay Detection System (LJL Biosystem, Sunnyvale, Calif.). The final concentration of DMSO in each well was 3% and had no effect on enzyme stability or activity. All components of the assay including protein, substrate and inhibitor were stored as frozen aliquots and thawed immediately prior to the assay.

Figure 5:
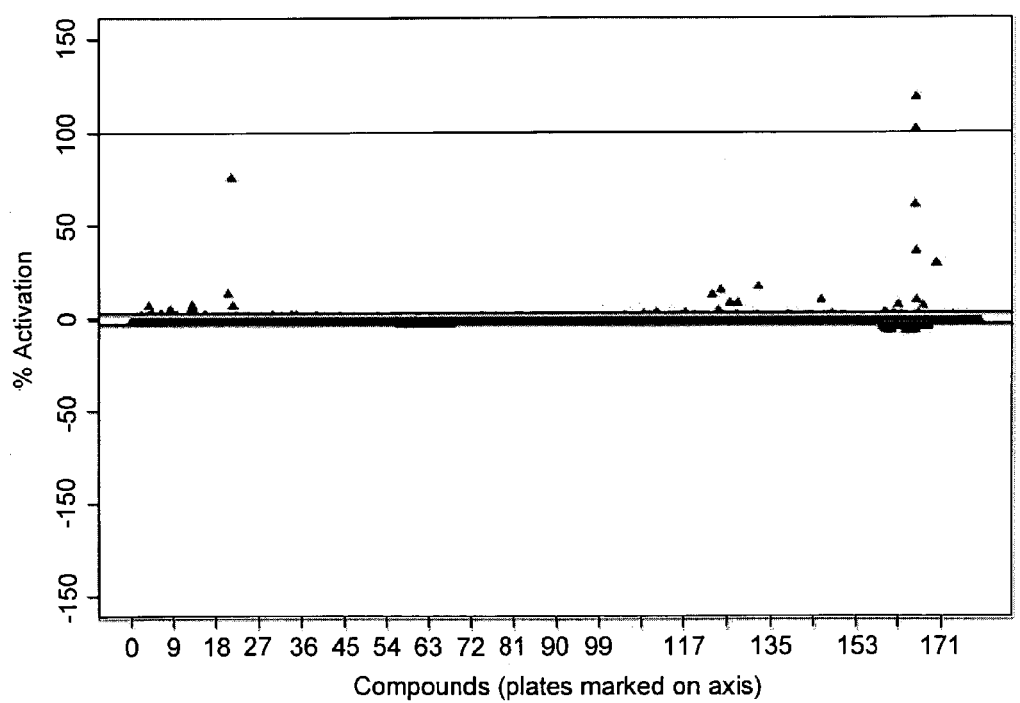
FIG. 5. Schematic of all of the compounds screened for procaspase-3 activation. The Z' ranged between 0.85 and 0.95 for all assays.

HTS Screen Results: A total of 62,000 compounds of formula I, consisting of 3 small molecule libraries, were screened for their ability to activate procaspase-3 after a 3-hour incubation at 37° C. The small molecule HTS libraries screened included approximately 12,000 compounds from the ChemDiv Diversity set, 10,000 compounds from the ChemDiv Kinase library and 40,000 small molecules from a custom library housed at UCSF in the SMDC. Approximately 4,000 compounds/day were assayed with a Z' ranging from 0.85 to 0.95 over the course of two months. Any compounds from the high throughput screens with an increased activity of 20% or more over the inherent activity of procaspase-3 will be considered a potential "hit" and will be re-synthesized and analyzed for specificity and mode of binding. Several compounds have shown activation of procaspase-3 according to the benchmarks as evidenced in FIG. 5.

Although the foregoing invention has been described in some detail by way of illustration and example for purposes of clarity of understanding, one with skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound of formula:

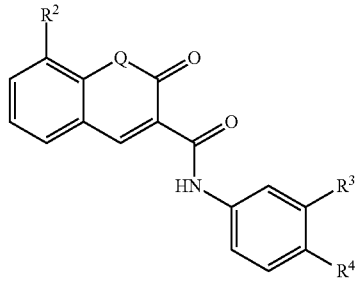

or a pharmaceutically acceptable salt thereof;
wherein
Q is —O—;
$R^2$ is independently selected from the group consisting of aryl-$C_{1-6}$alkyl, —$C_{1-6}$alkyl, —$OC_{1-6}$alkyl, —OH, halo, aryl-$C_{1-6}$alkyl-NH— and —NH$C_{1-6}$alkyl;
wherein (1) is —H and $R^3$ is selected from the group consisting of
(a) imidazopyridinyl optionally substituted with from 1-3 $R^k$ members independently selected from the group consisting of aryl-$C_{1-4}$alkyl, halo, haloalkyl, —$OR^c$, —$SR^c$, —CN, —$NO_2$, $NR^cR^d$, oxo, $C_{1-4}$alkyl(C=O))NH—, haloalkoxy, —C(=O)$C_{1-4}$alkyl, OC(=O)$C_{1-4}$alkyl, —C(=O)$OR^c$, S(O)$C_{1-4}$alkyl, S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members;
(b) pyridyl, isoxazolyl, pyrimidinyl, benzodioxanyl, or pyrazolyl; each independently optionally substituted with from 1-3 $R^k$ members independently selected from the group consisting of $C_{1-4}$alkyl, aryl-$C_{1-4}$alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, and S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members; and
(c) aryl optionally substituted with from 1-3 $R^k$ members independently selected from the group consisting of $C_{1-4}$alkyl, aryl-$C_{1-4}$alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, and S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members; or (2) $R^3$ is —H and $R^4$ is benzoimidazolyl optionally substituted with from 1-3 $R^k$ members independently selected from the group consisting of $C_{1-4}$alkyl, aryl-$C_{1-4}$ alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members; wherein $R^c$ and $R^d$ are each independently selected from the group consisting of —H, $C_{1-6}$alkyl, —$R^e$, —NH$C_{1-6}$alkyl and —NH(C=O)$R^e$, wherein $R^e$ is a heteroaryl or heterocyclyl having from 1-4 ring heteroatoms selected from O, N or S or an aryl, wherein the aryl or heteroaryl is further optionally substituted with from 1-3 $R^f$ selected from the group consisting of halo, haloalkyl, —OH, —$OR^g$, —$SR^g$, —CN, —$NO_2$, $NR^gR^g$, oxo, haloalkoxy, —C(=O)$C_{1-4}$alkyl, OC(=O)$C_{1-4}$alkyl, —C(=O)$OR^g$, S(O)$C_{1-4}$alkyl and S(O)$_2C_{1-4}$alkyl, wherein $R^g$ is $C_{1-6}$alkyl; and wherein each subscript n is independently an integer selected from 0, 1, 2, or 3;
wherein $R^c$ and $R^d$ are each independently selected from the group consisting of —H, $C_{1-6}$alkyl, —$R^e$, —NH$C_{1-6}$alkyl and —NH(C=O)$R^e$, wherein $R^e$ is a heteroaryl or heterocyclyl having from 1-4 ring heteroatoms selected from O, N or S or an aryl, wherein the aryl or heteroaryl is further optionally substituted with from 1-3 $R^f$ selected from the group consisting of halo, haloalkyl, —OH, —$OR^g$, —$SR^g$, —CN, —$NO_2$, $NR^gR^g$, oxo, haloalkoxy, —C(=O)$C_{1-4}$alkyl, OC(=O)$C_{1-4}$alkyl, —C(=O)$OR^g$, S(O)$C_{1-4}$alkyl and S(O)$_2C_{1-4}$alkyl, wherein $R^g$ is $C_{1-6}$alkyl; and wherein each subscript n is independently an integer selected from 0, 1, 2, or 3; and
the aliphatic portions of $R^2$, $R^3$, and $R^4$ are each optionally independently substituted with from 1-3 $R^h$ substituents selected from the group consisting of $C_{1-6}$alkyl, $C_{1-6}$haloalkyl, $C_{1-6}$haloalkoxy, $C_{3-8}$cycloalkyl or $C_{2-6}$alkenyl is optionally substituted with $C_{1-6}$haloalkyl, halo, OH, $C_{1-4}$alkoxy, —NH$C_{1-4}$alkyl, N($C_{1-4}$alkyl)$_2$, —CN, —$N_3$, —O(C=O)$C_{1-4}$ alkyl, $C_{3-6}$cycloalkyl, —$NH_2$, —NHC(=O)$C_{1-4}$alkyl, —C(=O)$C_{1-4}$alkyl, $OR^c$, $SR^c$, CN, —$NO_2$, $NR^cR^d$, C(=O)$OC_{1-4}$alkyl, S(O)$C_{1-4}$alkyl and S(O)$_2C_{1-4}$alkyl.

2. The compound of claim 1, having formula If:

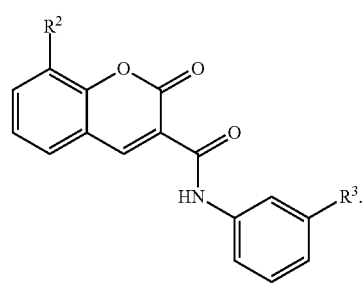

If

3. The compound of claim 2, having formula Ib-3:

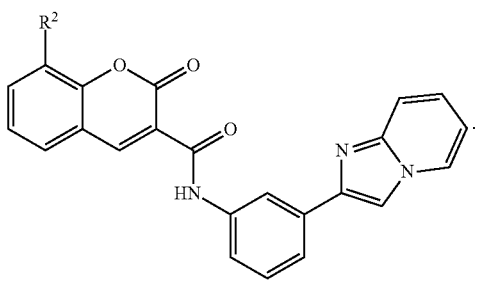

4. The compound of claim 1, wherein $R^2$ is —OH or $C_{1-6}$alkoxy.

5. The compound of claim 2, wherein $R^2$ is —OH or $C_{1-6}$alkoxy.

6. The compound of claim 3, wherein $R^2$ is —OH or $C_{1-6}$alkoxy.

7. The compound of claim 1, wherein $R^h$ is selected from the group consisting of —$CF_3$, $CF_3O$, halo, OH, $C_{1-4}$alkoxy, —$NHC_{1-4}$alkyl, $N(C_{1-4}$alkyl$)_2$, —CN, —$N_3$, —O(C=O)$C_{1-4}$alkyl, $C_{3-6}$cycloalkyl, —$NH_2$, —NHC(=O)$C_{1-4}$alkyl, —C(=O)$C_{1-4}$alkyl, —O($C_{1-6}$alkyl), —SH, —S($C_{1-6}$alkyl), —CN, —$NO_2$, —N($C_{1-6}$alkyl$)_2$, C(=O)O$C_{1-4}$alkyl, S(O)$C_{1-4}$alkyl and S(O)$_2C_{1-4}$alkyl.

8. A pharmaceutical composition comprising a compound of claim 1 and a pharmaceutically acceptable carrier or excipient.

9. A method of activating executioner procaspase 3, 6 and/or 7, said method comprising: contacting a compound of claim 1 with executioner procaspase 3, 6 and/or 7 receptor under conditions sufficient to activate executioner procaspase 3, 6 and 7.

10. The compound of claim 1, wherein $R^4$ is —H and $R^3$ is imidazopyridinyloptionally substituted with from 1-3 $R^k$ members independently selected from the group consisting of aryl-$C_{1-4}$alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members.

11. The compound of claim 1, wherein $R^4$ is —H and $R^3$ is pyridyl, isoxazolyl, pyrimidinyl, benzodioxanyl, or pyrazolyl; each independently optionally substituted with from 1-3 $R^k$ members independently selected from the group consisting of $C_{1-4}$alkyl, aryl-$C_{1-4}$alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, and S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members.

12. The compound of claim 1, wherein $R^4$ is —H and $R^3$ is aryl optionally substituted with from 1-3 $R^k$ members independently selected from the group consisting of $C_{1-4}$alkyl, aryl-$C_{1-4}$alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, and S(O)$_2$heterocycloalkyl and S(O)$_2C_{1-4}$alkyl, or optionally two adjacent $R^k$ substituents together with the atoms to which they are attached form an optionally substituted fused 5-or 6-membered heteroaryl or heterocycloalkyl ring having from 1-2 heteroatoms selected from O or N as ring members.

13. The compound of claim 1, wherein $R^4$ is —H and $R^3$ is phenyl optionally substituted with from 1-3 $R^k$ members independently selected from the group consisting of $C_{1-4}$alkyl, aryl-$C_{1-4}$alkyl, halo, haloalkyl, —$OR^c$, —$SR^c$, —CN, —$NO_2$, $NR^cR^d$, oxo, $C_{1-4}$alkyl(C=O)NH—, haloalkoxy, —C(=O)$C_{1-4}$alkyl, OC(=O)$C_{1-4}$alkyl, —C(=O)$OR^c$, S(O)$C_{1-4}$alkyl, and S(O)$_2$heterocycloalkyl and S(O)$_2C_{1-4}$alkyl, or optionally two adjacent $R^k$ substituents together with the atoms to which they are attached form an optionally substituted fused 5- or 6-membered heteroaryl or heterocycloalkyl ring having from 1-2 heteroatoms selected from O or N as ring members.

14. The compound of claim 1, wherein $R^4$ is —H and $R^3$ is selected from the group consisting of

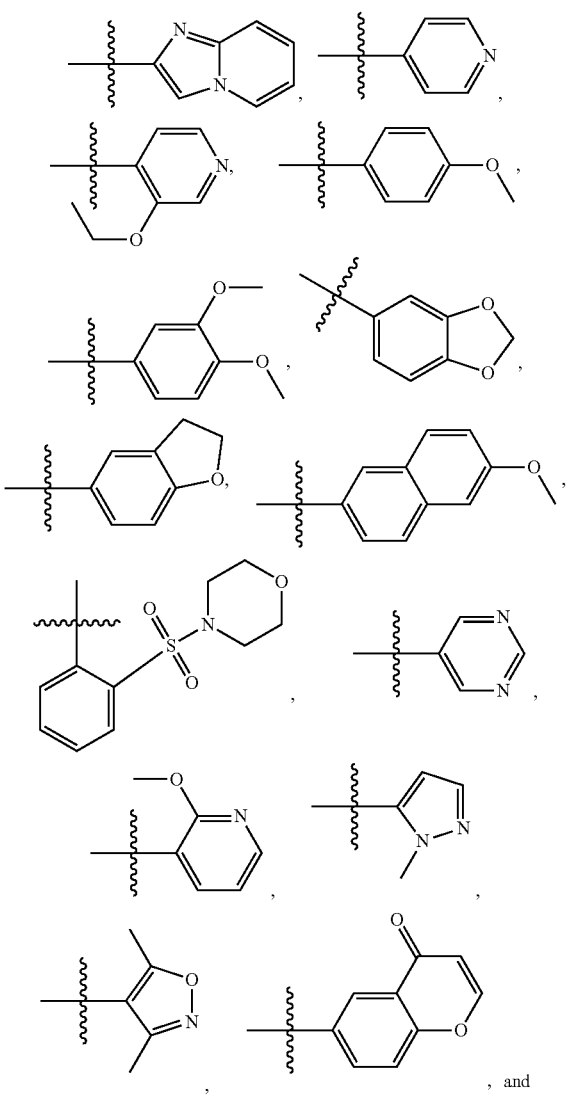

-continued
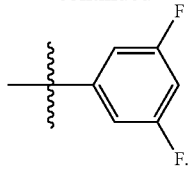
15. The compound of claim 1, wherein R³ is —H and R⁴ is
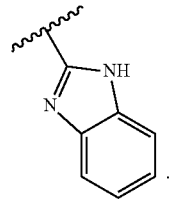 [SMILES: *c1nc2ccccc2[nH]1]
* * * * *